US012780945B2

(12) United States Patent
Bodie

(10) Patent No.: US 12,780,945 B2
(45) Date of Patent: Nov. 3, 2026

(54) ACE2-Fc FUSIONS AND USES THEREOF

(71) Applicant: Paradigm Immunotherapeutics, Inc., Monrovia, CA (US)

(72) Inventor: Neil M. Bodie, Monrovia, CA (US)

(73) Assignee: PARADIGM IMMUNOTHERAPEUTICS, INC., Monrovia, CA (US)

( * ) Notice: Subject to any disclaimer, the term of this patent is extended or adjusted under 35 U.S.C. 154(b) by 788 days.

(21) Appl. No.: 18/299,566

(22) Filed: Apr. 12, 2023

(65) Prior Publication Data

US 2023/0374153 A1 Nov. 23, 2023

Related U.S. Application Data

(60) Provisional application No. 63/480,373, filed on Jan. 18, 2023, provisional application No. 63/480,251, filed on Jan. 17, 2023, provisional application No. 63/330,716, filed on Apr. 13, 2022.

(51) Int. Cl.
*C07K 19/00* (2006.01)
*A61P 31/14* (2006.01)
*C07K 16/40* (2006.01)

(52) U.S. Cl.
CPC .............. *C07K 16/40* (2013.01); *A61P 31/14* (2018.01); *C07K 2317/52* (2013.01); *C07K 2317/55* (2013.01); *C07K 2317/92* (2013.01)

(58) Field of Classification Search
None
See application file for complete search history.

(56) References Cited

FOREIGN PATENT DOCUMENTS

| | | | |
|---|---|---|---|
| KR | 2021 0149593 | A | 12/2021 |
| WO | WO 2021/183717 | A1 | 9/2021 |
| WO | WO 2021/188576 | A1 | 9/2021 |
| WO | WO 2022/020353 | A2 | 1/2022 |

OTHER PUBLICATIONS

Wells (1990). Biochemistry 29:8509-8517.*
Ngo et al. (1994). The Protein Folding Problem and Tertiary Structure Prediction, pp. 492-495.*
Interanational Search Report and Written Opinion of PCT/US2023/018364 dated Aug. 10, 2023; 15 pages.
Bodie et al.,"Design of a chimeric ACE-2/Fc-silent fusion protein with ultrahigh affinity and neutralizing capacity for SARS-CoV-2 variants", Department of Physiology, Michigan State University, vol. 6, No. 1, Jan. 18, 2023, pp. 59-74, XP093069129, DOI: 10.1093/abt/tbad001.
Glasgow Anum et al., "Engineered ACE2 receptor traps potently neutralize SARS-CoV-2", Proceedings of the National Academy of Sciences, vol. 117, No. 45, Oct. 22, 2020, pp. 8046-28055, XP055957496.
Wilkinson et al., "Fc-engineered antibodies with immune effector functions completely abolished", PLOS ONE, vol. 16, No. 12, Dec. 21, 2021, p. e0260954, XP093016187, DOI: 10.1371/journal.pone.0260954.

* cited by examiner

*Primary Examiner* — Christine J Saoud
*Assistant Examiner* — Jon M Lockard
(74) *Attorney, Agent, or Firm* — SQUIRE PATTON BOGGS (US) LLP

(57) ABSTRACT

Methods and compositions to treat or prevent infections by respiratory virus, including SARS-CoV-2 (COVID-19). Included are chimeric antibodies comprising an immunoglobin region having an Fc domain that does not bind FcγRs and/or C1q, e.g. having substitutions L234S, L235T, G236R (STR), and an ACE2 domain having high affinity binding to a plurality of viral variants, e.g. having substitutions T27L or T27Y, H34V, N90E (LVE or YVE). The antibodies may have increased binding to FcRn, e.g. having substitutions M252Y, S254T, and T256E (YTE). The antibodies can be administered intranasally, by respiratory nebulization or systemically to treat or prevent respiratory viral infections.

13 Claims, 32 Drawing Sheets

Specification includes a Sequence Listing.

| ACE-2 Variant | SARS-2 variant | ΔE (DFIRE-A) | Prediction |
|---|---|---|---|
| T27L, H34V, N90E | w.t. Wuhan | -6.67 | Stabilizing |
| T27Y, L79T, N330Y | w.t. Wuhan | -4.53 | Stabilizing |

| ACE-2 Variant | SARS-2 variant | ΔE (DFIRE-A) | Prediction |
|---|---|---|---|
| T27L, H34V, N90E | w.t. Wuhan | -6.67 | Stabilizing |

| ACE-2 Variant | SARS-2 variant | ΔE (DFIRE-A) | Prediction |
|---|---|---|---|
| T27L, H34V, N90E | Delta B.1.617.2 | -6.80 | Stabilizing |

Inhibition of Delta Variant B.1.617.2 RBD (T478K, L452R) to ACE2 binding (sVNT) by "LiVE" IgG ACE2 chimeric mAb (red) and Wild type (WT) RBD to ACE2 binding (sVNT) by "LiVE" IgG ACE2 mAb (blue)

| ACE-2 Variant | SARS-2 Variant | ΔE (DFIRE-A) | Prediction |
|---|---|---|---|
| T27L,H34V,N90E | Omicron 7T9L | -3.38 | Stabilizing |

Inhibition of Omicron spike protein trimer to ACE2 binding (sVNT) by "LiVE" IgG ACE2 variant mAb (green) and Alpha spike protein S1 to ACE2 binding (sVNT) by "LiVE" IgG ACE2 variant mAb (blue)

Inhibition of Omicron spike protein trimer to ACE2 binding (sVNT) by "LiVE Longer" ACE2 LVE STR YTE chimeric antibody (green) and Omicron spike protein trimer to ACE2 binding (sVNT) by "LiVE" IgG ACE2 LVE STR mAb (blue)

| Method | Ligand | Ligand Cat. No. | Capture Level (RU) | Analyte | Analyte Conc. | ka (1/Ms) | kd (1/s) | KD (M) | Rmax (RU) | Chi² (RU²) | Fit model |
|---|---|---|---|---|---|---|---|---|---|---|---|
| His Capture | [illegible] | NA | 41.5 | [illegible] | 0.031-31.25 nM | 1.00E+06 | 1.52E-03 | 1.44E-10 | 41.5 | 0.22 | 1:1 Binding |

| | | | | | | | | | | | |
|---|---|---|---|---|---|---|---|---|---|---|---|
| Human IgG (Fc) Capture | cAb8185 | NA | 103.93 | SPN-C52H6 | 0.391-12.5 nM | 3.68E+05 | 3.41E-05 | 9.28E-11 | 130.8 | 0.29 | 1:1 binding |

FIG. 9A

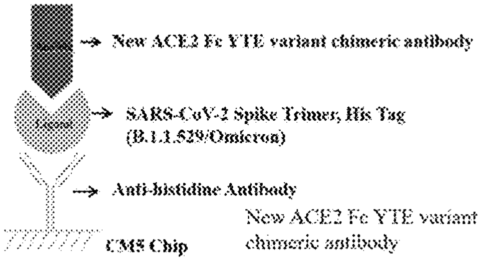

Principle :

1. Immobilization: Immobilized Anti-histidine Antibody on CM5 chip
2. Capture: SARS-CoV-2 Spike Trimer, His Tag (B.1.1.529/Omicron)
3. Analyte: New ACE2 Fc YTE variant chimeric antibody
4. Regeneration: 10 mM Glycine-HCl, pH1.5

New ACE2 Fc YTE variant chimeric antibody

SARS-CoV-2 Spike Trimer, His Tag (B.1.1.529/Omicron) (MALS verified)

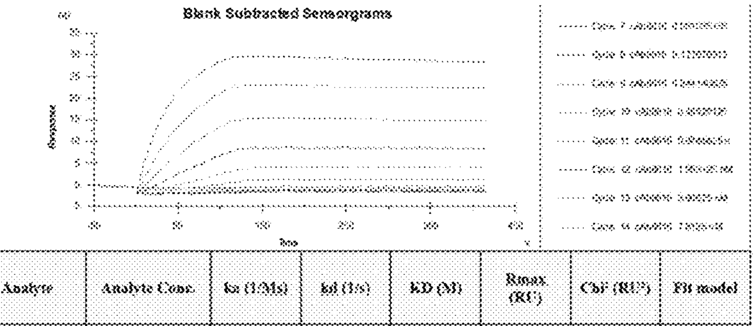

| Method | Ligand | Ligand Cat. No. | Capture Level (RU) | Analyte | Analyte Conc. | ka (1/Ms) | kd (1/s) | KD (M) | Rmax (RU) | Chi² (RU²) | Fit model |
|---|---|---|---|---|---|---|---|---|---|---|---|
| His Capture | SPN-C52Hz | NA | 101.9 | cAb6186 | 0.031-15.63 nM | 1.59E+06 | 1.17E-04 | 7.34E-11 | 32.8 | 0.05 | 1:1 binding |

| Method | Ligand | Ligand Cat. No. | Capture Level (RU) | Analyte | Analyte Conc. | ka (1/Ms) | kd (1/s) | KD (M) | Rmax (RU) | Chi² (RU²) | Fit model |
|---|---|---|---|---|---|---|---|---|---|---|---|
| His Capture | SPN-C5223 | NA | 369.7 | cA08156 | 0.122-15.63 nM | 1.35E+06 | 1.04E-07 | 7.82E-14 | 59.5 | 0.22 | 1:1 binding |

New ACE2 Variant Chimeric Antibody

Human FcRn / FCGRT&B2M Heterodimer
Protein, His Tag (SPR & BLI & MALS verified)

New ACE2 Fc YTE Variant
Chimeric Antibody

Human FcRn / FCGRT&B2M Heterodimer
Protein, His Tag (SPR & BLI & MALS verified)

| Method | Ligand | Ligand Cat. No. | Capture Level (RU) | Analyte | Analyte Conc. | ka (1/Ms) | kd (1/s) | KD (M) | Rmax (RU) | Chi² (RU²) | Fit model |
|---|---|---|---|---|---|---|---|---|---|---|---|
| His Capture | FCN-H52W7 | NA | 86.9 | Ab7918 | 7.81-500 nM | NA | NA | **5.17E-7** | 9.71 | 0.64 | Steady state affinity |
| His Capture | FCN-H52W7 | NA | 82.8 | cAb8186 | 3.91-500 nM | 1.55E+05 | 4.12E-03 | **2.67E-8** | 43.1 | 1.32 | 1:1 binding |

Figure 11a. Analysis of binding to Fc receptors in vitro by surface plasmon resonance (SPR, Biacore) [A] and in cell-based reporter assays

Figure 11b. Comparison of silencing approaches in their relative binding to human FcγRI (CD64) by surface plasmon resonance (SPR, Biacore).

Figure 11c. Release of cytokines from human PMBCs exposed to CD3 binding antibodies.

<Results>

Viral copy number in culture medium/mL (detection limit 640 copies/mL)

| LiVE Fc fusion (C-term) | | concentration (μg/mL) | | | | | | | |
|---|---|---|---|---|---|---|---|---|---|
| | | 0 | 0.0064 | 0.032 | 0.16 | 0.8 | 4 | 20 | 100 |
| viral copy number (/mL) | average | 2,513,368 | 1,569,412 | 4,124,022 | 134,354 | 6,023 | 755 | 564 | 701 |
| | stdev | 472,614 | 421,839 | 5,201,362 | 81,536 | 4,582 | 596 | 159 | 198 |
| inhibition (%) | average | 0.00 | 38.37 | 32.82 | 95.03 | 99.72 | 99.97 | 99.98 | 99.97 |
| | stdev | 18.81 | 16.78 | 38.78 | 3.22 | 0.18 | 0.03 | 0.01 | 0.01 |

| LiVE longer Fc fusion (C-term) | | concentration (μg/mL) | | | | | | | |
|---|---|---|---|---|---|---|---|---|---|
| | | 0 | 0.0064 | 0.032 | 0.16 | 0.8 | 4 | 20 | 100 |
| viral copy number (/mL) | average | 3,411,497 | 1,794,325 | 1,048,936 | 54,480 | 10,697 | 1,368 | 1,836 | 1,796 |
| | stdev | 1,544,786 | 598,959 | 862,035 | 37,639 | 3,081 | 1,230 | 248 | 1,833 |
| inhibition (%) | average | 0.00 | 47.40 | 69.72 | 98.40 | 99.69 | 99.96 | 99.95 | 99.95 |
| | stdev | 45.27 | 18.89 | 19.09 | 1.10 | 0.09 | 0.04 | 0.01 | 0.05 |

ACE2-Fc FUSIONS AND USES THEREOF

CROSS-REFERENCE TO RELATED APPLICATIONS

This application claims priority to and the benefit of United States provisional patents application number 63/330,716, filed on Apr. 13, 2022; application Ser. No. 63/480,251, filed on Jan. 17, 2023; and application Ser. No. 63/480,373, filed on Jan. 18, 2023; each of which is incorporated by reference herein in its entirety, expressly including drawings, for all purposes.

REFERENCE TO AN ELECTRONIC SEQUENCE LISTING

The contents of the electronic sequence listing (12600600006.xml; Size: 20,809 bytes; and Date of Creation: Jul. 13, 2023) are herein incorporated by reference in their entireties.

BACKGROUND

SARS-CoV-2 and other respiratory viruses appear to start their infection in the upper respiratory tract. In the case of SARS-CoV-2 the initial point of infection can be the neuroepithelium of the olfactory bulb. Prior infection and/or treatment with antibodies can increase the risk of antibody-dependent disease processes that may increase mortality and can compromise patient health for months and years. As SARS-CoV-2 continues to mutate into Variants of Concern (VOC), antibodies developed earlier are no longer capable of effectively neutralizing currently active VOCs. There is a growing and urgent need to develop effective antiviral compounds and methods to combat COVID-19 and other diseases or conditions caused by respiratory virus infection.

SUMMARY OF INVENTION

This invention discloses compositions and methods to treat and/or prevent infection, especially at the upper and/or lower respiratory tract, from respiratory viruses including but not limited to SARS-CoV-2 using chimeric antibodies (also referred to herein as "chimeras"). The chimeric antibodies include a respiratory virus-binding domain of a protein, or variant thereof, that has higher (tighter) binding to the virus than do commonly occurring variants of the protein in potential hosts.

Described herein are chimeric antibodies having an Angio-tensin Converting Enzyme-2 (ACE2) domain having high or ultrahigh affinity binding to a plurality of SARS-CoV-2 variants, coupled to an immunoglobulin domain, e.g., IgG. The immunoglobin domain can have reduced ("silenced") Fc effector function. The chimeric antibody can have increased binding to FcRn and extended half-life compared to similar proteins.

The chimeric antibodies can have picomolar or femtomolar binding affinity to one or more SARS-CoV-2 variants. The chimeric antibodies can have high binding affinity to Alpha, Beta, Gamma, Delta, and/or Omicron variants, wherein examples include: Alpha B1.1.7, Delta B.1.617.2 Omicron BA.1, Omicron B.1.1.529, Omicron BA.2, Omicron BA2.75, Omicron BA4.6, Omicron BA.5, Omicron BQ.1.1, Omicron XBB.1, and Wuhan variant.

The chimeric antibodies can prevent, ameliorate or eliminate antibody -dependent enhancement (ADE), including antibody-dependent inflammation (ADI) and other processes.

In one embodiment, the chimeric antibodies include Fc mutations 5234, T235, and R236 ("STR-Fc domain" or "STR"). The chimeric antibodies can have reduced, e.g., eliminated, Fc effector function. Chimeric antibodies having the STR-Fc domain and/or reduced Fc effector function can ameliorate or eliminate ADE, including ADI and/or other processes.

In one embodiment, the chimeric antibodies include ACE2 mutations L27, V34 and E90 ("LVE-ACE2 domain" or "LVE"). Chimeric antibodies having the LVE-ACE2 domain can have an estimated dissociation constant ($K_D$), indicating affinity of the domain for a target, measured as the concentration of antibody at which half the antibody binding sites are occupied at equilibrium, of about 93 pM, about 507 pM and/or about 73 pM for, respectively, one or more Alpha, Delta and/or Omicron variants of SARS-CoV-2, e.g., Alpha B1.1.7, Delta B.1.617.2 and/or Omicron B.1.1.529 variants of SARS-CoV-2. The LVE-ACE2 domain can have $K_D$ values of about 78fM, 133 fM, and/or 1.81 pM for one or more Omicron variants of SARS-CoV-2, e.g., 78 fM affinity to the Omicron BA.2 subvariant, 133fM affinity to the Omicron BA2.75 subvariant, and/or 1.81pM affinity to the Omicron BQ.1.1 subvariant. Chimeric molecules having the LVE-ACE2 domain can have Surrogate Virus Neutralization Test (sVNT) titers, indicating detection of SARS-CoV-2 neutralizing antibodies, of ≥4.9 ng/ml for one or more Alpha, Delta and/or Omicron variants, e.g., Alpha B1.1.7, Delta B.1.617.2 and/or Omicron B.1.1.529 variants of SARS-CoV-2.

In one embodiment, the chimeric antibodies bind to FcRn. They may include an FcRn-binding sequence, which, in a preferred embodiments, includes mutations Y252, T254, E256 ("YTE-Fc domain" or "YTE"). Chimeric antibodies having the YTE-Fc domain can have extended biological half-life, particularly if administered to nasal passages. The biological half-life can be extended 3-4-fold over wild type sequences.

In a preferred embodiment, the chimeric antibodies include an LVE-ACE2 domain and a YTE-Fc domain. In another embodiment, the chimeric antibodies include an LVE-ACE2 domain, a YTE-Fc domain, and a STR-Fc domain.

In one embodiment, a chimeric antibody, e.g., as described herein, can be used in an excipient with a mildly acidic pH, such as a pH of 5.5-6.0. The antibody can include but is not limited to an ACE2 variant chimeric antibody with increased binding affinity for SARS-CoV-2 spike protein trimer, SARS-CoV-2 S1 and/or SARS-CoV-2 RBD. The increased binding affinity can be indicated, for example, by $K_D$ less than 900 pM, less than 600 pm, less than 500 pm, less than 400 pm, less than 300 pm, less than 200 pm, and/or less than 100 pm. The increased binding affinity can be indicated, for example, by $K_D$ less than 600 nm, less than 100 nm, less than 50 nm, less than 10 nm, less than 200 fm and/or less than 100 fm. The increased binding affinity can be indicated, for example, by $K_D$ less than 100 nm, less than 50 nm and/or less than 10 nm. The ACE2 variant chimeric antibody can have increased binding affinities to multiple SARS-CoV-2 variants of concern (VOC), for example, as defined by the World Health Organization (W.H.O.). The antibody can include, but is not limited to, an IgG, IgA or hexameric IgM isotype.

Presented are methods to treat or prevent respiratory virus infections in a subject, including, but not limited to infection caused by SARS-CoV-2 (e.g. COVID-19). In one or more embodiments, the subject is a human or a non-human primate. In a preferred embodiment, the subject can be administered an antibody disclosed herein intranasally or by respiratory application, e.g. nebulization, to prevent respiratory viral infections, including, but not limited to SARS-CoV-2 (e.g. COVID-19) infections. In another embodiment, the subject can be administered an antibody disclosed herein systemically, e.g. by injection, to prevent respiratory viral infections, including, but not limited to SARS-CoV-2 (e.g. COVID-19) infections.

In another embodiment, the antibodies disclosed herein can be administered to a subject intranasally, by respiratory application or systemically, e.g. by injection, to treat respiratory viral infections, including, but not limited to SARS-CoV-2 (e.g. COVID-19) infections. In another embodiment, the antibodies disclosed herein can be administered to a subject intranasally, by respiratory application or systemically, e.g. by injection, for pre-exposure prophylaxis or post-exposure prophylaxis, including, but not limited to prophylactic treatment of actual or potential SARS-CoV-2 (e.g. COVID-19) infections. Administration of chimeric antibodies can ameliorate, prevent, or lessen the severity of respiratory viral infection and disease.

In one or more embodiments, the subject can have a compromised immune system (an "immunocompromised individual"), which may include infection with a disease that results in immunosuppression, including, but not limited to human immunodeficiency virus (HIV), cancer, including, but not limited to B and T cell neoplasia or treatment using immunosuppressive drugs, including, but not limited to corticosteroids, immunosuppressive drugs, immunomodulatory drugs, chemotherapy, immunotherapy, radiotherapy and primary or secondary immunosuppression. The immunocompromised individual may have or be suspected of having an autoimmune disease, including but not limited to post-COVID-19 syndrome or post-acute sequalae of COVID-19 (PASC), also known as "Long Covid."

In one or more embodiments, the subject is at risk of increased (e.g. higher than normal) mortality or disease process due to infection, which may include respiratory conditions such as asthma or emphysema, age, gender, genetics, other disease processes, infirmity, or the like.

BRIEF DESCRIPTION OF THE DRAWINGS

The features of the invention are set forth with particularity in the detailed description that follows and in the appended claims.

variant chimeric IgG mAb neutralizes the Delta RBD approximately the same it neutralizes the WT RBD.

Figure 3A:
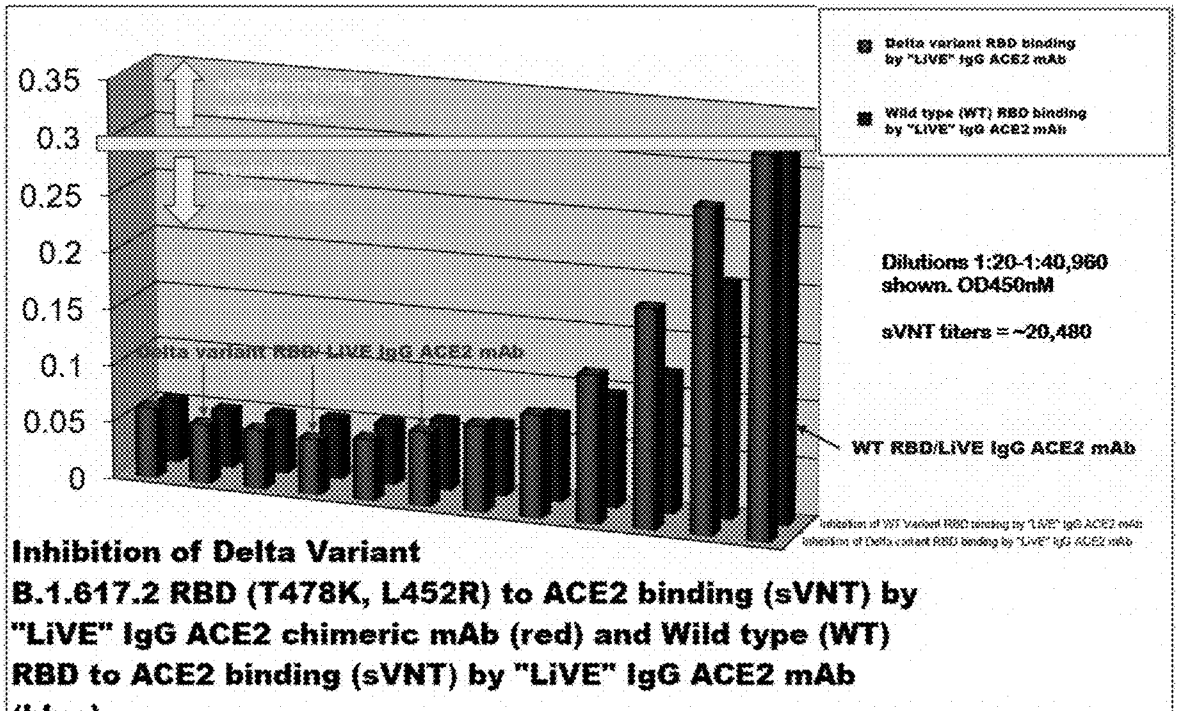
FIG. 3A shows that in the C-Pass surrogate Viral Neutralization Test ("C-Pass sVNT Test" or "sVNT Test") (GenScript USA Inc. 860 Centennial Ave. Piscataway, NJ 08854), the ACE2 "LiVE" variant (ACE2 T27L, H34V, N90E IgG Fc 234S 235T 236R) chimeric antibody neutralizes the original Wuhan ("Wild type" or "WT") SARS-CoV-2 RBD (ACRO Biosystems Cat No.: SPD-052H1 SARS-CoV-2 (COVID-19) S protein RBD, His Tag)/HRP conjugate (HRP Conjugation kit-Lighting Link-Abcam Cat. No. ab102890) (shown in blue) approximately the same as it neutralizes the Delta variant SARS-CoV-2 RBD (ACRO Biosystems Cat No.: SPD-05226 SARS-CoV-2 Spike RBD (K417N, L452R, T478K), His Tag/HRP conjugate (HRP Conjugation kit-Lighting Link-Abcam Cat. No. ab102890) (shown in red). An optical density (O.D.) <0.3 is neutralizing. Both the WT RBD and the Delta variant RBD have sVNT titers of 1:20,480 showing that the ACE2 "LiVE"
Figure 3B:
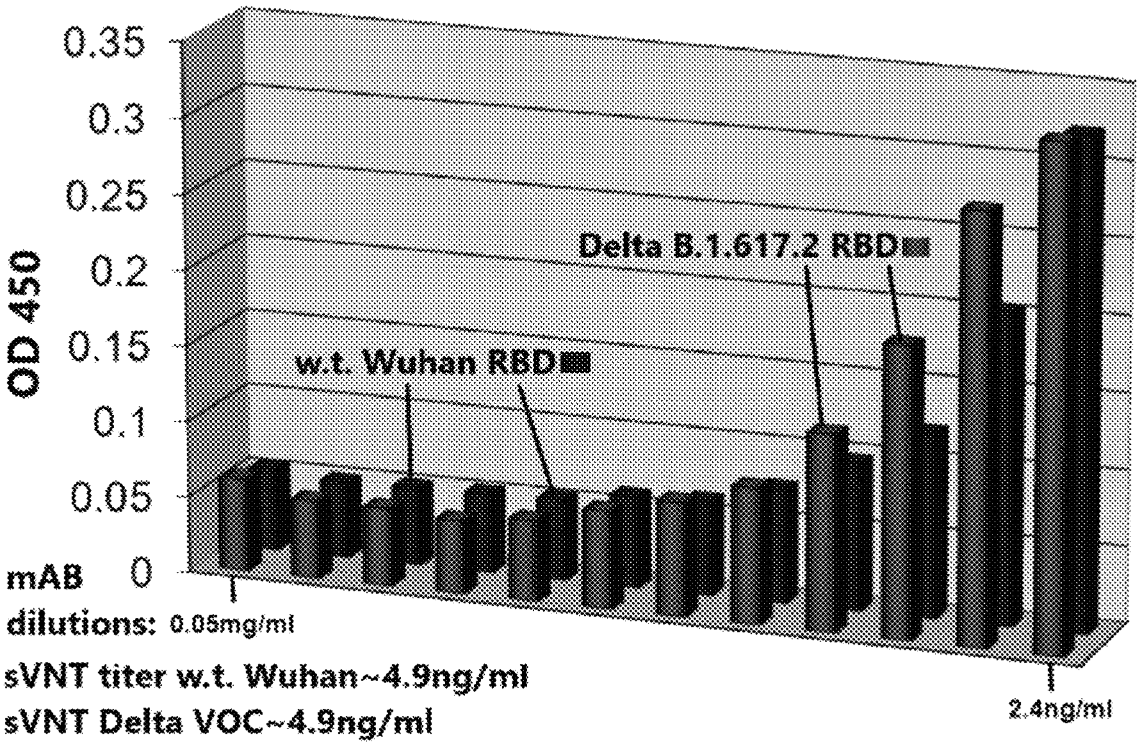

FIG. 3B shows the same results as presented in FIG. 3A, but indicates dilutions as concentrations instead of ratios. Dilutions shown are 0.05 mg/ml to 2.4 ng/ml, left to right. Both the WT SARS-CoV-2 RBD and the Delta variant RBD have similar sVNT titers of ~4.9 ng/ml.

Figure 3C:
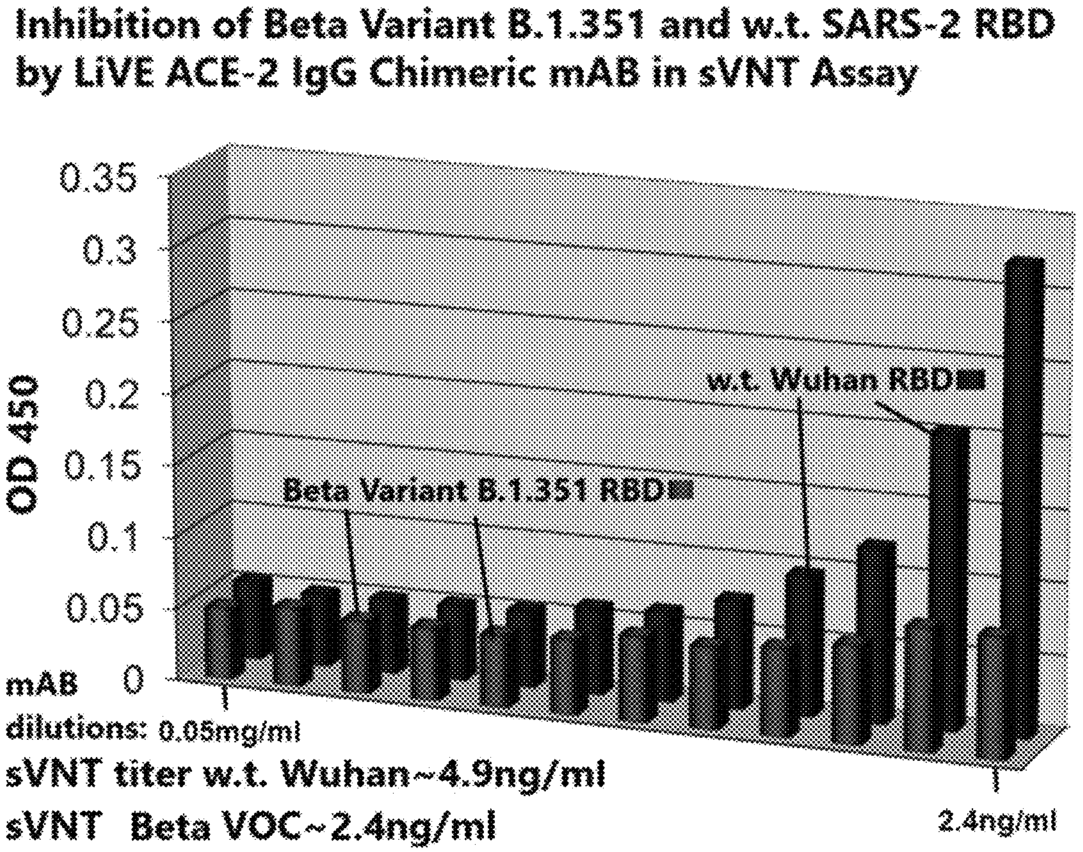

FIG. 3C shows that in the C-Pass sVNT Test, the ACE2 LVE STR chimera neutralizes the RBD of the SARS-CoV-2 Beta variant B.1.351 with greater potency (red front bars, ~2.4 ng/ml) than for the w.t. RBD (blue back bars, ~4.9 ng/ml).

Figure 3D:
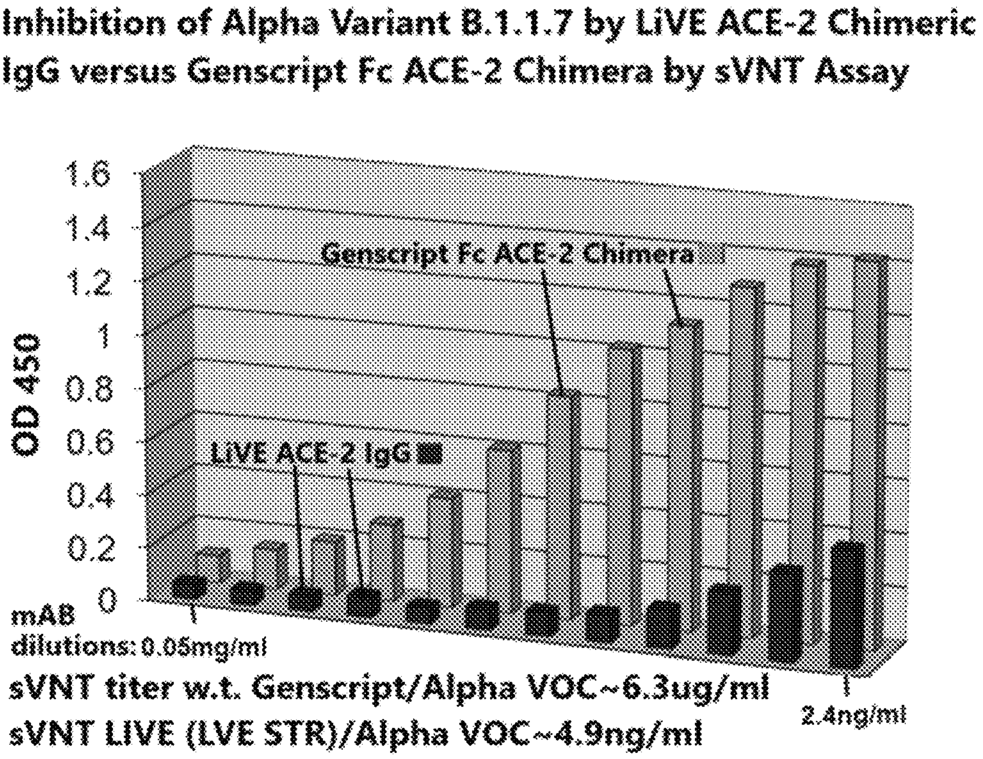

FIG. 3D shows that in the C-Pass sVNT Test, the ACE2 LVE STR chimera neutralizes the RBD of the SARS-CoV-2 Alpha variant B1.1.7 significantly better (dark blue front bars, ~4.9 ng/ml) than did the Genscript Fc-IgG/ACE2 chimera Z03516 (light blue back bars, ~6.3ug/ml).

Figure 3E:
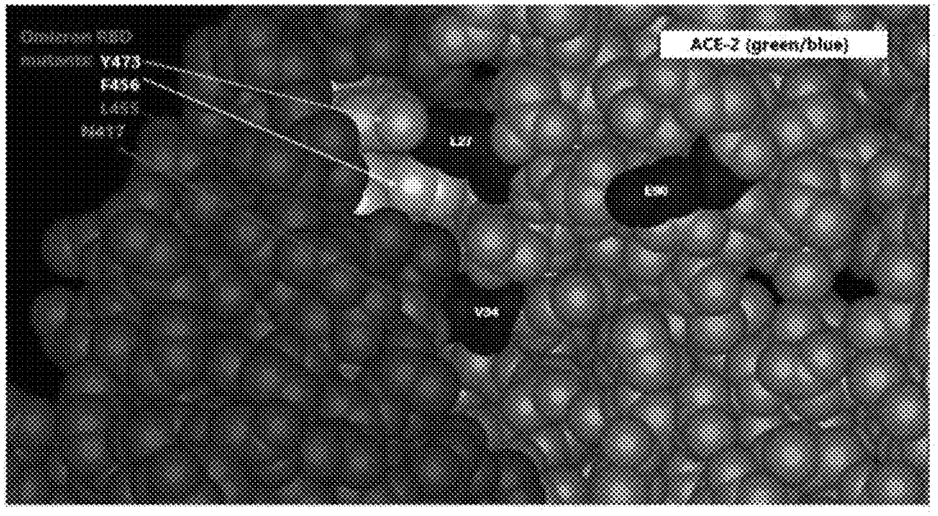
Figure 3E:
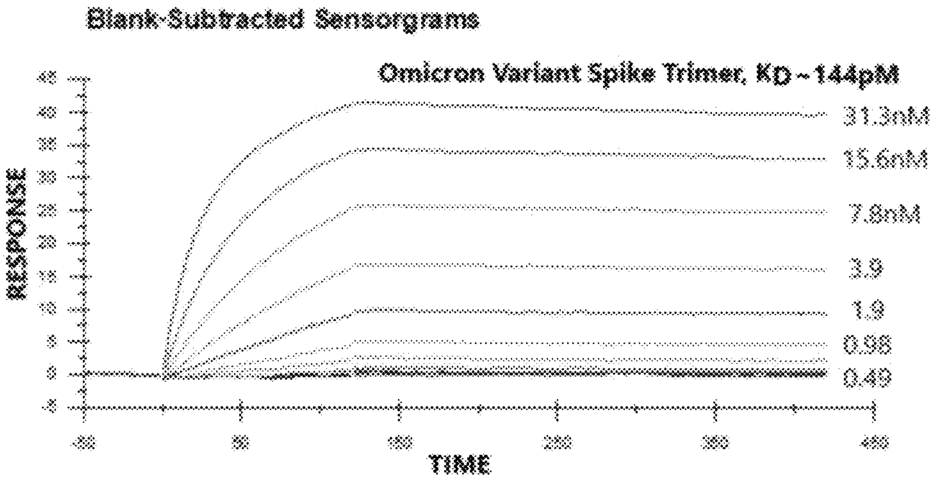

FIG. 3E shows, in the top panel, a three-dimensional model of the ACE2/SARS-CoV-2 interface for the ACE2 LVE variant and the RBD of the Omicron variant (RBD sequence as of 12/10/2021 at 75% cutoff), as described in Example 1. Of note, the aliphatic side chain of the Omicron Q493R mutation (purple) makes contact with ACE2 mutation V34. In molecular modeling, simulation of the ACE2 LVE/STR chimera binding to the Omicron variant yielded a very favorable DFIRE score of −7.26, indicating a tight, stabilizing interaction. The S1 subunit trimer of SARS-CoV-Omicron variant was synthesized, purified and subjected to SPR assay against the purified LVE/STR chimera. As shown in the bottom panel, the determined binding affinity was 0.144 nM (Acro Biosystems).

Figure 4:
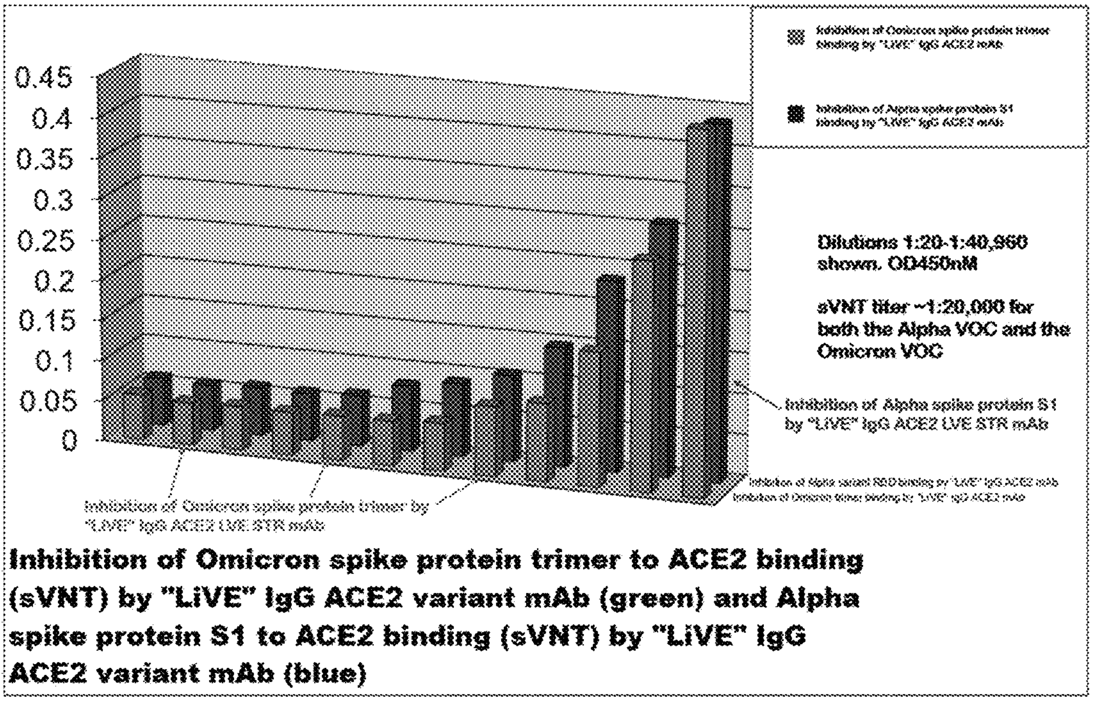

FIG. 4 shows that in the C-Pass sVNT Test, the ACE2 LVE IgG Fc STR chimera ("LiVE") neutralizes the spike protein trimer of the Omicron BA.1 variant (ACRO Biosystinfiems Cat. No.: SPN-052Hz SARS-CoV-2 Spike Trimer, His Tag B.1.1.529/Omicron)/HRP conjugate (HRP Conjugation kit-Lighting Link, Abcam Cat. No. ab102890) (green front bars) approximately as well as it neutralized the spike protein trimer of the Alpha variant B.1.1.7 (ACRO Biosystems SPN-052H6 SARS-CoV-2 S protein (HV69-70de1, Y144del, N501Y, A570D, D614G, P681H, T716I, S982A, D1118H), His Tag HRP)/HRP conjugate (HRP Conjugation kit-Lighting Link-Abcam Cat. No. ab102890) (blue back bars), with sVNT titers of ~1:20,000 for both, indicating the ACE2 LVE IgG Fc STR chimeric antibody is variant resistant to the Omicron and Alpha SARS-CoV-2 VOCs.

Figure 5:
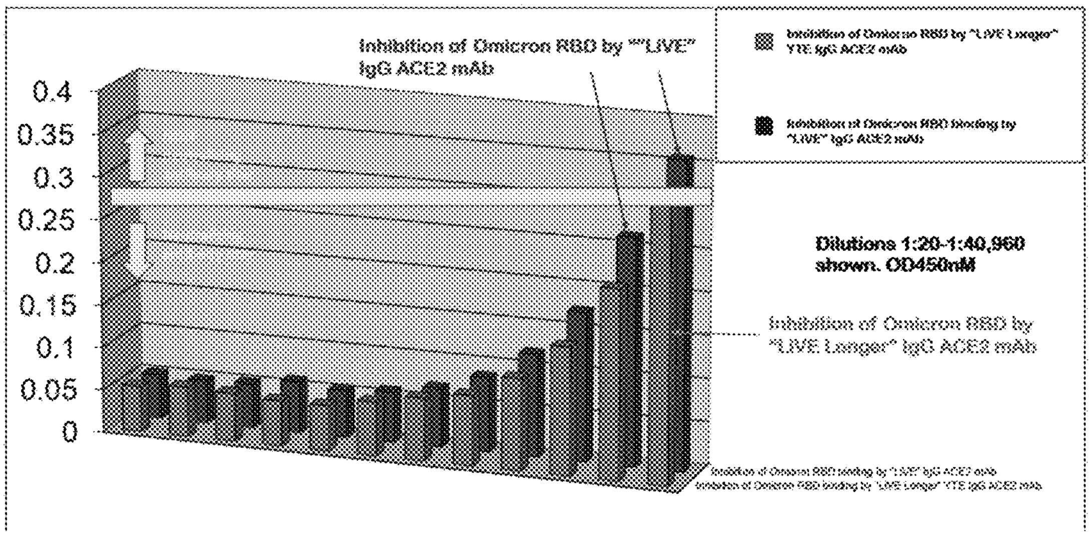

FIG. 5 shows that in the C-Pass sVNT Test, the ACE2 LVE IgG Fc STR chimera ("LiVE") neutralizes the RBD of the Omicron variant (ACRO Biosystems Cat. No.: SPD-052H3 SARS-CoV-2 (COVID-19) S protein RBD, His Tag B.1.1.529/Omicron)/HRP conjugate (HRP Conjugation kit-Lighting Link, Abcam Cat. No. ab102890) (blue back bars) approximately as well as the ACE2 LVE IgG Fc STR YTE chimera ("LiVE Longer") neutralizes the RBD of the Omicron variant (green front bars), demonstrating that the addition of the IgG Fc YTE mutations in the "LiVE Longer" chimeric antibody do not affect ACE2 to Omicron RBD neutralization. Note that the "LiVE Longer" chimeric antibody slightly outperformed the "LiVE" chimeric antibody, even though the sVNT titers for both are ~1:20,480.

Figure 6:
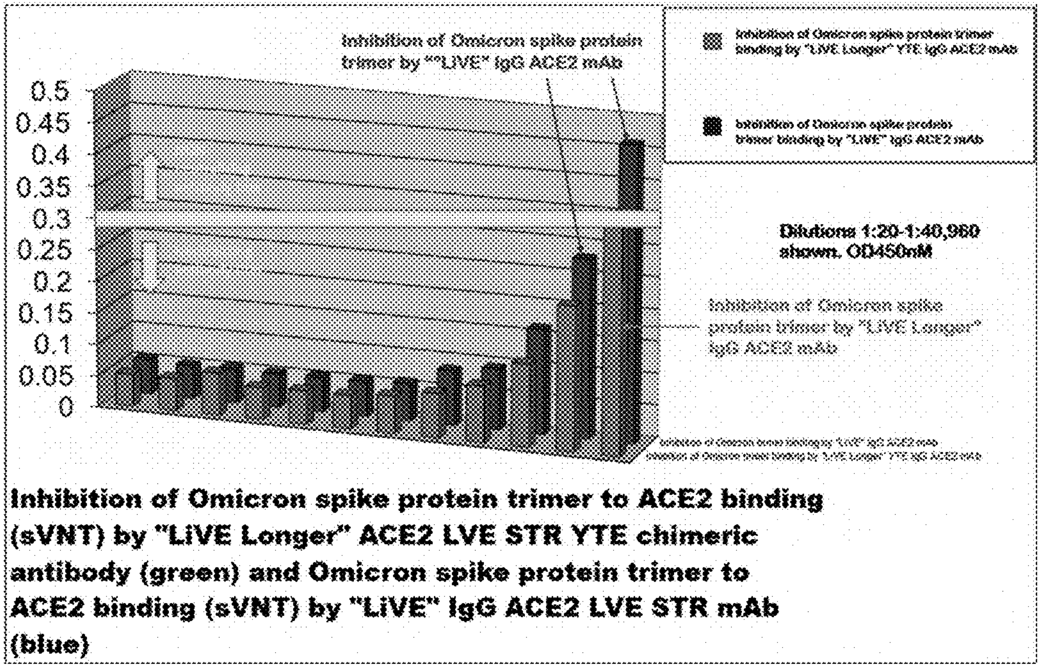

FIG. 6 shows that in the C-Pass sVNT Test, the "LiVE" chimeric antibody neutralizes the spike protein trimer of the Omicron BA.1 variant (ACRO Biosystems Cat. No.: SPN-052Hz SARS-CoV-2 Spike Trimer, His Tag B.1.1.529/Omicron)/HRP conjugate (HRP Conjugation kit-Lighting Link, Abcam Cat. No. ab102890) (blue back bars) approximately as well as the "LiVE Longer" chimeric antibody (green front bars), demonstrating that the addition of the IgG Fc YTE mutations in the "LiVE Longer" chimeric antibody do not significantly affect ACE2 to Omicron spike protein trimer neutralization. Note that the "LiVE Longer" chimeric antibody slightly outperformed the "LiVE" chimeric antibody, even though the sVNT titers for both are ~1:20,480.

Figure 7:
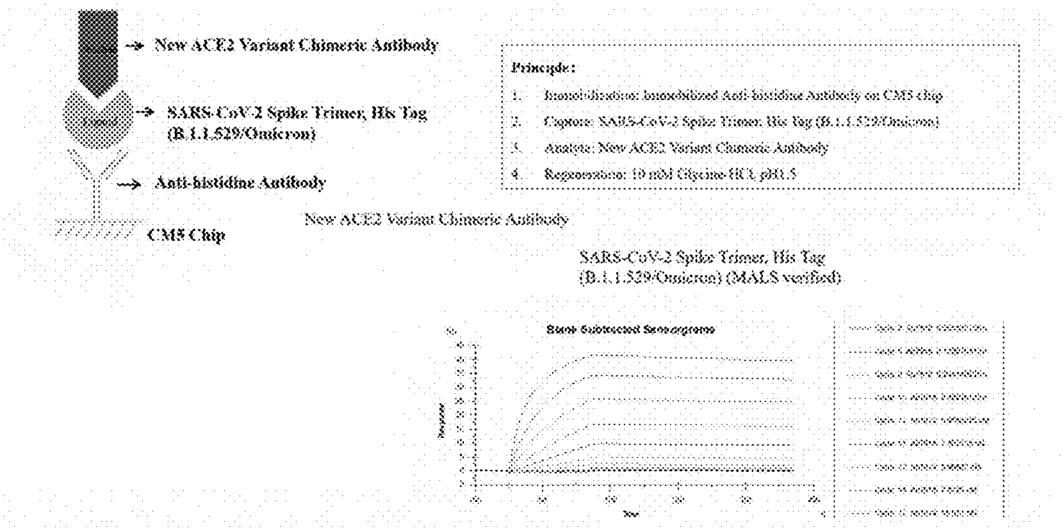

FIG. 7 provides the actual binding affinity data for the ACE2 LVE IgG Fc STR ("LiVE") variant against the Omicron B.1.1.529 spike protein trimer (BIACore SPR analysis performed by ACRO Biosystems, as described in Example 4). The binding affinity is 114 pM (0.114 nM).

Figure 8:
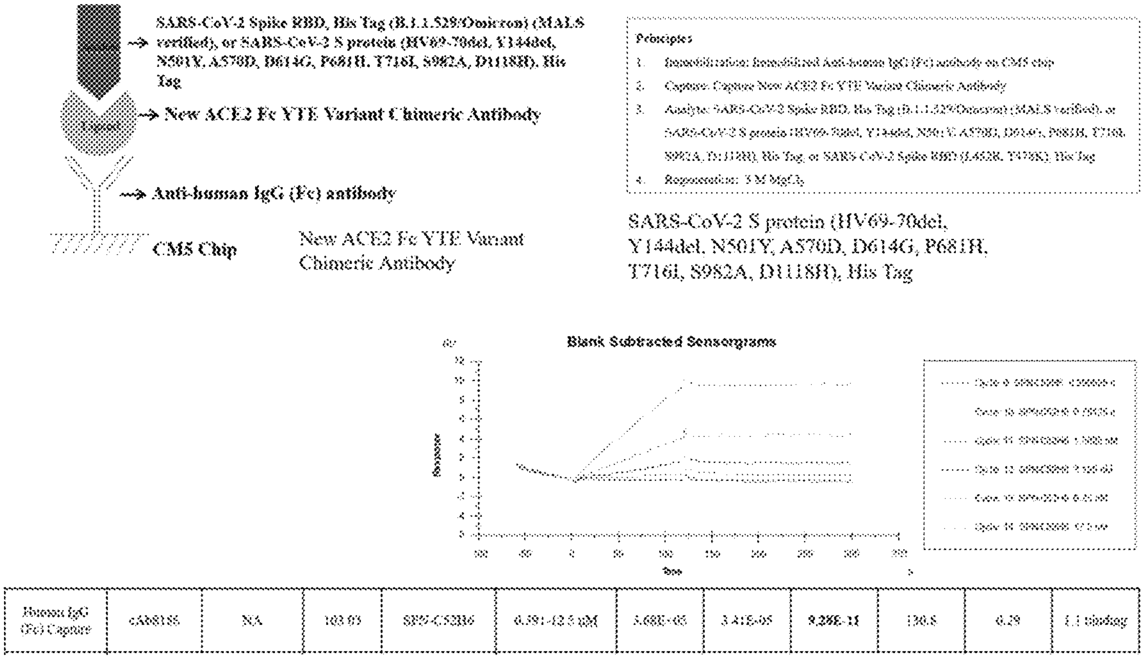

FIG. 8 provides the actual binding affinity data for the ACE2 LVE IgG Fc STR YTE ("LiVE Longer") variant against the Alpha spike protein trimer (BIACore SPR analysis performed by ACRO Biosystems, as described in Example 4). The binding affinity is 92.8 pM (0.0928 nM).

FIG. 9A provides the actual binding affinity data for the ACE2 LVE IgG Fc STR YTE ("LiVE Longer") variant against the Omicron B.1.1.529 spike protein trimer (BIACore SPR analysis performed by ACRO Biosystems for "B.1.1.529/Omicron", as described in Example 4). The binding affinity is 73.4 pM (0.0734 nM).

Figure 9B:
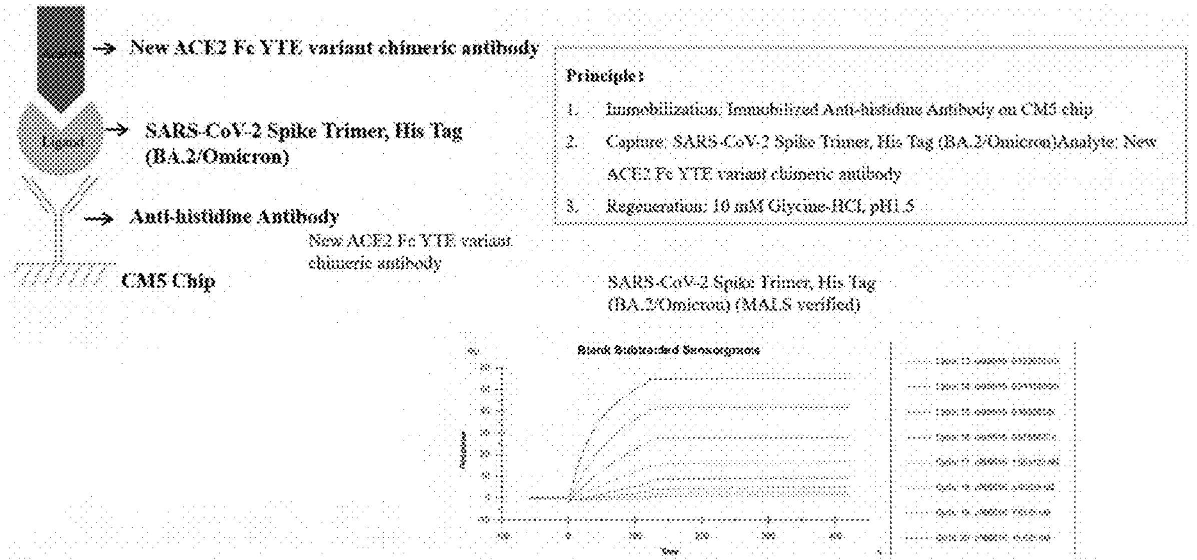

FIG. 9B provides the actual binding affinity data for the ACE2 LVE IgG Fc STR YTE ("LiVE Longer") variant against the new Omicron BA.2 sub-VOC (BIACore SPR analysis performed by ACRO Biosystems for "BA.2/Omicron", as described in Example 4). The binding affinity is 78.2fM (femtomolar). The $K_D$ for the "LiVE Longer" mAb against the Omicron BA.2 sub-VOC, which is fueling the next world-wide wave of SARS-CoV-2, is thus ~1,000 times better than the $K_D$ for the "LiVE Longer" mAb against the "original" Omicron BA.1 VOC (73.4 pM, FIG. 9A).

Figure 10A:
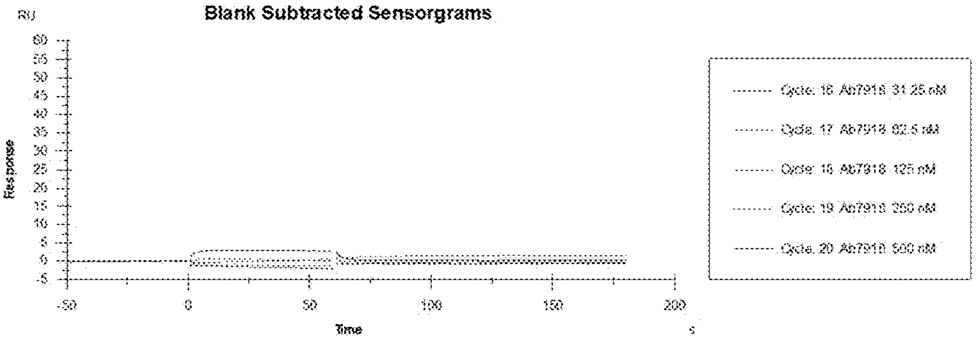

FIG. 10A provides the actual binding affinity data for the ACE2 LVE IgG Fc STR ("LiVE") variant for FcRn (BIACore SPR analysis performed by ACRO Biosystems, as described in Example 4). The binding affinity is 517 nM for FcRn at pH 6.0.

Figure 10B:
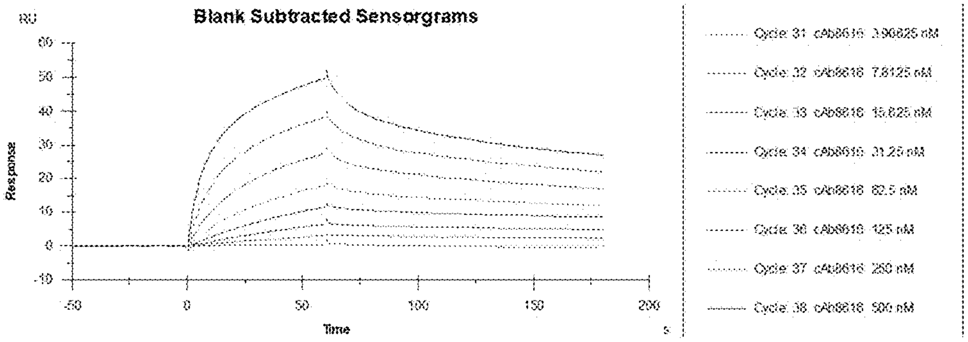

FIG. 10B provides the actual binding affinity data for the ACE2 LVE IgG Fc STR YTE ("LiVE Longer") variant for FcRn (BIACore SPR analysis performed by ACRO Biosystems, as described in Example 4). The binding affinity is 26.7 nM for FcRn at pH 6.0.

Figure 11:
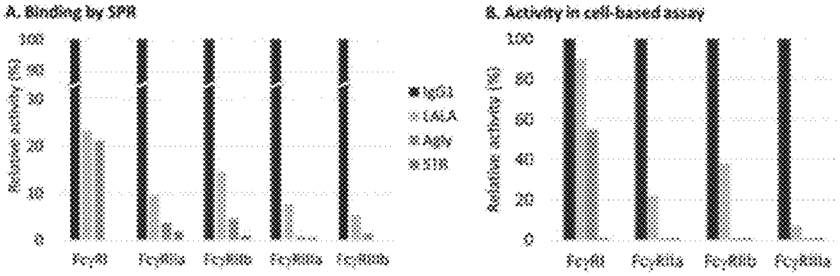
Figure 11:
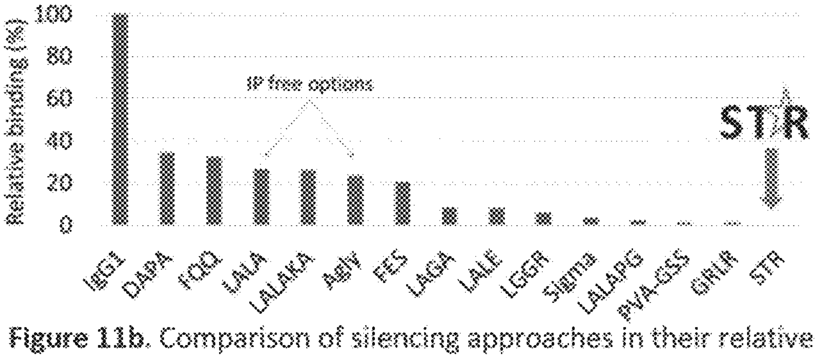
Figure 11:
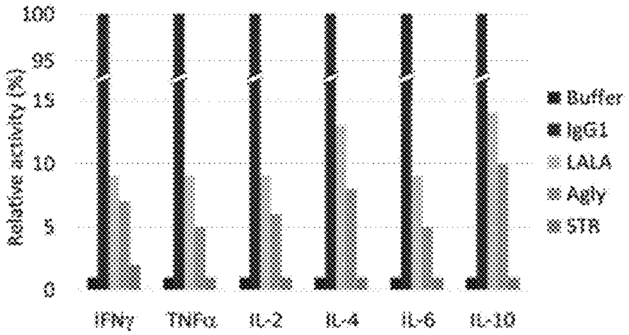

FIG. 11 shows that Fc Silent technology ("STR") has less binding to all classes of activating and inhibiting FcγRs (FcγRI, FcγRIIA/b and FcγRIII) as compared to wild type, and other mutations, as reported by and at mabsolve.com/science/#linkone.

Figure 12:
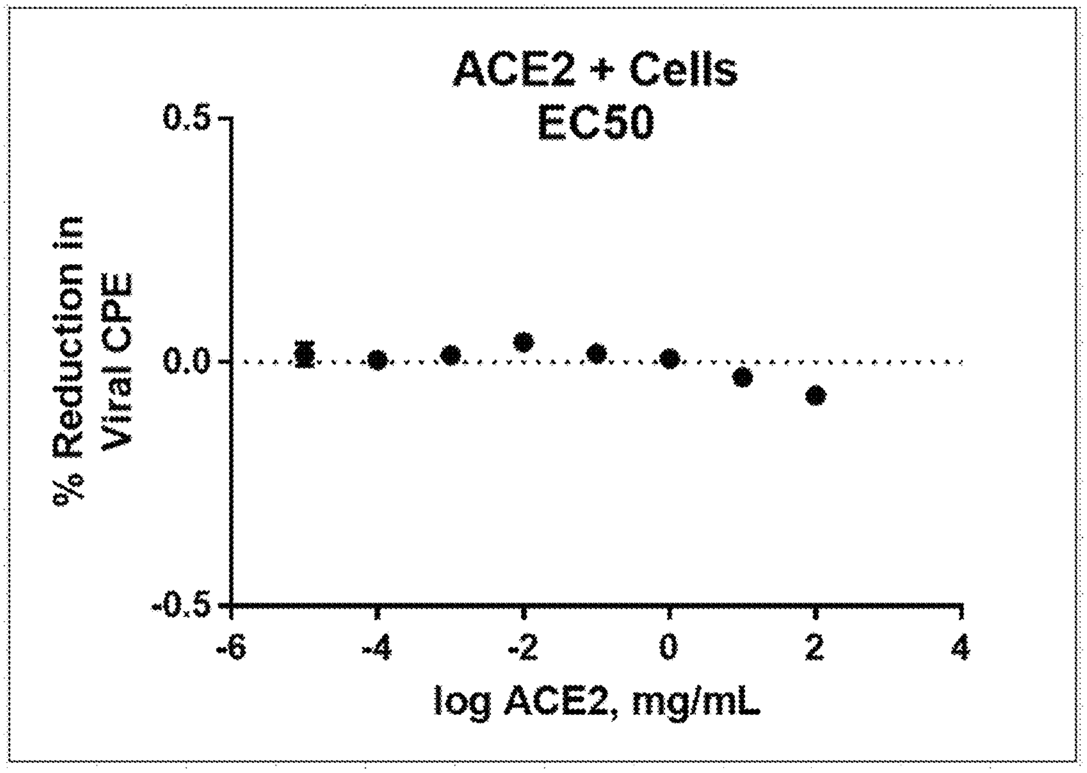

FIG. 12 shows potential C'ADE of Vero Cells (CR +, Fc ɣR −) due to wild type ACE2 IgG chimeric mAb (Human ACE2 /Angiotensin-Converting Enzyme 2 Protein 1-740 (hACE2 full length IgG Fc Tag chimeric mAb) Sino Biological Catalog Number 10108-H02H) and live SARS-CoV-2. As the ACE2 IgG Fc chimeric mAb was diluted (log ACE2, mg/ml), there was a slight dose-dependent increase in viral CPE, consistent with C'ADE, as has been demonstrated with Ebola. Since Vero E6 cells lack Fc ɣRs, but express complement receptors, the antibody enhancement observed must be due to C'ADE, highlighting the importance of using IgG Fc silent antibodies for treatment, including prophylaxis, of SARS-CoV-2.

Figure 13:
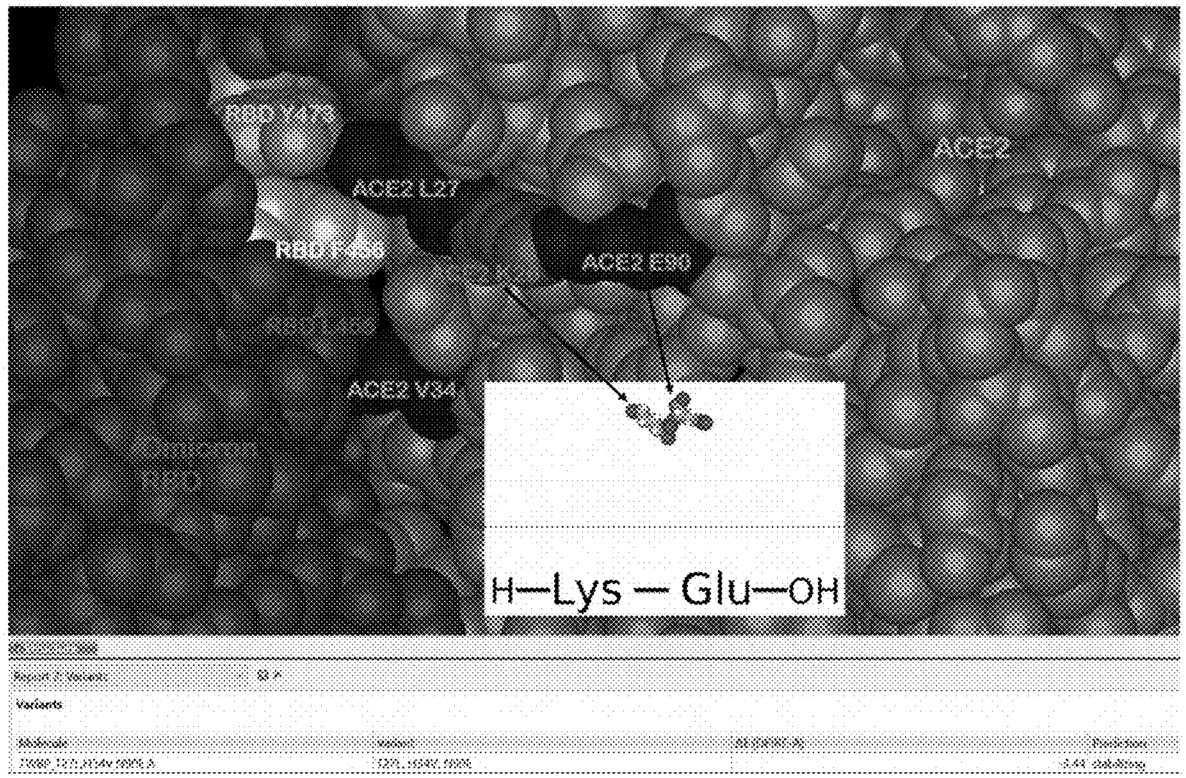

FIG. 13 shows a three-dimensional model of the ACE2/SARS-CoV-2 molecular interface for the ACE2 LVE variant bound to the Omicron variant (PDB 7WBP). Unexpectedly, in the model, the N90E mutation causes a hydrogen bond to form between ACE2 26K and 90E (a Lys26-Glu90 H bond), which further stabilizes ACE2 27L and the interaction between ACE2 27L and Omicron RBD residues Y473 and F456, as shown in FIG. 13. There is also a structural rearrangement in the Omicron variant of RBD 417, which allows for a closer interaction between ACE2 34V and Omicron RBD L455. These changes may contribute to the observed high binding affinity of the ACE2 LVE IgG Fc STR ("LiVE") and ACE2 LVE IgG Fc STR YTE ("LiVE Longer") chimeric antibodies for the Omicron SARS-CoV-2 variant spike protein trimer. Modeling was done as described in Example 1.

Figure 14:
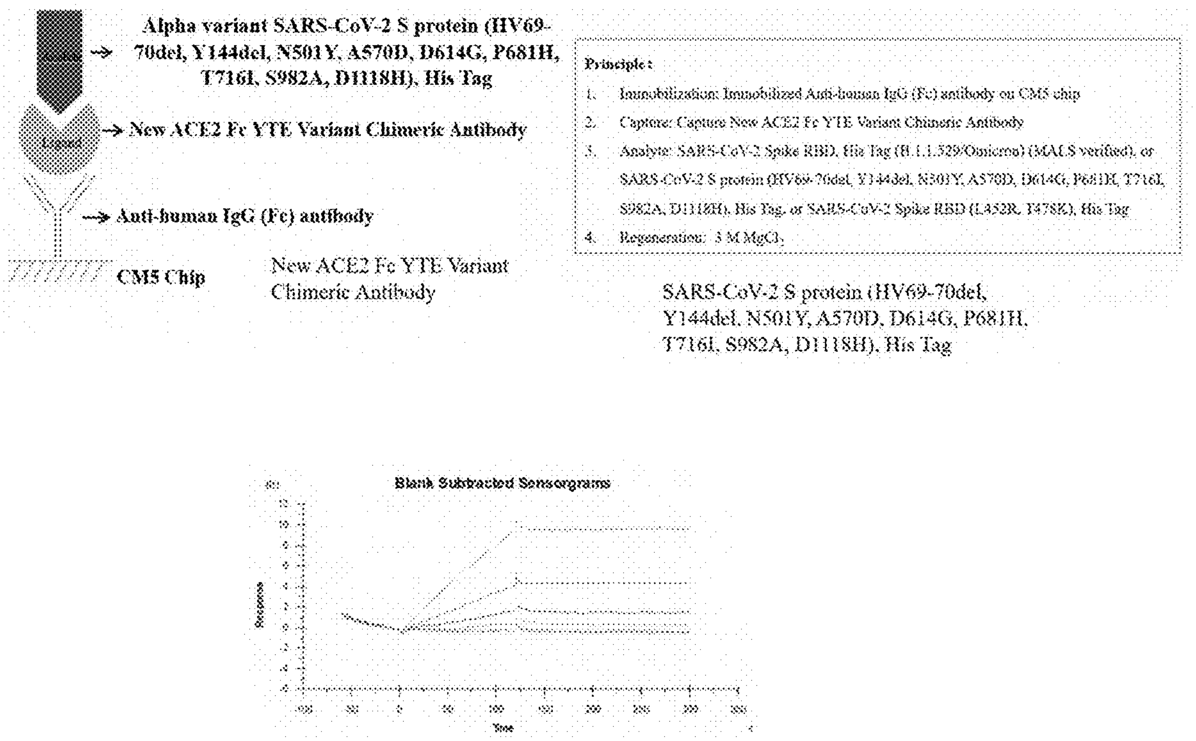

FIG. 14 provides the actual binding affinity data for the ACE2 YVE IgG Fc STR YTE antibody against the SARS-CoV-2 Alpha spike protein 51 (ACRO Biosystems Cat. No. SPN-052H6) (BIACore SPR analysis performed by ACRO Biosystems).

Figure 15:
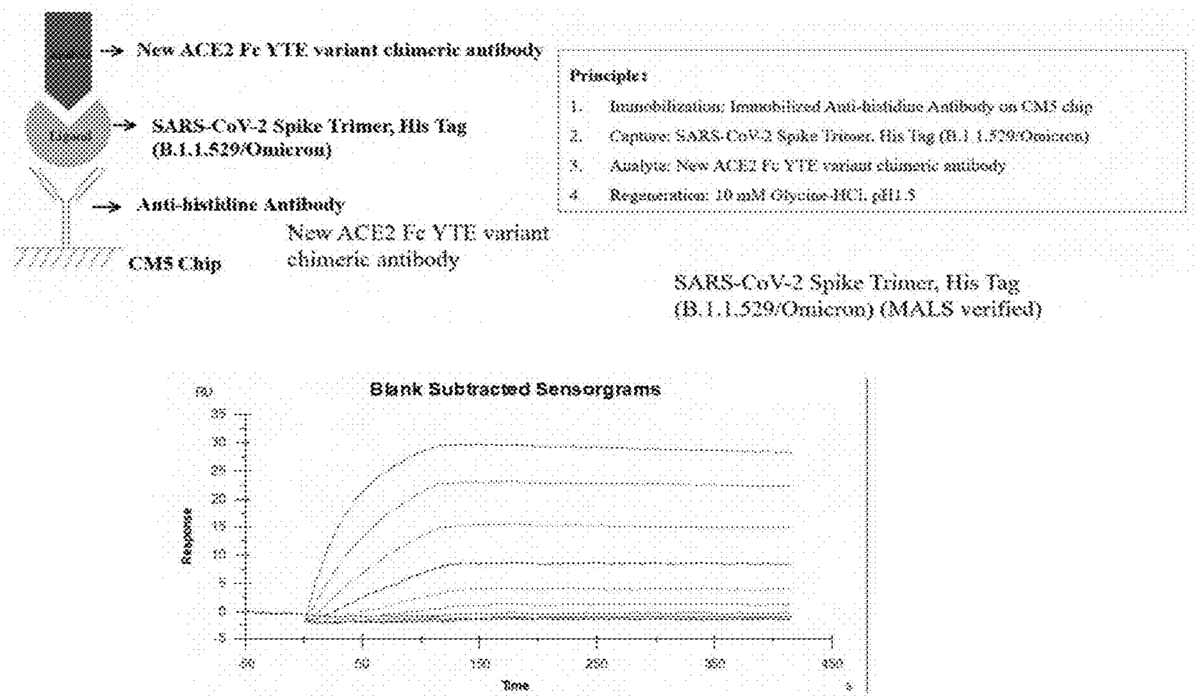

FIG. 15 provides the actual binding affinity data for the ACE2 YVE IgG Fc STR YTE variant against the Omicron spike protein trimer (ACRO Biosystems SPN-052Hz) (BIA-Core SPR analysis performed by ACRO Biosystems).

Figure 16:
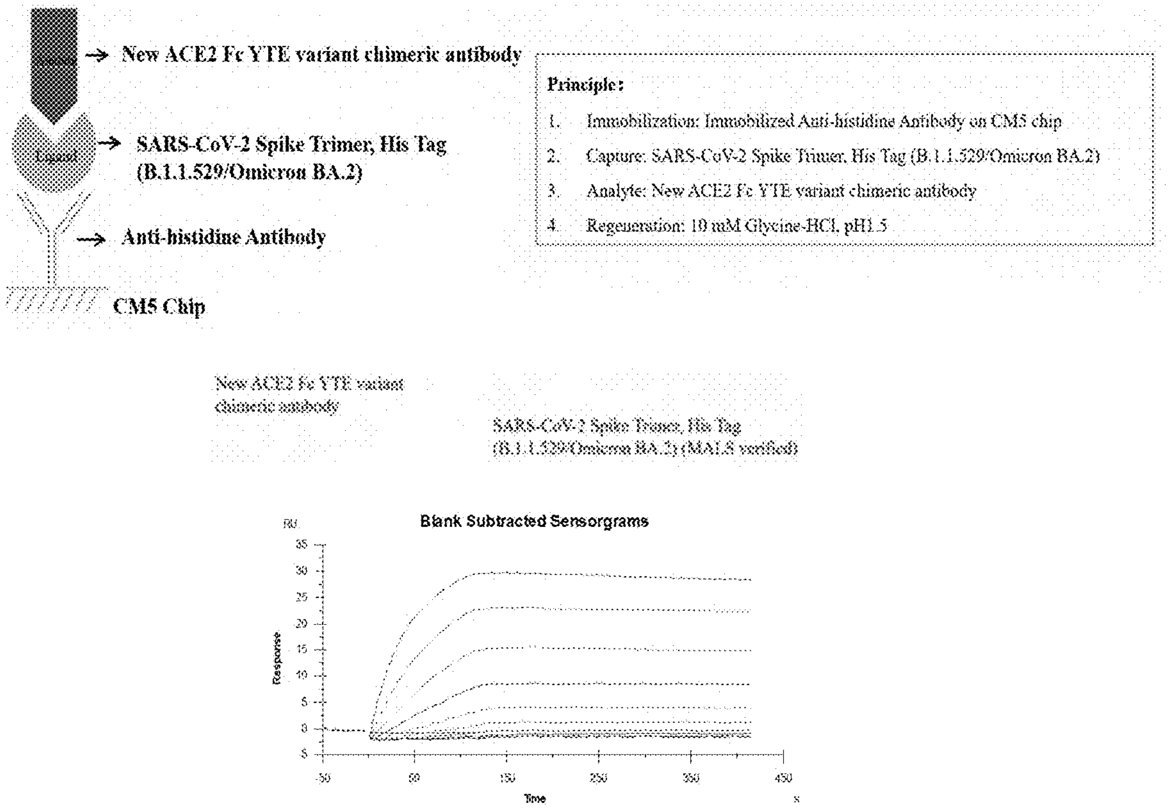

FIG. 16 provides the actual binding affinity data for the ACE2 LVE IgG Fc STR YTE ("LiVE Longer") variant against the Omicron BA.2 spike protein trimer (ACRO Biosystems SPN-05223) (BIACore SPR analysis performed by ACRO Biosystems for "B.1.1.529/Omicron BA.2", as described in Example 4). This Omicron BA.2 sub-variant has fueled a world-wide wave of COVID-19. The binding affinity is 72.8 femtomolar—almost a thousand-fold improvement over the binding affinity against the original Omicron variant, Omicron BA.1. This result is the highest binding affinity reported for any anti- SARS-CoV-2 mAb, certainly over a thousand times higher binding affinity than has been reported for any ACE2 chimeric mAb.

Figure 17:
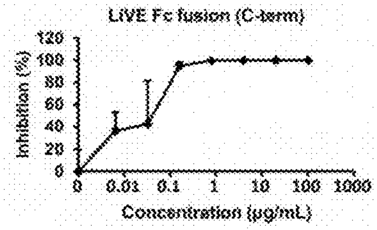
Figure 17:
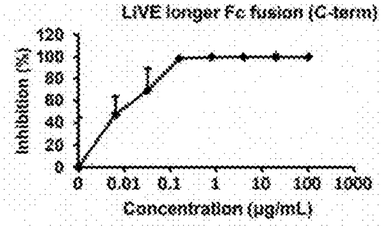

FIG. 17 provides data showing that, consistent with the sVNT and BIACore data, the ACE2 LVE IgG Fc STR YTE ("LiVE Longer") antibody out-performs the ACE2 LVE IgG STR ("LiVE") antibody, insofar as the "LiVE Longer" antibody has almost twice the percentage of neutralization of live SARS-CoV-2 in human lung organoids as the "LiVE" antibody.

Figure 18:
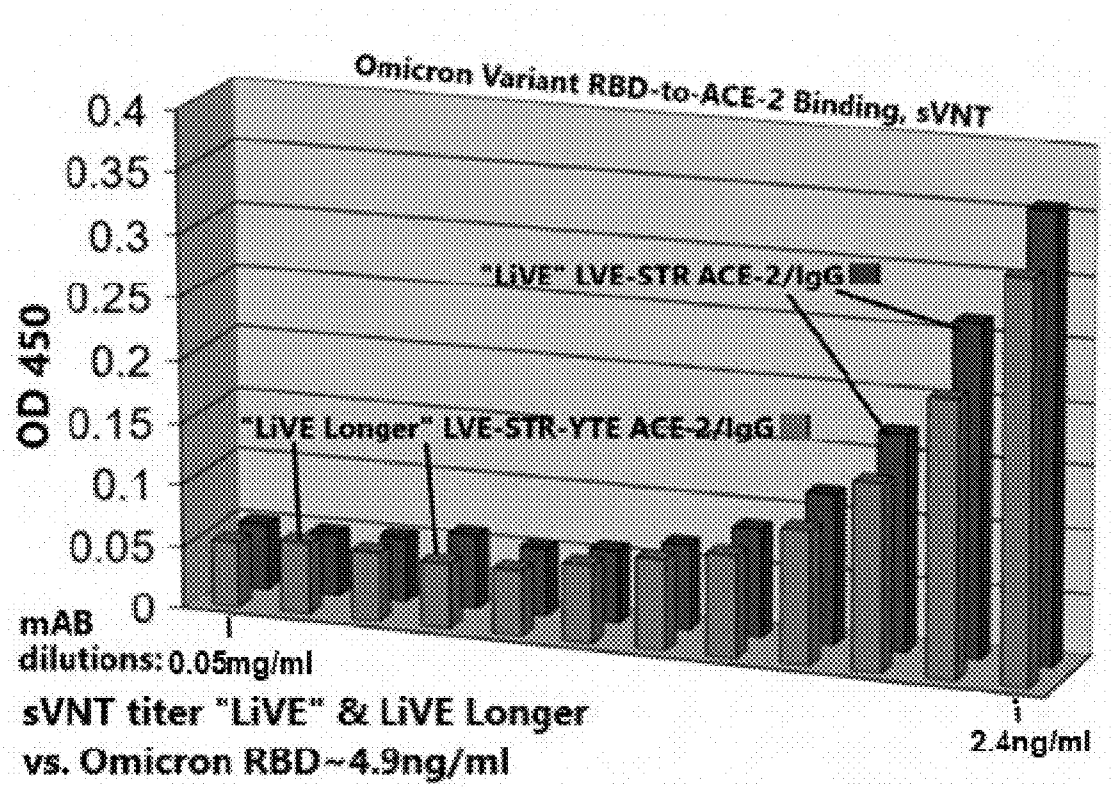
Figure 18:
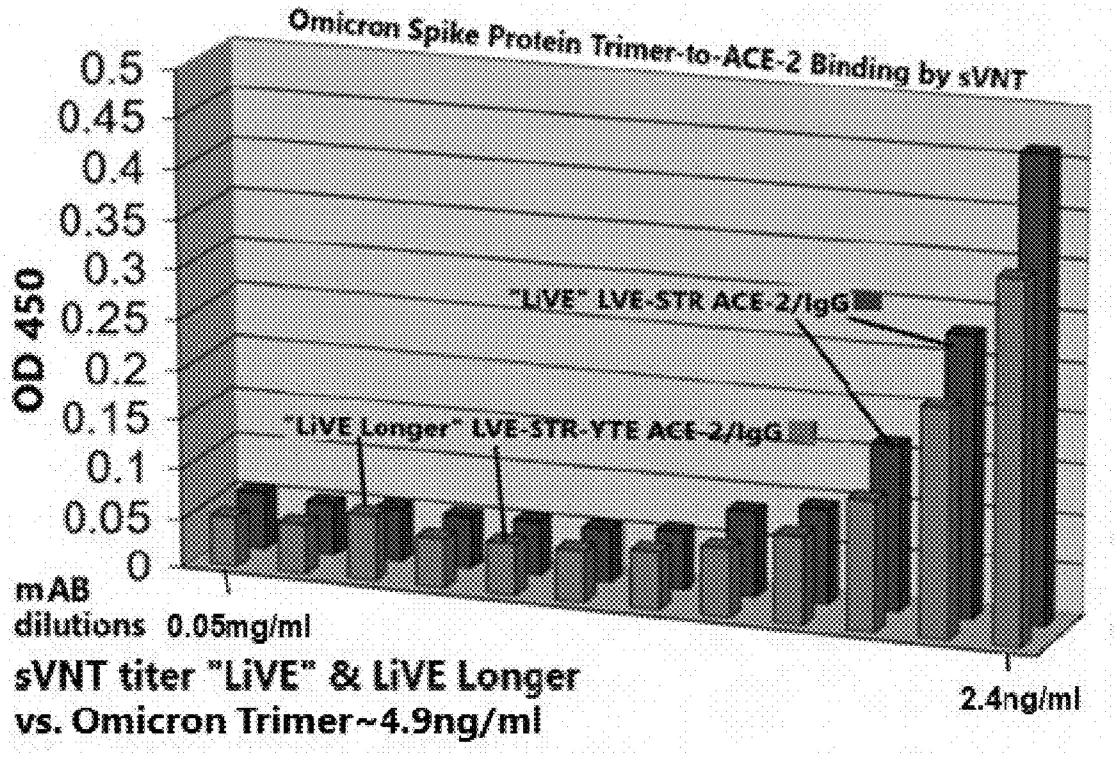

FIG. 18 shows results as presented in FIGS. 5 and 6 for the Omicron variant sequence B.1.1.529 (described in FIG. 3E), but indicates dilutions as concentrations (0.05 mg/ml to 2.4 ng/ml, left to right) instead of ratios. These results show the potential for neutralization of purified recombinant RBD (top panel) or purified spike protein trimer (bottom panel) by the "LiVE" (back row, blue) and "LiVE Longer" (front row, green) chimeras. For both chimeras, sVNT titers were ~4.9 ng/ml for neutralization of Omicron RBD or Omicron spike trimers, but there was slightly better neutralization by the "LiVE Longer" chimera (front row, green). See FIGS. 1A and 20 for additional details about the ACE2/Fusion protein chimeras.

Figure 19:
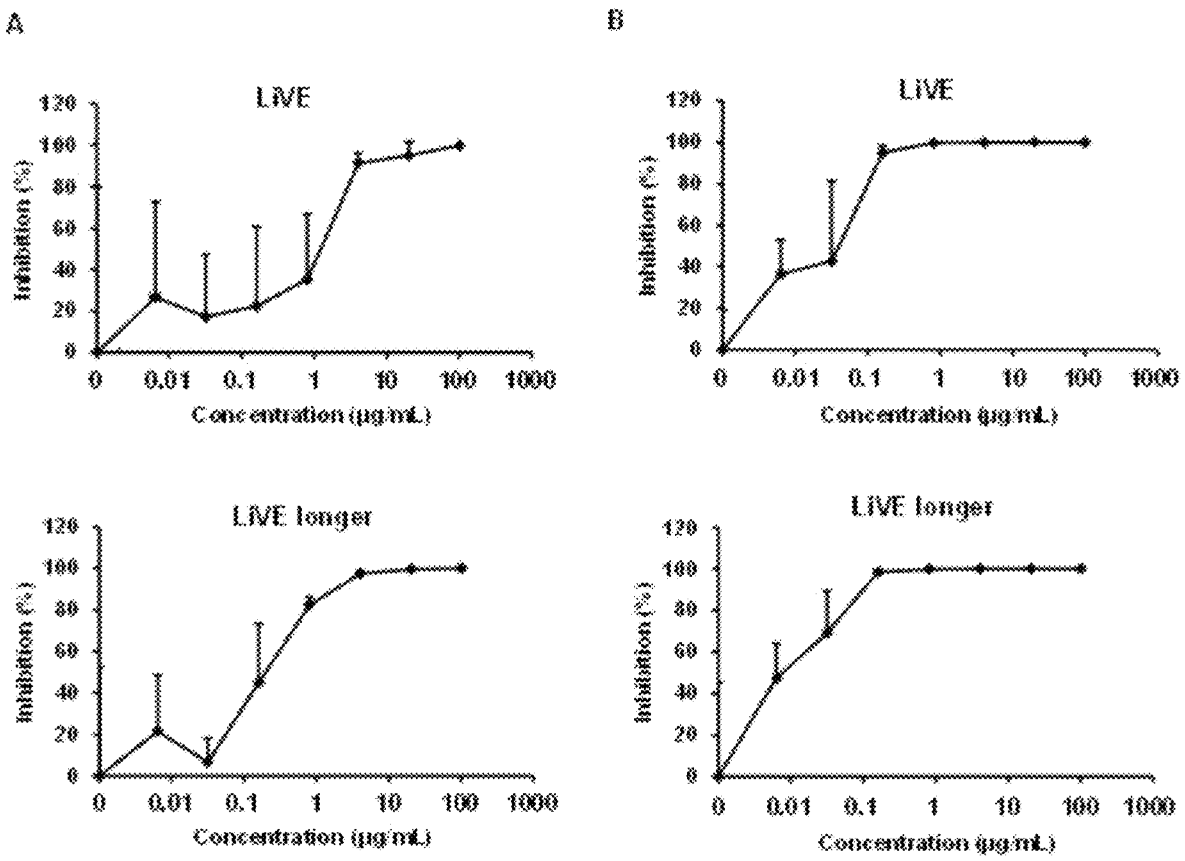

FIG. 19 shows the antiviral effects of "LiVE" and "LiVE Longer" fusion proteins against SARS-CoV-2 B.1.1.214 (A) or Omicron BA.1 (B) infection of human airway organoid cultures. After one day in culture, organoid cultures ($1.0\times10^4$ cells/well) were infected with 0.1 MOI SARS-CoV-2 B.1.1.214 or BA.1 and then cultured with the medium containing a serially diluted antibody for 2 days. The viral RNA copy number in the cell culture supernatant was measured by qPCR. Data are represented as means±SD (n=3).

Figure 20:
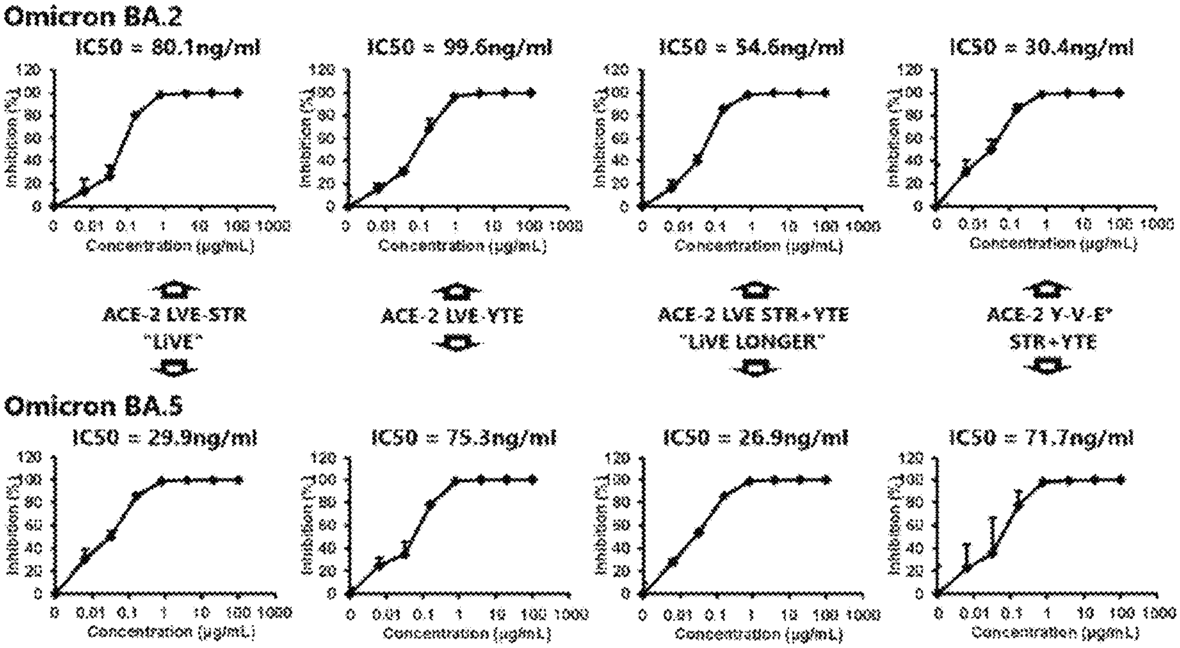

FIG. 20 shows the antiviral effects of the "LiVE", "LiVE Longer" and related chimeric fusion proteins against SARS-CoV-2 Omicron BA.2 or BA.5 infection of human airway organoid cultures. Organoid cultures were exposed to Omicron variants BA.2 (top panels) or BA.5 (bottom panels) and were challenged with the fusion proteins "LiVE" (leftmost pair), "LiVE Longer" (3rd pair from left), modified LiVE without STR (2nd from left) or a modified LiVE Longer with tyrosine substituted for leucine at position 27 (Y-V-E*, rightmost panels). Note the most potent inhibition of Omicron BA.5 replication by the LiVE (IC50=29.9 ng/ml) and LiVE LONGER fusion proteins (IC50=26.9 ng/ml).

Figure 21:
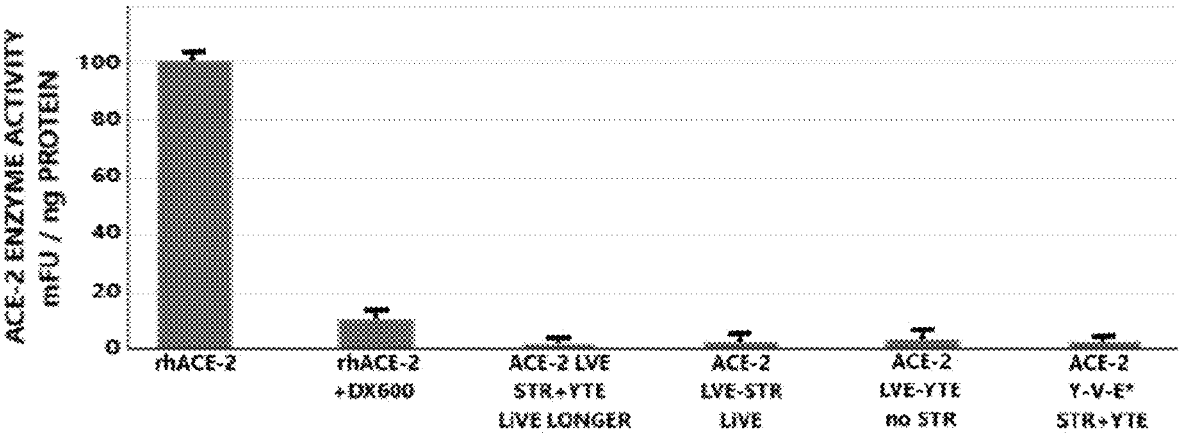

FIG. 21 shows ACE2 enzymatic activity of the chimeric fusion proteins. Equal amounts of recombinant human ACE2 (rhACE2) were subjected to measurements of ACE2 enzyme activity using standard ACE2 enzyme assay methods based on fluorogenic substrate conversion. Results are the mean+/−S.E.M. of eight replicates per group. Note inhibition of ACE2 activity by the competitive inhibitor peptide DX600 (at luM) and the extremely low to negligible activity in any of the chimeric fusion proteins tested.

Figure 22:
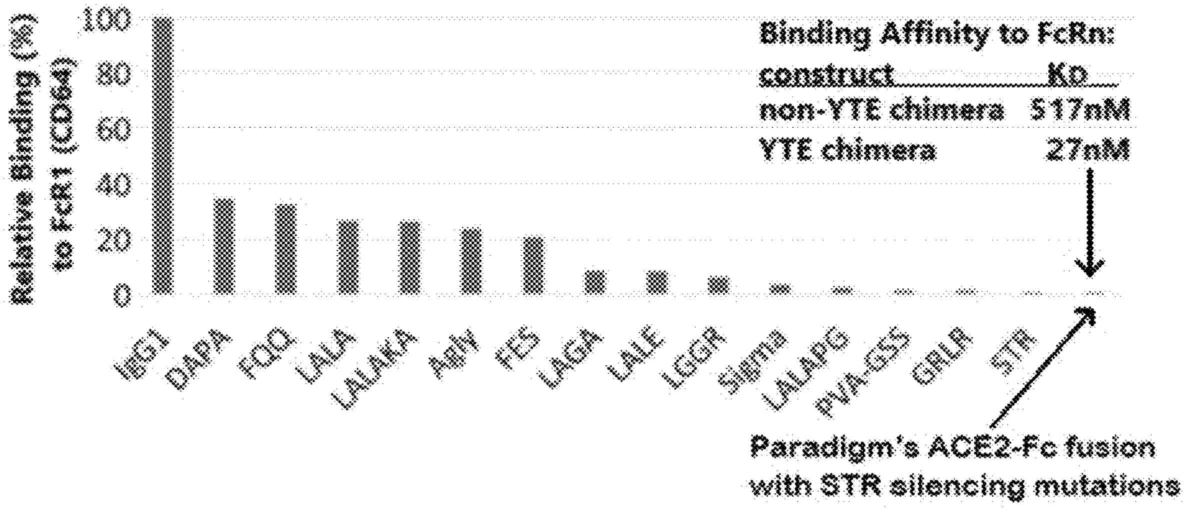

FIG. 22 shows the relative potency of Fc-silencing technologies, determined by Surface Plasmon Resonance (SPR) measurements of the binding of purified, recombinant protein samples of each modified antibody to immobilized recombinant human FcγRI receptor. At the far right, both the Fc-silencing method and mAbsolve's STR silencing methods show the lowest, almost undetectable binding to FcγRI receptor. The inset displays SPR data for binding of either the LiVE (non-YTE) or LiVE-Longer chimeras to purified FcRn receptor. Note high affinity binding of the YTE chimera to FcRn, but not by the non-YTE variant. Binding to FcRn will increase the biological half-life of the chimera in nasal epithelium.

DETAILED DESCRIPTION OF ILLUSTRATIVE EMBODIMENTS

Disclosed herein are compositions and methods to prevent and/or treat respiratory infections, including but not limited to SARS-CoV-2, the causative agent of COVID-19. The compositions and methods can include chimeric ACE2-IgG antibodies comprising an Fc region and two Fab arms, wherein one or both of the Fab arms are substituted with functional ACE2 enzymatic polypeptide(s) that bind to SARS-CoV-2.

The chimeric ACE2-IgG antibodies include those having sequences and/or variants as disclosed herein; it is understood, however, that the sequences provided herein may vary to some degree without parting from the spirit and scope of the disclosure. Thus, an amino acid sequence disclosed herein includes sequences having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity thereto. An amino acid sequence disclosed herein also includes sequences having the same variations disclosed herein and similar sequences (e.g., having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity). An amino acid sequence disclosed herein also includes sequences having the same variations disclosed herein and similar sequences (e.g., having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) near such variation either sequentially or spatially in the antibody, for example, within 5, 6, 7, 8, 9, 10, 11, 12, 13, 14, or 15 amino acids of the variation. An amino acid sequence disclosed herein also includes sequences having the same variations disclosed herein and similar sequences (e.g., having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) that have structure and/or functionality as disclosed herein. In some embodiments, variants of the disclosed sequences include conservatively modified variants. Conservatively modified variants are known in the art, as described for example in Lackie, *Dictionary of Cell and Molecular Biology, supra.*

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning—A Laboratory Manual*, Cold Spring Harbor Press 4$^{th}$ Edition (Cold Spring Harbor, N.Y. 2012). As appropriate, procedures involving the use of commercially available kits and reagents are generally carried out in accordance with manufacturer-defined protocols and conditions unless otherwise noted.

Basic texts disclosing the general terms in molecular biology and genetics include, e.g., Lackie, *Dictionary of Cell and Molecular Biology*, Elsevier (5th ed. 2013). Basic texts disclosing methods in recombinant genetics and molecular biology include, e.g., Sambrook 2012, supra, and *Current Protocols in Molecular Biology* Volumes 1-3, John Wiley & Sons, Inc. (1994-1998) and Supplements 1-115 (1987-2016). Basic texts disclosing the general methods and terms in biochemistry include, e.g., Lehninger Principles of Biochemistry sixth edition, David L. Nelson and Michael M. Cox eds. W. H. Freeman (2012). Basic texts disclosing general methods and terms in immunology include, e.g., *Janeways Immunobiology* (Ninth Edition) by Kenneth M. Murphy and Casey Weaver (2017) Garland Science; and *Fundamental Immunology* (Seventh Edition) by William E. Paul (2013) Lippincott, Williams and Wilkins.

SARS-CoV-2 and COVID

SARS-CoV-2 has caused the pandemic Coronavirus Disease 2019 (COVID-19), a highly infectious and often fatal disease that affects the lungs and other organs. The COVID-19 pandemic has beens the greatest public health emergency that the world has faced since the 1918 influenza pandemic. It has been estimated that, barring pharmaceutical intervention, there have been or could be between 1.1-2.2 million deaths due to COVID-19 in the United States and long-term impacts on human health are also expected to be substantial.

SARS-CoV-2 belongs to the large coronavirus (CoV) family, which are enveloped viruses that have a 26-32 kb, positive-sense, single-stranded RNA genome. The viral envelope consists of a lipid bilayer where the viral membrane (M), envelope (E) and spike (S) structural proteins are anchored. The S protein, also known as the viral fusion protein, specifically interacts with its primary receptor, the angiotensin-converting enzyme 2 (ACE2) on the cell surface, to mediate virus-cell fusion, resulting in viral infection through mechanisms thought to be similar to those for SARS-CoV-1. The viral S protein binds to its primary receptor ACE2 through the Receptor Binding Domain (RBD) of the S subunit. A subset of the viral mutations that differentiate variants of SARS-CoV-2 occurs in the RBD portion of the S-subunit and thereby affects binding affinity to the viral receptor. In general, mutations that increase binding affinity of the RBD to ACE2 result in higher infectivity, but other factors such as immune evasion also play important roles in SARS-CoV-2 virulence.

Definitions

The term “ACE2 (Gln18-Ser740) UniProt Accession #Q9BYF1” as used herein refers to SEQ ID NO: 9, which is a truncated version of UniProt Accession #Q9BYF1, provided here as SEQ ID NO: 1. SEQ ID NO: 9 has a 17 amino acid N-terminal deletion and a 65 amino acid C-terminal deletion relative to SEQ ID NO: 1. When referring to “ACE2 (Gln18-Ser740) UniProt Accession #Q9BYF1” variants, the amino acid numbering is with reference to the full length ACE2 sequence according to SEQ ID NO: 1. A person of skill in the art is readily able to identify the corresponding location of the mutations in SEQ ID NO: 9.

As used here, the terms “LVE” and “ACE2 LVE” refer to and encompass any ACE2 variant, e.g. a variant of SEQ ID NO: 1 or SEQ ID NO: 9, having 27L, 34V, and 90E. As used herein, the terms “YVE” and “ACE2 YVE” refer to and encompass any ACE2 variant, e.g., a variant of SEQ ID NO: 1 or SEQ ID NO: 9, having 27Y, 34V, and 90E.

The terms “IgG Fc 234S, 235T, 236R variant” and “IgG Fc STR” as used herein refer to SEQ ID NO 7. SEQ ID NO: 7 has 234S, 235T, and 236R. As used herein, the terms “Fe STR” and “STR” refer to and encompass any immunoglobulin variant having 234S, 235T, 236R.

The term “IgG Fc STR YTE” as used herein refers to SEQ ID NO: 8. SEQ ID NO: 8 has 234S, 235T, and 236R and further has 252Y, 254T, and 256E. As used herein, the terms “Fe YTE” and “YTE” refer to and encompass any immunoglobulin variant having 252Y, 254T, and 256E.

When referring to an Fc region comprising variants or particular amino acids, for example, 234S, 235T, and 236R (e.g., as in SEQ ID NO: 7) or 252Y, 254T, 256E (e.g., as in SEQ ID NO: 8), the amino acid numbering is with reference to the full length Fc sequence shown as SEQ ID NO: 6. A person of skill in the art is readily able to identify the corresponding locations in SEQ ID NO: 7 or SEQ ID NO: 8 having the recited mutations.

The terms “ACE2 LVE STR chimeric antibody,” “ACE2 LVE IgG Fc STR,” and “LiVE,” as used herein, refers to SEQ ID NO: 2 or any substantially similar chimeric antibody having ACE2 LVE and Fc STR.

The terms “ACE2 LVE STR YTE chimeric antibody,” “ACE2 LVE IgG Fc STR YTE” and “LiVE Longer” refers to SEQ ID NO: 4 or any substantially similar chimeric antibody having ACE2 LVE, Fc STR, and Fc YTE.

The terms “ACE2 YVE STR chimeric antibody” and “ACE2 YVE IgG Fc STR” as used herein refers to SEQ ID NO: 3 or any substantially similar chimeric antibody having ACE2 YVE and Fc STR.

The terms “ACE2 YVE STR YTE chimeric antibody,” and “ACE2 YVE IgG Fc STR YTE” as used herein refers to SEQ ID NO: 5 or any substantially similar chimeric antibody having ACE2 YVE and Fc STR.

The term “sequence identity” as used herein refers to similarity of amino acid sequences as determined by BLAST algorithm or a substantially similar method of analysis.

The term “composition” or “formulation” as used herein refers to a mixture of two or more compounds, elements, or molecules. For example, as used herein, a “composition” or “formulation” may comprise a mixture of one or more active agents with a pharmaceutically acceptable vehicle or excipients to provide a pharmaceutical formulation.

The term "therapeutically effective amount," or "effective amount," as used herein, refers to the amount of a composition that produces the desired effect for which it is administered. The term "therapeutically effective amount," includes that amount of a chimeric antibody or composition comprising a chimeric antibody that, when administered, is sufficient to prevent development of, or alleviate at least to some extent, one or more of the signs or symptoms of the disorder or disease (e.g., COVID-19) being treated. The effective amount will vary depending on the composition, the disease and its severity, and the age, weight, etc., of the subject being treated. The exact amount will depend on the purpose of the treatment, which may be therapeutic or prophylactic, and will be ascertainable by one skilled in the art using known techniques, as described, for example, in Lloyd (1999), "The Art, Science and Technology of Pharmaceutical Compounding."

As used herein, the terms "treatment" or "treating" relate to preventing or curing or substantially preventing or curing a condition, as well as ameliorating at least one symptom of the condition, and are inclusive of prophylactic treatment and therapeutic treatment. Accordingly, the terms "treatment" or "treating" include but are not limited to: inhibiting the progression of a disease or condition of interest, e.g., a respiratory viral infection and/or related health condition; reducing the severity of the condition or disease; ameliorating or relieving symptoms of the condition or disease; causing a regression of one or more of the symptoms associated with the condition or disease; and/or preventing or reducing the risk of occurrence of a condition or disease.

A "pharmaceutically acceptable carrier" (also referred to herein as an "excipient") is a pharmaceutically acceptable solvent, suspending agent, or any other pharmacologically inert vehicle for delivering one or more therapeutic compounds (e.g., a polypeptide/immunoglobulin) to a subject. Pharmaceutically acceptable carriers can be liquid or solid and can be selected with the planned manner of administration in mind to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids or whole proteins include, by way of example and not limitation: water; saline solution; hypochlorous acid, binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Therapeutic Challenges for Treatment of COVID-19

One of the main types of pharmaceutical biologic interventions that are likely to lead to a reduction in morbidity and mortality in the COVID-19 pandemic are antibodies and vaccines against SARS-CoV-2.

Unfortunately, existing antibodies lack efficacy against evolving variants. Several antibodies have been granted Emergency Use Authorization (EUA) by the US FDA for clinical use, including: 1) bamlanivimab plus etesevimab, which comprises neutralizing mAbs that bind to different, but overlapping, epitopes in the spike protein RBD; 2) casirivimab plus imdevimab (REGEN-COV), which comprises recombinant human mAbs that bind to nonoverlapping epitopes of the spike protein RBD; 3) tixagevimab plus cilgavimab (Evusheld), which comprises recombinant human anti-SARS-CoV-2 mAbs that bind nonoverlapping epitopes of the spike protein RBD, and 4) sotrovimab, which targets an epitope in the RBD that is conserved between SARS-CoV and SARS-CoV-2.

Antibodies previously approved for emergency use against SARS-CoV-2 have been shown to have significantly lower neutralizing capacity for the Omicron variant compared to previously dominant variants. On Jan. 24, 2022, the FDA revoked the Emergency Use Authorization (EUA) for casirivimab plus imdevimab (REGEN-COV) due to a lack of efficacy against the Omicron variant. On Feb. 2, 2022, the FDA revoked EUA for bamlanivimab plus etesevimab. Although sotrovimab (Xevudy) was thought to retain significant capacity to neutralize the initial Omicron variants, the FDA revoked the EUA for sotrovimab on Apr. 5, 2022, due to loss of efficacy against Omicron variant BA.2. On Nov. 30, 2022, the FDA announced that bebtelovimab was not authorized for emergency use because it would not neutralize the Omicron subvariants BQ.1 and BQ.1.1

As announced on Feb. 23, 2022, the efficacy of tixagevimab plus cilgavimab (EvusheldTM) for the Omicron variant was reduced to the point of requiring a doubling of the dose to combat the Omicron VOC. The NIH also warned on Dec. 1, 2022, that Omicron subvariants (namely, BA.4.6, BA.2.75.2, BA.5.2.6, BF.7, BQ.1 BQ.1.1 and XBB*) are resistant to tixagevimab plus cilgavimab, as explained by Wang et al., "Resistance of SARS-CoV-2 Omicron Subvariant BA.4.6 to Antibody Neutralization," 2022 (bioRxiv preprint doi: doi.org/10.1101/2022.09.05.506628), incorporated herein by reference. Tixagevimab plus cilgavimab is escaped by mutations at SARS-CoV-2 RBD R346, including R346T, R346S and R346I mutations. On Jan. 6, 2023, the FDA released important information about risk of COVID-19 due to certain variants not neutralized by Evusheld, warning that the "FDA does not anticipate that Evusheld will neutralize XBB.1.5" (www.fda.gov/drugs/drug-safety-and-availability/fda-releases-important-information-about-risk-covid-19-due-certain-variants-not-neutralized-evusheld). As of Jan.14, 2023, CDC COVID Data Tracker: Variant Proportions (covid.cdc.gov/covid-data-tracker/#variant-proportions) showed that XBB.1.5 made up ~43% of all U.S. COVID Omicron subvariants and >80% of COVID Omicron subvariants in the Northeast (HHS Regions 1 & 2 supra).

Some mutated ACE2 mimics have shown improved binding to the viral RBD and enhanced affinity for viral variants. But while these engineered ACE2 mimics may have higher affinity binding to the SARS-CoV-2 RBD than to wild-type ACE2, the binding affinities are relatively low, e.g., nanomolar or low, sub-nanomolar binding affinities.

Existing antibody therapeutics also do not address the occurrence of antibody-dependent enhancement (ADE) of infection, including complement mediated antibody-dependent enhancement (C'ADE or C-ADE), intrinsic antibody-dependent enhancement (iADE), antibody-dependent inflammation (ADI), and the like, which are discussed in more detail below. In ADE, non-neutralizing or sub-neutralizing antibodies against viral surface proteins, e.g., generated or administered during a previous infection, can promote the subsequent entry of viruses into the cell, e.g. during a secondary infection, and thereby intensify the ensuing inflammatory process. For example, antibodies may facilitate viral entry into FcγR expressing host cells, ultimately leading to an enhancement of infection. This process has been observed for a range of diseases, including dengue fever, Zika virus (ZIKV), Ebola virus, human immunodeficiency virus (HIV), Aleutian mink disease parvovirus, Coxsackie B virus, influenza, and SARS.

Enhancement of disease due to pre-existing antibodies is a central issue regarding treatment of COVID-19 using antibodies or vaccines. With respect to respiratory infections, ADE is included in a broader category named enhanced respiratory disease (ERD), which describes severe clinical presentations of respiratory viral infections associated with medical interventions (especially vaccines and prophylactics). ERD and ADE, in particular ADI, are increasingly being recognized as a serious danger in COVID-19. Generally, COVID-19 and ADE, and other forms of ERD, are characterized by excessive inflammation. Antibody dependent inflammation (ADI) has been documented in COVID-19 infections and may be induced by anti-spike IgG. ERD can be associated with a broad range of molecular mechanisms, including FcɣR-dependent antibody activity and complement activation (C'ADE), and other antibody-independent mechanisms such as tissue cell death, cytokine release and/or local immune cell activation. Activation of complement and activating FcɣRs may contribute to the cytokine storm associated with severe SAS CoV-2 infections. For example, afucosylated IgG Fc has a higher binding affinity to FcγRIII than fucosylated forms, and its use in antibodies used to treat COCID may increase disease severity.

Although severe COVID-19 disease is linked to exuberant inflammation, how SARS-CoV-2 triggers inflammation is not well understood. Monocytes and macrophages are sentinel cells that sense invasive infection to form inflammasomes that activate caspase-1 and gasdermin D (GSDMD), leading to inflammatory death (pyroptosis) and release of potent inflammatory mediators. It is known that about 6% of blood monocytes in COVID-19 patients are infected with SARS-CoV-2. Monocyte infection depends on uptake of antibody-opsonized virus by Fcγ receptors, but vaccine recipient plasma does not promote antibody-dependent monocyte infection. SARS-CoV-2 begins to replicate in monocytes, but infection is aborted, and infectious virus is not detected in infected monocyte culture supernatants. Instead, infected cells undergo inflammatory cell death (pyroptosis) mediated by activation of NLRP3 and AIM2 inflammasomes, caspase-1 and GSDMD. Moreover, tissue-resident macrophages, but not infected epithelial and endothelial cells from COVID-19 lung autopsies, have activated inflammasomes. These findings, taken together, suggest that antibody-mediated SARS-CoV-2 uptake by monocytes/macrophages triggers inflammatory cell death that aborts production of infectious virus, but causes systemic Fc receptor-dependent inflammation that contributes to COVID-19 pathogenesis.

Antibody-Based Therapeutics

The compositions and methods disclosed herein provide an antibody-based therapeutic that treats and/or prevents viral respiratory disease, including COVID-19. The chimeric antibodies have high binding affinities, e.g. in the picomolar or femtomolar range, and can further minimize the potential for development of ADE and other antibody-induced inflammatory processes.

In preferred embodiments, this can be achieved through three technologies.

The first of these leverages information about the naturally occurring receptor protein for a virus to increase binding affinity. For example, SARS-CoV-2 binds to angiotensin-converting enzyme 2 (ACE2) receptors on a cell's surface as a means of invading it. In the chimeric ACE2-Ig antibodies disclosed herein, the Fab portions of the normal antibody are replaced with functional ACE2 enzymatic proteins. The full-length ACE2-IgG molecule was extensively modeled as described in Example 1 using the DNASTAR Lasergene Protean 3-D version 17.3 molecular modeling software (DNASTAR, Inc. 3801 Regent St, Madison, WI 53705), which uses the I-TASSER engine to identify ACE2 variants with significantly higher than normal affinity binding to multiple SARS-CoV-2 variants, including, but not limited to, the Alpha, Beta, Gamma, Delta, and Omicron variants.

The second of these relies upon structural modifications in the Fc region of the Ig to minimize ADE. In preferred embodiments, the antibodies disclosed herein utilize Fc silencing technology, including, but not limited to the IgG Fc STR silencing technology. The mutations can abrogate Fc ɣR binding, including FcγRIIIa/CD16a binding. Without wishing to be bound by theory, mutations that prevent FcɣR binding may counteract the hyperinflammatory process associated with SARS-CoV-2 infections, for example, inflammation caused by abnormal IgG glycosylation. In particular, the presence of the STR variant avoids activation of FcγRIII, an effect that may be due to the influence of the STR variation on glycosylation. They may reduce, ameliorate or eliminate ADE such as ADI and may be useful in treating or preventing Post-Acute Sequelae of COVID-19 (PASC), also known as "Long COVID." This approach to minimizing ADE is broadly applicable. It serves as a platform technology and can be applied to an IgG antibody to mitigate ADE. For example, LALA-P329G/A and/or STR "Fc Silent" IgG antibodies may be incorporated in an intranasal prophylactic or nebulized prophylactic utilizing an IgG mAb, for example, for treatment of respiratory diseases caused by viruses other than SARS-CoV-19, including without limitation RSV and Influenza.

The third of these relies on structure modifications to increase in vivo half-life of the chimeric antibody, for example, by increasing the binding of the chimeric antibody to receptors that occur in tissues that may be infected by a virus. For example, M428L/N434S ("LS") IgG Fc mutations increase the half-life of Sotrovimab. The LS mutations, and other substantially similar mutations, can be incorporated into antibodies to achieve the benefits as described herein associated with increased half-life. Also for example, IgG half-life can be influenced by its binding to FcRn. FcRn is abundantly expressed in the respiratory tract and the intranasal and respiratory pH of 5.5-6.0 favors IgG binding to FcRn. Thus, variations that increase binding of the Ig component of the fusion proteins described herein to FcRn, such as but not limited to YTE, can provide a more efficacious therapeutic, particularly a therapeutic that is administered intranasally and/or in nebulized form.

Developing Variants of Concern

Lineages of SARS-CoV-2 are being tracked and have been cataloged, for example, at The PANGO designation GitHub (available at cov-lineages.org/lineage_list.html). Active lineages are documented, for example, by cov-lineages.org (available at cov-lineages.org /lineage_list.html).

In 2022, several vaccine and monoclonal antibody-resistant SARS-CoV-2 Omicron subvariants began spreading in the United States. The rank of vaccine neutralization evasion observed was in the order of BA.4/5<BF.7≤BA.4.6<BA.2.75.2≤BQ.1.1<XBB.1, as reported in Kurhade, et al., "Low neutralization of SARS-CoV-2 Omicron BA.2.75.2, BQ.1.1 and XBB.1 by parental mRNA vaccine or a BA.5 bivalent booster," Nature Med (2022) (doi.org/10.1038/s41591-022-02162-x) and Wang, et al., "Alarming antibody evasion properties of rising SARS-CoV-2 BQ and XBB subvariants," Cell (2023) (doi.org/10.1016/j.cell2022.12.018).

The amino acid changes occurring in a respiratory virus may inform the design of therapeutic antibodies against it. For example, the BQ.1.1 subvariant has three more substitutions (R346T, K444T, and N460K) in its receptor-binding domain than the parental Omicron subvariant BA.5. The XBB.1 subvariant has nine more changes (G339H, R346T, L3681, V445P, G446S, N460K, F486S, F490S and the wild-type amino acid at position 493) in its receptor-binding domain than its parental BA.2 subvariant. Both Omicron subvariants BQ.1.1 and XBB.1 are completely resistant to therapeutic monoclonal antibodies, including Tixagevimab—Cilgavimab ("Evusheld") and the combination of Bebtelovimab and Sotrovimab, as reported in Imai et al., "Efficacy of Antiviral Agents against Omicron Subvariants BQ.1.1 and XBB," N. Engl. J. Med. 388:89-91 (2023).

Current and future SARS-CoV-2 evolution is a balance between immune evasion and infectivity, which is largely determined by affinity to ACE2, as explained for example by Starr, et al., "Deep Mutation Scanning of SARD-CoV-2 Receptor Binding Domain Reveals Constraints on Folding and ACE2 Binding," Cell 182:1295-1310 (2020), incorporated herein by reference.

The antibodies described herein, having ACE2 variants with higher binding affinity than naturally occurring ACE2 receptors in patients or potential hosts, are particularly effective against both existing and evolving variants. The antibodies described herein anticipate new variants insofar as they include variants that complement observed changes in the virus, e.g., providing conformational changes at the binding interface that accommodate and accentuate the evolving changes in the virus. More generally, as a virus evolves to bind more tightly to a region of its target, the antibody having a mimic region of that target with complementary variations in that region will accordingly also bind more tightly to the virus.

Antibody Enhanced Virulence

It is known for various diseases that patients who have been previously infected by one strain of a virus and who are later infected by another strain can suffer outcomes that are worse than those not previously infected. One explanation for this phenomenon is that differences between two viral serotypes can compromise the ability of antibodies induced by the first infection to neutralize the second one. Instead, the antibodies elicited by the first infection may 'bridge' the second viral strain to antibody constant region (Fc) receptors on immune cells, such as macrophages. Because this bridging is believed to enable viral entry into immune cells, shifting the tropism of the virus, the outcome manifests as an antibody-dependent enhancement (ADE) of infection and a potentially more serious recurrence of disease. This phenomenon is often observed when antibody concentrations decrease because of waning immunity; an antibody may neutralize potently at high concentrations but cause enhancement of infection at sub-neutralizing concentrations.

As can occur for naturally occurring antibodies from prior infection, the use of antibody therapeutics can result in more extreme symptoms of a respiratory disease and can also increase the severity of multiple viral infections, including other respiratory viruses such as respiratory syncytial virus (RSV) and measles.

This can occur via two distinct mechanisms:

First, antibodies can augment virulence by enhanced infection. As discussed above, pathogen-specific antibodies can increase infection by promoting virus uptake and replication in Fcγ receptor-expressing immune cells, for example, as is seen in dengue hemorrhagic virus infection of macrophages. Higher infection rates of target cells occur in an antibody-dependent manner mediated by Fc—FcγR interactions. Dengue virus represents the best documented example of clinical ADE via enhanced infection.

Platelets might be susceptible to activation by anti-SARS-CoV-2 antibodies and might contribute to thrombosis. With SARS-CoV and SARS-CoV-2, in vitro evidence indicates that these non-lymphotropic coronaviruses are unable to productively replicate within hematopoietic cells. Using THP-1 monocyte cells, we found that SARS-CoV-2 did not infect THP-1 monocytes. As shown in FIG. 12, and discussed in Example 10, enhancement of cytopathic effects (CPE) in VERO E6 cells due to complement-ADE (C'ADE) was observed for SARS-CoV-2 using chimeric antibodies having naturally occurring ACE2.

Second, antibodies can enhance virulence by enhanced immune activation. Pathogen-specific antibodies can augment virulence by increased immune activation by Fc-mediated effector functions or immune complex formation, e.g., antibody/antigen complexes (AACs). Enhanced disease and immunopathology are caused by excessive Fc-mediated effector functions and immune complex formation in an antibody-dependent manner. The antibodies associated with enhanced disease are often non-neutralizing. RSV and measles are well-documented examples of ADE caused by enhanced immune activation. In the case of respiratory virus infections, the resulting immune cascade can contribute to lung disease.

Following acute infection with SARS-CoV-2, a significant proportion of individuals develop prolonged symptoms known as Post-Acute COVID-19 Sequelae (PASC). As is known in the art (e.g., Cervia et al., "Immunoglobulin signature predicts risk of post-acute COVID-19 syndrome," Nature Comm 13:446 (2022), FIG. 2*f*, which is incorporated herein by reference), immunoglobulin signature predicts risk of PASC. With the development of new coronavirus variants, sub-neutralizing IgG to an earlier variant, such as the Alpha variant, could exacerbate a infection by a subsequent coronavirus variant, such as the Omicron variant, that became dominant at a later time. Similarly, low neutralizing antibodies can contribute to C'ADE, ADE or immune dysregulation. Thus, the development of new variants of SARS-CoV-2 and the use of antibody-based prophylactics and therapeutics may result in enhancement of disease for COVID patients.

One powerful potential safeguard may involve mutating the Fc-binding domain of the monoclonal antibody to retain its neutralizing potential while preventing uptake in immune cells. There are known mutations that abrogate the binding of antibodies to Fcγ receptors, including LALA (L234A L235A), LALA-PG (L234A L235A P329G), and elimination of the glycosylation site at N297. Notably, introduction of LALA-PG and elimination of the glycosylation binding site have been demonstrated to substantially decrease the effector functions of the Fc region, whereas introduction of the LALA mutation leaves minimal, but sometimes detectable, activity. IgG Fc mutations such as LALA-P329G/A or IgG Fc STR variant antibodies (mAbsolve Limited, Wilton Centre, Redcar Cleveland TS10 4RF UK) can be incorporated into a prophylactic utilizing an IgG mAb. FIG. 11 shows that mAbsolve's Fc Silent technology has less binding to all classes of activating and inhibiting FcγRs (FcγRI, FcγRIIA/b and FcγRIII) as compared to wild type, LALA, LALA-P329G/A, aglycosylated IgG and N297A mutations. Fc effector functions are not required for a prophylactic antibody. Utilizing mAbsolve's "Fc Silent" technology can abolish FcγRII mediated ADE by IgG antibodies or C1q mediated C'ADE.

However, multiple factors appear to be involved in the immunopathogenesis of PASC including persistent SARS-CoV-2 viremia, autoantibodies, and possible reactivation of Epstein-Barr virus viremia. People infected with COVID-19 have more than three times the risk of dying over the following year compared with those who remained uninfected. Short-term mortality (up to 5 weeks post-infection) was significantly higher among COVID-19 patients (1623/10 000) than controls (118/10 000). For COVID-19 cases in patients over 60 years old, increased mortality persisted until the end of the first year after infection, and was related to increased risk for cardiovascular (aHR 2·1, 95%CI 1·8-2·3), cancer (aHR 1·5, 95%CI 1·2-1·9), respiratory system diseases (aHR 1·9, 95%CI 1·2-3·0), and other causes of death (aHR 1·8, 95%CI 1·4-2·2). It is known that SARS-CoV-2 can infect vascular cells and the SARS-CoV-2 spike protein can cause direct endothelial and cardiac damage by down-regulating ACE2.

Since FcRn is widely expressed by endothelial cells, the antibodies disclosed herein can help prevent SARS-CoV-2 infection of vascular cells and by binding to the SARS-CoV-2 spike protein, minimize any immunopathology caused by the downregulation of ACE2. More generally, since the cardiovascular, intestinal, respiratory systems and CNS express high levels of FcRn, the chimeric antibodies described herein may be useful in treating PASC and reducing the excess morbidity and mortality associated with them.

Antibodies disclosed herein may out-compete wild-type convalescent anti- SARS-CoV-2 spike protein 51 IgG or IgA that have been implicated in the immunopathogenesis of PASC. The antibodies disclosed herein could compete with endogenous ACE2 and restore homeostasis by negative feedback by the network hypothesis. The antibodies disclosed herein could help restore homeostasis by resolving or preventing persistent SARS-CoV-2 viremia.

After infection with SARS-CoV-2, most children develop mild and self-limiting symptoms of COVID-19, although severe cases and fatal outcomes have been also reported. However, approximately 3-4 weeks after exposure to SARS-CoV-2, some children develop a hyperinflammatory response resembling Kawasaki disease (KD) and toxic shock syndrome that has been termed multisystem inflammatory syndrome in children (MIS-C). MIS-C has elevated levels of soluble biomarkers associated with recruitment and activation of monocytes and neutrophils, vascular endothelium injury, matrisome activation, gastrointestinal and cardiac involvement, and septic shock. Activation of matrisome, which encompasses proteins associated with the extracellular matrix, including the endothelium, and increased levels of biomarkers indicative of endothelial cell damage in MIS-C mirror what is observed in various vasculitis mediated diseases. The antibodies disclosed herein, by binding to FcRn expressed in vascular endothelium, may be useful in preventing MIS-C in children.

Human Organoid and In Vivo Studies

Human nasal epithelium organoids are an excellent model of SARS-CoV-2 infection, reproducing many of the initial infectious events of COVID-19. In humans, airway epithelial cells highly express the putative SARS-CoV-2 entry receptor, angiotensin-converting enzyme 2 (ACE2) and transmembrane serine proteinase 2 (TMPRSS2), the receptor that the virus uses to prime the S protein (spike protein of SARS-CoV-2). SARS-CoV-2 infection experiments using primary human airway epithelial cells have been found to have cytopathic effects 96 h after the infection. However, primary human airway epithelial cells are expensive and do not proliferate indefinitely.

Several infinitely proliferating cell lines, such as Caco-2, Calu-3, HEK293T, and Huh7 cells have been utilized in SARS-CoV-2 infection experiments. These cell lines do not accurately mimic human physiological conditions and generate low titer of infectious SARS-CoV-2. Despite this limitation, valuable information about the virus infection and replication can be learned from studies using these cell lines. Vero cells infected with SARS-CoV-2 have produced high titers of viral particles. For efficient SARS-CoV-2 research, a cell line, such as Vero cells, that can easily replicate and isolate the virus is essential. These cells were isolated from the kidney epithelial cells of an African green monkey in 1963 and have been shown to not produce interferon (IFN). The IFN deficiency allows SARS-CoV-2 to replicate in Vero cells. Among Vero cell clones, Vero E6 is the most widely used to replicate and isolate SARS-CoV-2.

Organoids are composed of multiple cell types and model the physiological conditions of human organs. Organoids have the ability to self-replicate; they are also suitable models for large-scale screening in drug discovery and disease research. Besides the lung damage caused by pneumonia, SARS-CoV-2 affects several organs like the kidney, liver, and the cardiovascular system. Human bronchial organoids and human lung organoids have been developed for SARS-CoV-2 research.

The complex pathophysiology of a disease can be understood by reproducing tissue-specific and systemic virus—host interactions. While cell lines and organoids are faster systems to study the virus and its interactions inside host cells, these can only reproduce the symptoms of COVID-19 in a specific cell type or organ, respectively. However, the pathology of COVID-19 can be reproduced and observed in a tissue-specific and systemic manner in animal models. Several different animals are being used to study the disease and to test candidate therapeutic compounds.

SARS-CoV-2 VOC, except Omicron, do not bind to murine ACE2, so transgenic mice that express human ACE2 have been used as a mouse model of SARS-CoV-2 infection. Transgenic human ACE2 mice, after SARS-CoV-2 infection, show weight loss, virus replication in the lungs, and interstitial pneumonia. In the search for alternative small animal models, molecular docking studies were performed on the binding between ACE2 of various mammals and the S protein of SARS-CoV-2, with the finding that the Syrian hamster might be suitable. After SARS-CoV-2 infection, Syrian hamsters show rapid breathing, weight loss, and alveolar damage with extensive apoptosis.

Small animals like mice and Syrian hamster are advantageous to study SARS -CoV-2, particularly as they reproduce fast. However, to more faithfully reproduce COVID-19 pathology in humans, larger animal models and primate models are preferred. SARS-CoV-2 infection of ferrets shows nonlethal acute bronchiolitis in the lungs. Another model that can be used for COVID-19 studies and is currently the closest to humans in pathophysiology, is the primate cynomolgus macaques. In vivo studies using cynomolgus macaques to compare MERS-CoV, SARS-CoV, and SARS-CoV-2 have demonstrated that cynomolgus macaques are an acceptable model of SARS-CoV-2 infection. Although MERS-CoV mainly infected type II pneumocytes, both SARS-CoV and SARS-CoV-2 infect type I and II pneumocytes. After SARS-CoV-2 infection, damage on type I pneumocytes led to pulmonary edema and the formation of hyaline membranes. Thus, cynomolgus macaques can be infected with SARSCoV-2 and reproduce some of the human pathologies of COVID-19. Rhesus macaques have also been used in COVID-19 studies where the therapeutic effects of adenovirus-vectored vaccine, DNA vaccine candidates expressing S protein, and remdesivir treatment were confirmed. While such non-human primate (NHP) models may be best in replicating virus—human host interactions, a major limitation is that the reproduction rate in cynomolgus and rhesus monkeys is relatively slow.

Olfactory Aspects of Disease and Treatment

The virus entry receptor for SARS-CoV-2, angiotensin-converting enzyme 2 (ACE2), is expressed along the entire human respiratory system, thereby accounting for SARS-CoV-2 respiratory tropism.

In the upper airways, and more precisely in the superior-posterior portion of the nasal cavities, resides the olfactory mucosa. This region is where the respiratory tract is in direct contact with the central nervous system (CNS) via olfactory sensory neurons (OSNs), the cilia of which emerge within the nasal cavity and the axons of which project into the olfactory bulb, which communicates with the brain. Loss of smell has been a hallmark of COVID-19 and several respiratory viruses (influenza, endemic human CoVs, and SARS-CoV-1) invade the CNS through the olfactory mucosa via a retrograde route. SARS-CoV-2 may also be neurotropic and capable of invading the CNS through OSNs. As explained by de Melo et al. ("COVID-19—related anosmia is associated with viral persistence and inflammation in human olfactory epithelium and brain infection in hamsters," Sci. Transl. Med., 2021, 13 eabf8396), multiple cell types of the olfactory neuroepithelium are infected during the acute phase of infection with SARS -CoV-2 at the time when loss of smell manifests. SARS-CoV-2 has a tropism for the olfactory mucosa and can persist locally not only a few weeks after general symptoms resolution but also several months in OSNs, up to 6 months after initial diagnosis. Long-lasting olfactory function loss correlates with persistence of both viral infection and inflammation.

Understanding viral loads in tissues of COVID-19 patients is important for prophylatic and treatment strategies, including treatment of associated conditions such as C'ADE and PASC. Detection of SARS-CoV-2 in clinical specimens shows that the highest viral copy number is found in nasal swabs, about 200-fold compared to bronchoalveolar lavage or pharyngeal swabs. In the early stages of SARS-CoV-2 infection, viral RNA is readily detected in upper respiratory specimens, but not in blood, urine, or stool. These findings, taken together with ACE2 protein cellular localization, suggest that SARSCo-V-2 infection and replication occurs in the surfaces of the respiratory system, particularly in the apical layer of nasal and olfactory mucosa.

Administration of the antibodies described herein to human respiratory surfaces may have particular benefits for treatment of respiratory viruses, including SARS-CoV-2. Antibodies as described herein that bind preferentially to a virus, relative to the naturally occurring receptors of humans at risk of infection by the virus, may act as a decoy and prevent infection. For example, chimeric antibodies that are administered to the respiratory tract may preferentially bind a respiratory virus, preventing binding of the respiratory virus to cell surface receptors and consequent infection.

ACE2 Fc fusion proteins as disclosed herein that bind to FcRn may reduce or prevent infection by SARS-CoV-2 of cells that express both ACE2 and FcRn, including ciliated, basal and sustentacular cells in the olfactory neuroepithelium. ACE2 Fc fusion proteins as disclosed herein that are administered intranasally may reduce or prevent infection of the olfactory bulb as well as surrounding areas and respiratory tract. Preventing or reducing SARS-CoV-2 infection may reduce, ameliorate or prevent the symptoms of COVID-19. Preventing or reducing infection of the olfactory bulb may reduce, ameliorate or prevent anosmia and upper respiratory SARS-CoV-2 entry, replication, and invasion of the CNS by SARS-CoV-2 and may reduce, ameliorate or prevent the symptoms of associated disease processes including inflammation, C'ADE and PASC.

The normal pH of the upper respiratory tract is normally acidic, with an average pH of 6.0-6.3. Due to the pH gradient from the upper to lower respiratory tract, FcRn expressed in the upper respiratory tract would be expected to bind any IgG Fc with enhanced FcRn binding affinity, including, but not limited to the IgG Fc YTE or LS variants. Saturating FcRn expressed in the respiratory system with the antibodies disclosed herein may prevent SARS-CoV-2 infections and could create a "virtual mask."

The expression of FcRn in the respiratory epithelia closely correlates with the expression of ACE2, the primary receptor for SARS-CoV-2, and may help facilitate neuro-invasion and infection of the CNS by SARS-CoV-2. Thus, the antibodies disclosed herein that bind to FcRn may be particularly useful to prevent SARS-CoV-2 infection of the respiratory epithelia and CNS involvement by SARS-CoV-2.

Administration of antibodies as disclosed herein comprising an enzymatically functional ACE2 dimer may also help maintain ACE2 homeostasis. Under physiological conditions there is a balance in ACE and ACE2 receptor activity. ACE regulates the Renin Angiotensin Aldosterone system (RAS) and cleaves Ang I to produce Ang II. Ang II is a potent vasoconstrictor and detrimental for endothelial and epithelial function through activating AT1 and AT2 receptors. The counterbalance of the RAS/Ang II output is regulated by ACE2 and MAS/G protein-coupled receptor activity. ACE2 cleaves Ang I and Ang II into Ang-1-9 and Ang1-7, respectively, and thereby activates MAS/G protein coupled receptors that protect cell death. SARS-CoV-2 binds to ACE2 to gain entry to epithelial cells of the lungs. Cleavage of spike proteins by a protease such as trypsin/cathepsin G and/or ADAM17 on ectodomain sites, and TMPRSS2 on endodomain sites, facilitates viral entry into the cells. This process leads to a down-regulation of host ACE2 receptors and loss of its protective function. Loss of function of ACE2 activity prevents production of Ang 1-9 and Ang1-7. Lack of Ang1-7 diminishes the activity of MAS/G receptor, leading to the loss of its protective functions including vasodilatation and cell protection, both at the epithelial and endothelial sites. Loss of ACE2 function leads to an imbalance and unchecked effects of Ang II and upregulation of RAS/Ang II pathway. Upregulation of Ang II leads to vasoconstriction, thrombophilia, micro thrombosis, alveolar epithelial injury, and respiratory failure.

Therapeutic administration of antibodies as disclosed herein comprising an enzymatically functional ACE2 may prevent upregulation of Ang II, thereby reducing, ameliorating or preventing vasoconstriction, thrombophilia, micro thrombosis, alveolar epithelial injury, and respiratory failure.

Administration of therapeutic antibodies may have particular importance for treatment of elderly, immunocompromised and other patients having increased risk of disease progression or severity. Viral replication in the respiratory tract typically results in viral shedding in mucus. Viral shedding in COVID-19 patients up to 60 days after onset of symptoms has been demonstrated. Such prolonged viral RNA shedding was mainly observed in elderly patients, who may be at higher risk of comorbidities. In immunocompromised patients, persistent viral shedding and positive PCR with cycle thresholds (Ct's) of 30 have been reported. Such "at-risk" patients are particularly in need of and would benefit from the chimeric fusion antibodies disclosed herein.

Administration of the antibodies described herein may facilitate population-level control of disease spread. Intranasal administration may further facilitate such control. Although wearing a mask is generally associated with lower incidence of SARS-CoV-2 and other respiratory infections, compliance to mask wearing in many populations (e.g. in certain areas of the United States) is low. Part of this non-compliance may be ideological, but part of this non-compliance is due to long term discomfort while wearing an N95 or equivalent mask for extended periods of time. For many individuals, compliance may be higher for a nasal spray or aerosol administered antibody therapeutic, or for a periodically administered dosage (e.g. injection) than for use of masks. Prophylactic administration of antibodies as described herein, for example, intranasally or as a periodic (e.g. every 3-6 months) injection, may help prevent the spread of respiratory viruses such as SARS-CoV-2.

Immunoglobulins

The immunoglobulins make up a class of proteins found in plasma and other bodily fluids that exhibit antibody activity and bind to other molecules (e.g., foreign or self-substances or antigens and certain cell surface receptors) with a high degree of specificity. Based on their structure and biological activity, immunoglobulins can be divided into five classes: IgM, IgG, IgA, IgD, and IgE. IgG is the most abundant antibody class in the body; this molecule assumes a twisted "Y" shape configuration. Except for IgM and IgA, immunoglobulins are composed mainly of four peptide chains that are linked by several intrachain and interchain disulfide bonds. For example, the IgGs are composed of two polypeptide heavy chains (H chains) and two polypeptide light chains (L chains), which are coupled by disulfide bonds and non-covalent bonds to form a protein molecule with a molecular weight of approximately 150,000 daltons. The average IgG molecule contains approximately 4.5 interchain disulfide bonds and approximately 12 intrachain disulfide bonds.

The light and heavy chains of immunoglobulin molecules are composed of constant regions and variable regions. For example, the light chains of an IgG1 molecule each contain a variable domain (VL) and a constant domain (CL). The heavy chains each have four domains: an amino terminal variable domain (VH), followed by three constant domains (CH1, CH2, and the carboxyl terminal CH3). A hinge region corresponds to a flexible junction between the CH1 and CH2 domains. Papain digestion of an intact IgG molecule results in proteolytic cleavage at the hinge and produces an Fc fragment (or "region") that contains the CH2 and CH3 domains, and two identical Fab fragments that each contain a CH1, CL, VH, and VL domain. The Fc fragment binds complement and has tissue binding activity, while the Fab fragments have antigen-binding activity.

Immunoglobulin molecules can interact with other polypeptides through various regions. Most of the antigen binding, for example, occurs through the VL/VH region of the Fab fragment. The hinge region also is thought to be important, as crystal structures of IgG/FcγR have shown that the Fc receptors (e.g. for FcγR) are found in the hinge region of IgG molecules.

In the case of some immunoglobulin chimeric proteins, such as etanercept, the Fab arms have been replaced with another protein, such as human TNFR. Entirely human chimeric mAbs such as etanercept lack the CDRs (Complementarity-Determining Regions) of conventional mAbs, which produce anti-idiotypic anti-drug antibodies and fully human chimeric IgG antibodies, such as those disclosed herein, may produce less anti-drug antibodies.

With SARS-CoV-2 vaccination or infection, anti-idiotypic antibodies could have the mirror image to the SARS-CoV-2 RBD and could conceivably generate anti-ACE2 antibodies. The fully human chimeric ACE2 IgG antibodies disclosed herein that are IgG Fc silent may act as decoys for any anti-idiotypic ACE2 antibodies that are generated by either SARS-CoV-2 vaccination or infection.

Immunoglobulin molecules also can interact with other polypeptides through an inter-domain region within the CH2-CH3 domains of the Fc region. The "CH2-CH3 region" typically includes the amino acids at positions 251-255 within the CH2 domain and the amino acids at positions 424-436 within the CH3 domain. As used herein, numbering is with respect to an intact IgG molecule. The corresponding amino acids in other immunoglobulin classes can be readily determined by those of ordinary skill in the art.

The CH2-CH3 region is unusual in that it is characterized by both a high degree of solvent accessibility and a predominantly hydrophobic character, suggesting that burial of an exposed hydrophobic surface is an important driving force behind binding at this site. A three-dimensional change may occur at the IgG CH2-CH3 region upon antigen binding, allowing certain residues (e.g., a histidine at position 435) to become exposed and available for binding.

The Fc region, which comprises the CH2-CH3 region, can bind to several effector molecules and other proteins, including the following:

(1) FcRn. The neonatal Fc receptor (FcRn) determines the half-life of an antibody molecule in the general circulation. Mice genetically lacking FcRn are protected from the deleterious effects of pathogenic autoantibodies due to the shortened half-life of the autoantibodies. The only binding site of FcRn to the IgG Fc is the IgG Fc CH2-CH3 region and HIS 435 has been shown by 3D structure and alanine scan to be essential for binding of FcRn and IgG Fc. Antibodies described herein that bind with high affinity to the CH2-CH3 region and HIS 435 are direct inhibitors of (antibody/antigen complexed) IgG Fc to FcRn binding. An inhibitor of FcRn binding to antibody/antigen complexes or to pathogenic autoantibodies is useful in treating diseases involving pathogenic autoantibodies and/or antibody/antigen complexes.

(2) FcγR. The cellular Fc Receptor (FcγR) provides a link between the humoral immune response and cell-mediated effector systems. The Fcγ Receptors are specific for IgG molecules, and include FcγRI, FcγRIIa, FcγRIIb/c, and FcγRIIIa/b (and alleles, phenotypes and genotypes thereof). These isotypes bind with differing affinities to monomeric and immune-complexed IgG.

(3) C1q. The first component of the classical complement pathway is C1, which exists in blood serum as a complex of three proteins, C1q, C1r, and C1s. The classical complement pathway is activated when C1q binds to the Fc regions of antigen-bound IgG or IgM. Although the binding of C1q to a single Fc region is weak, C1q can form tight bonds to a cluster of Fc regions, such as IgG oligomers, particularly IgG hexamers. At this point C1 becomes proteolytically active.

(4) IgG Fc to IgG Fc interactions. When an IgG molecule binds to an antigen, six IgG molecules form hexamers, as shown for example in Diebolder et al., Science 343(6176) 1260-3 (2014) FIG. 1A, which is incorporated herein by reference. The residues involved in IgG hexamer formation overlap the binding site for FcRn in the CH2-CH3 region and are not affected by the IgG Fc STR variant "Fc Silent" IgG antibody technology since the STR variant (234S, 235T, 236R) does not affect IgG Fc to IgG Fc hexamer formation or FcRn binding, as explained in Wilkinson et al., "Fe-engineered antibodies with immune effector functions completely abolished and STR Data File," PLoS ONE 16(12) e0260954 (2021), incorporated herein by reference in its entirety.

The formation of antibody/antigen complexes via interactions between immunoglobulin Fc regions and other antibodies or other factors (e.g., those described above) is referred to herein as "Fc-mediated antibody/antigen complex formation" or "the Fc-mediated formation of an antibody/antigen complex." Antibody/antigen complexes containing such interactions are termed "Fc-mediated antibody/antigen complexes." Fc-mediated antibody/antigen complexes can include immunoglobulin molecules with or without bound antigen, and typically include CH2-CH3 region-specific ligands that have higher binding affinity for antibody/antigen complexed antibodies than for monomeric antibodies.

Purified Polypeptides

As used herein, a "polypeptide" is any chain of amino acid residues, regardless of post-translational modification (e.g., phosphorylation or glycosylation).

The term "amino acid" refers to natural amino acids, unnatural amino acids, and amino acid analogs, all in their D and L stereoisomers if their structures so allow. Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V). Unnatural amino acids include, but are not limited to 5-Hydroxytryptophan, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3 -diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native polypeptides but differs in composition such that either the C-terminal carboxy group, the N-terminal amino group, or the side-chain functional group has been chemically modified to another functional group. Amino acid analogs include natural and unnatural amino acids which are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring or can be synthetically prepared. Non-limiting examples of amino acid analogs include 5-Hydroxytryptophan (5-HTP), aspartic acid-(beta-methyl ester), an analog of aspartic acid; N-ethylglycine, an analog of glycine; and alanine carboxamide, an analog of alanine. Other examples of amino acids and amino acids analogs, as would be known to a person of skill in the art, are listed in Gross and Meienhofer, The Peptides: Analysis, Synthesis, Biology, Academic Press, Inc., New York (1983).

The stereochemistry of a polypeptide can be described in terms of the topochemical arrangement of the side chains of the amino acid residues about the polypeptide backbone, which is defined by the peptide bonds between the amino acid residues and the a-carbon atoms of the bonded residues. In addition, polypeptide backbones have distinct termini and thus direction. The majority of naturally occurring amino acids are L-amino acids. Naturally occurring polypeptides are largely comprised of L-amino acids.

D-amino acids are the enantiomers of L-amino acids and can form peptides that are herein referred to as "inverso" polypeptides (e.g., peptides corresponding to native peptides but made up of D-amino acids rather than L-amino acids). A "retro" polypeptide is made up of L-amino acids but has an amino acid sequence in which the amino acid residues are assembled in the opposite direction of the native peptide sequence.

"Retro-inverso" modification of naturally occurring polypeptides involves the synthetic assembly of amino acids with α-carbon stereochemistry opposite to that of the corresponding L-amino acids (e.g., D- or D-allo-amino acids), in reverse order with respect to the native polypeptide sequence. A retro-inverso analog thus has reversed termini and reversed direction of peptide bonds, while approximately maintaining the topology of the side chains as in the native peptide sequence. The term "native" refers to any sequence of L-amino acids used as a starting sequence for the preparation of partial or complete retro, inverso or retro-inverso analogs.

Partial retro-inverso polypeptide analogs are polypeptides in which only part of the sequence is reversed and replaced with enantiomeric amino acid residues. Since the retro-inverted portion of such an analog has reversed amino and carboxyl termini, the amino acid residues flanking the retro-inverted portion can be replaced by side-chain-analogous α-substituted geminal-diaminoethanes and malonates, respectively. Alternatively, a polypeptide can be a complete retro-inverso analog, in which the entire sequence is reversed and replaced with D-amino acids.

Preparation and Purification of Polypeptides and Proteins (Immunoglobulins)

Polypeptides can be produced by several methods, many of which are well-known in the art. By way of example and not limitation, a polypeptide can be obtained by extraction from a natural source (e.g., from isolated cells, tissues or bodily fluids), by expression of a recombinant nucleic acid encoding the polypeptide (as, for example, described below), or by chemical synthesis (e.g., by solid-phase synthesis or other methods well known in the art, including synthesis with an ABI peptide synthesizer; Applied Biosystems, Foster City, Calif.). Methods for synthesizing retro-inverso polypeptide analogs (Bonelli et al. (1984) Int. J. Peptide Protein Res. 24:553-556; and Verdini and Viscomi (1985) J. Chem. Soc. Perkin Trans. 1:697-701), and some processes for the solid-phase synthesis of partial retro-inverso peptide analogs also have been described (see, for example, European Patent number EP0097994).

The present disclosure provides isolated nucleic acid molecules encoding the polypeptides described herein. As used herein, "nucleic acid" refers to both RNA and DNA, including cDNA, genomic DNA, and synthetic (e.g., chemically synthesized) DNA. The nucleic acid can be double-stranded or single-stranded (e.g., a sense or an antisense single strand). The term "isolated" as used herein with reference to a nucleic acid refers to a naturally occurring nucleic acid that is not immediately contiguous with both of the sequences with which it is immediately contiguous (one at the 5' end and one at the 3' end) in the naturally occurring genome of the organism from which it is derived. The term "isolated" as used herein with respect to nucleic acids also includes any non-naturally occurring nucleic acid sequence, since such non-naturally occurring sequences are not found in nature and do not have immediately contiguous sequences in a naturally occurring genome.

An isolated nucleic acid can be, for example, a DNA molecule, provided one of the nucleic acid sequences that is normally immediately contiguous with the DNA molecule in a naturally occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The present disclosure also provides vectors containing the nucleic acids described herein. As used herein, a "vector" is a replicon, such as a plasmid, phage, or cosmid, into which another DNA segment can be inserted so as to bring about the replication of the inserted segment. Polypeptides can be developed using phage display, for example. Methods well-known to those skilled in the art may use phage display to develop the polypeptides described herein. The vectors can be, for example, expression vectors in which the nucleotides encode the polypeptides provided herein with an initiator methionine, operably linked to expression control sequences. As used herein, "operably linked" means incorporated into a genetic construct so that expression control sequences effectively control expression of a coding sequence of interest. An "expression control sequence" is a DNA sequence that controls and regulates the transcription and translation of another DNA sequence, and an "expression vector" is a vector that includes expression control sequences, so that a relevant DNA segment incorporated into the vector is transcribed and translated. A coding sequence is "operably linked" and "under the control" of transcriptional and translational control sequences in a cell when RNA polymerase transcribes the coding sequence into mRNA, which then is translated into the protein encoded by the coding sequence.

Methods well-known to those skilled in the art may be used to subclone isolated nucleic acid molecules encoding polypeptides of interest into expression vectors containing relevant coding sequences and appropriate transcriptional/translational control signals. See, for example, Sambrook et al., Molecular Cloning: A Laboratory Manual (2nd edition), Cold Spring Harbor Laboratory, New York (1989); and Ausubel et al., Current Protocols in Molecular Biology, Green Publishing Associates and Wiley Interscience, New York (1989). Expression vectors can be used in a variety of systems (e.g., bacteria, yeast, insect cells, and mammalian cells), as described herein. Examples of suitable expression vectors include, without limitation, plasmids and viral vectors derived from, for example, herpes viruses, retroviruses, vaccinia viruses, adenoviruses, and adeno-associated viruses. A wide variety of suitable expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

Expression vectors that encode the polypeptides described herein can be used to produce the polypeptides. Expression systems that can be used for small or large scale production of polypeptides include, without limitation, microorganisms such as bacteria (e.g., E. coli and B. subtilis) transformed with recombinant bacteriophage DNA, plasmid DNA, or cosmid DNA expression vectors containing the nucleic acid molecules provided herein; yeast (e.g., S. cerevisiae) transformed with recombinant yeast expression vectors containing nucleic acid molecules; insect cell systems infected with recombinant virus expression vectors (e.g., baculovirus) containing the nucleic acid molecules provided herein; plant cell systems infected with recombinant virus expression vectors (e.g., tobacco mosaic virus) or transformed with recombinant plasmid expression vectors (e.g., Ti plasmid) containing the nucleic acid molecules provided herein; or mammalian cell systems (e.g., primary cells or immortalized cell lines such as COS cells, CHO cells, HeLa cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids provided herein.

The term "purified polypeptide" as used herein refers to a polypeptide that either has no naturally occurring counterpart (e.g., a peptidomimetic), or has been chemically synthesized and is thus uncontaminated by other polypeptides, or that has been separated or purified from other cellular components by which it is naturally accompanied (e.g., other cellular proteins, polynucleotides, or cellular components). Typically, the polypeptide is considered "purified" when it is at least 70%, by dry weight, free from the proteins and naturally occurring organic molecules with which it naturally associates. A preparation of purified polypeptide therefore can be, for example, at least 80%, at least 90%, or at least 99%, by dry weight, the polypeptide. Suitable methods for purifying polypeptides can include, for example, affinity chromatography, immunoprecipitation, size exclusion chromatography, and ion exchange chromatography. The extent of purification can be measured by any appropriate method, including but not limited to column chromatography, polyacrylamide gel electrophoresis, or high-performance liquid chromatography.

Antibody Features

Figure 1A:
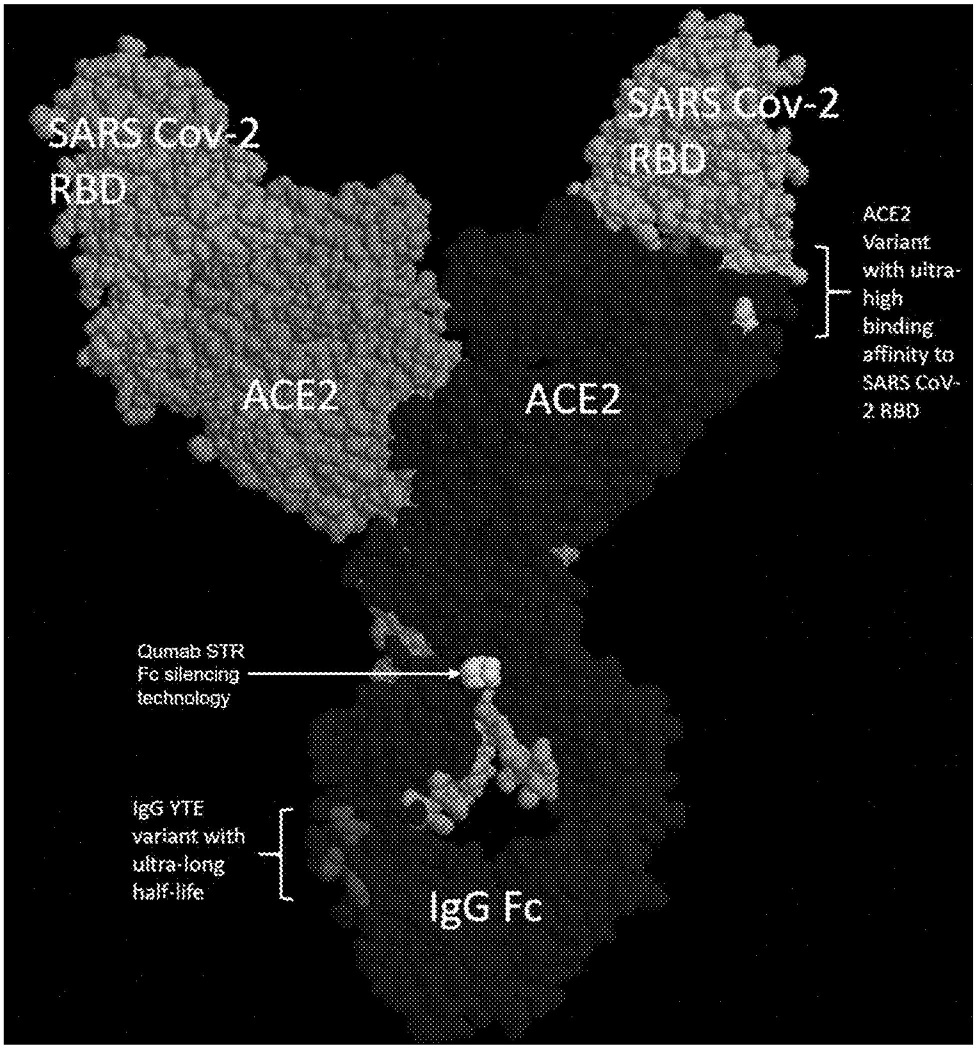
FIG. 1A shows a three-dimensional model of a chimeric antibody ("mAb") having ACE2 variant LVE and IgG Fc variants STR and YTE (LIVE Longer), bound to two SARS-CoV-2 RBDs. The ACE2 (ACE2 (Gln18-Ser740) UniProt Accession # Q9BYF1) variant's mutations T27L (orange), H34V (red) and N90E (light yellow) are shown in the upper right. The IgG Fc variant's silencing mutations 234S, 235T, 236R are shown in yellow near the middle of the image. The IgG Fc variant's Y252, T254, E256 mutations are shown in red, near the bottom left. The ACE2 was similarly linked to an IgG Fc-silent version that did not include the Y252, T254, E256 mutations. Modeling was done as described in Example 1.
Figure 1B:
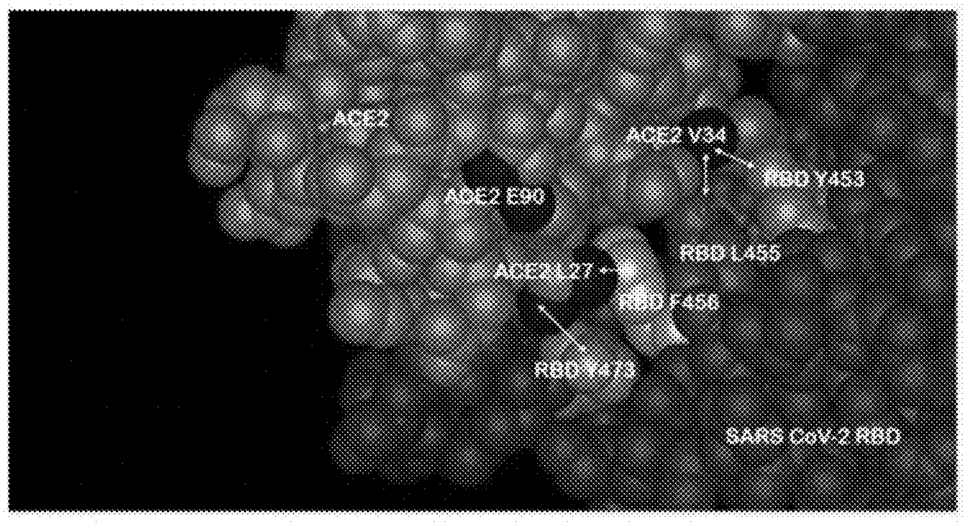
FIG. 1B shows a three-dimensional model of the ACE2/SARS-CoV-2 interface with ACE2 mutations found to impart high binding affinity to the widest range of SARS-CoV-2 variants, including ACE2 amino acid L27 shown interacting with SARS-CoV-2 RBD amino acids Y473 and F456, and ACE2 amino acid V34, which interfaces with the highly conserved SARS-CoV-2 RBD amino acids L455 and Y453. Modeling was done as described in Example 1.
Figure 1C:
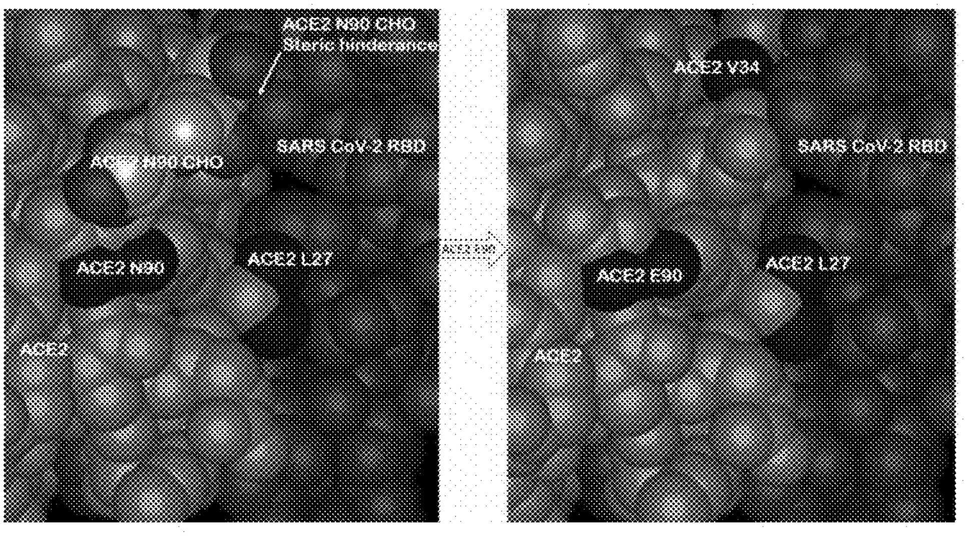
FIG. 1C presents a three-dimensional model that shows the effect of the ACE2 substitution N90E, which eliminates the site for N-linked glycosylation of ACE2 at the ACE2/SARS-CoV-2 interface. Interaction of SARS-CoV-2 with ACE2 having amino acid N90 in its glycosylated form is shown on the left; binding of SARS-CoV-2 to ACE having amino acid E90, without the glycan, is shown on the right. Elimination of the N-linked glycan resulted in higher affinity binding of the ACE2 to several SARS-CoV-2 variants, potentially due to loss of steric hindrance otherwise caused by the glycan. Modeling was done as described in Example 1.
Figure 1D:
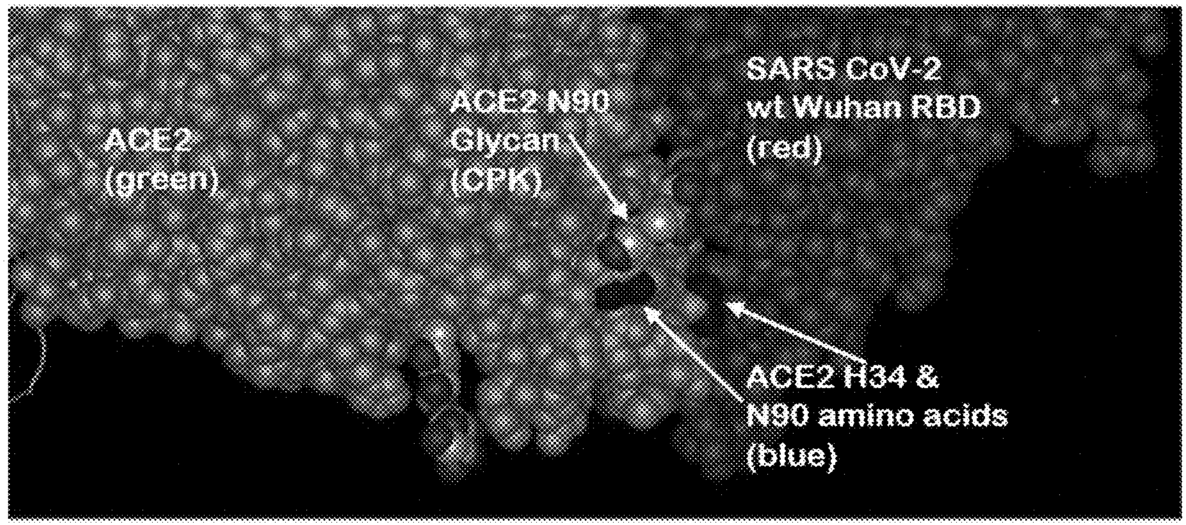
FIG. 1D shows a three-dimensional model of the ACE2/SARS-CoV-2 molecular interface for an ACE2 with an N-linked glycan at amino acid 90 binding to a purified, recombinant wild type (w.t.) SARS-CoV-2 receptor binding domain (RBD) and binding affinity predictions. A similar model was created for ACE2 having YTY at positions 27, 79 and 330, respectively. As indicated, the models indicated stronger binding of the ACE2 LVE variant to the w.t. RBD (DFIRE score -6.67) than that of the ACE2 YTY variant to the w.t. RBD (DFIRE score -4.53) Modeling was done as described in Example 1.
Figure 1E:
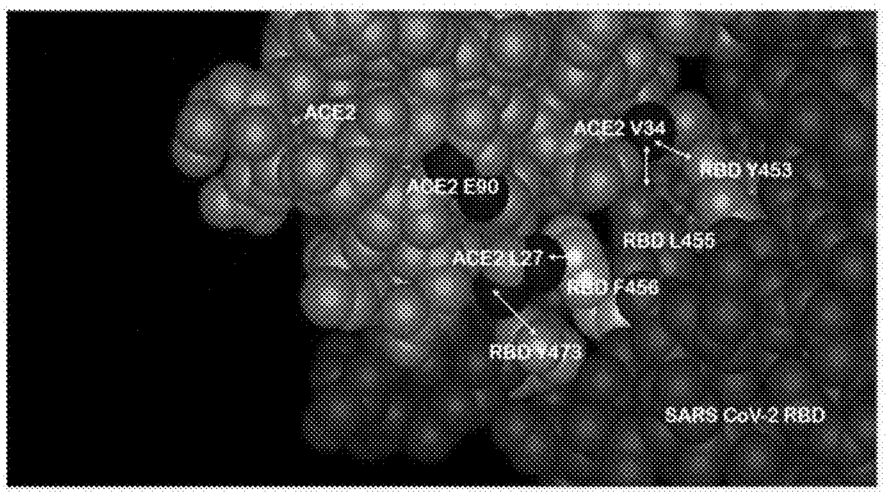
FIG. 1E shows three-dimensional models and binding affinity predictions for the interactions between ACE2 LVE and the RBD of the wild type SARS-CoV-2 variant (top panel), as shown also in FIG. 1B, versus interactions between ACE2 LVE and the RBD of the Delta B.1.617.2 variant (bottom panel). The models indicate stronger binding of the ACE2 LVE variant to the RBD Delta variant (DFIRE score -6.80) than to the w.t. RBD (DFIRE score −6.67). Modeling was done as described in Example 1. Note rotation of RBD F456 (yellow) in Delta variant toward ACE-2 amino acid 27, made permissive by the T27L mutation.
Figure 1E:
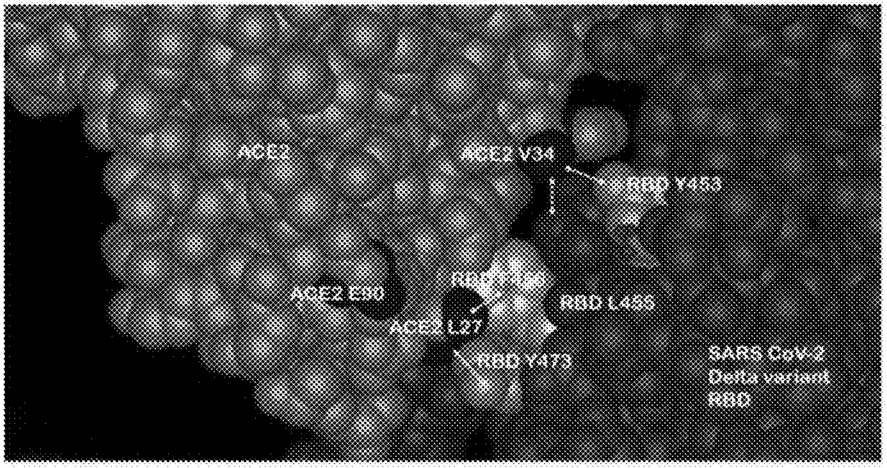
Figure 1F:
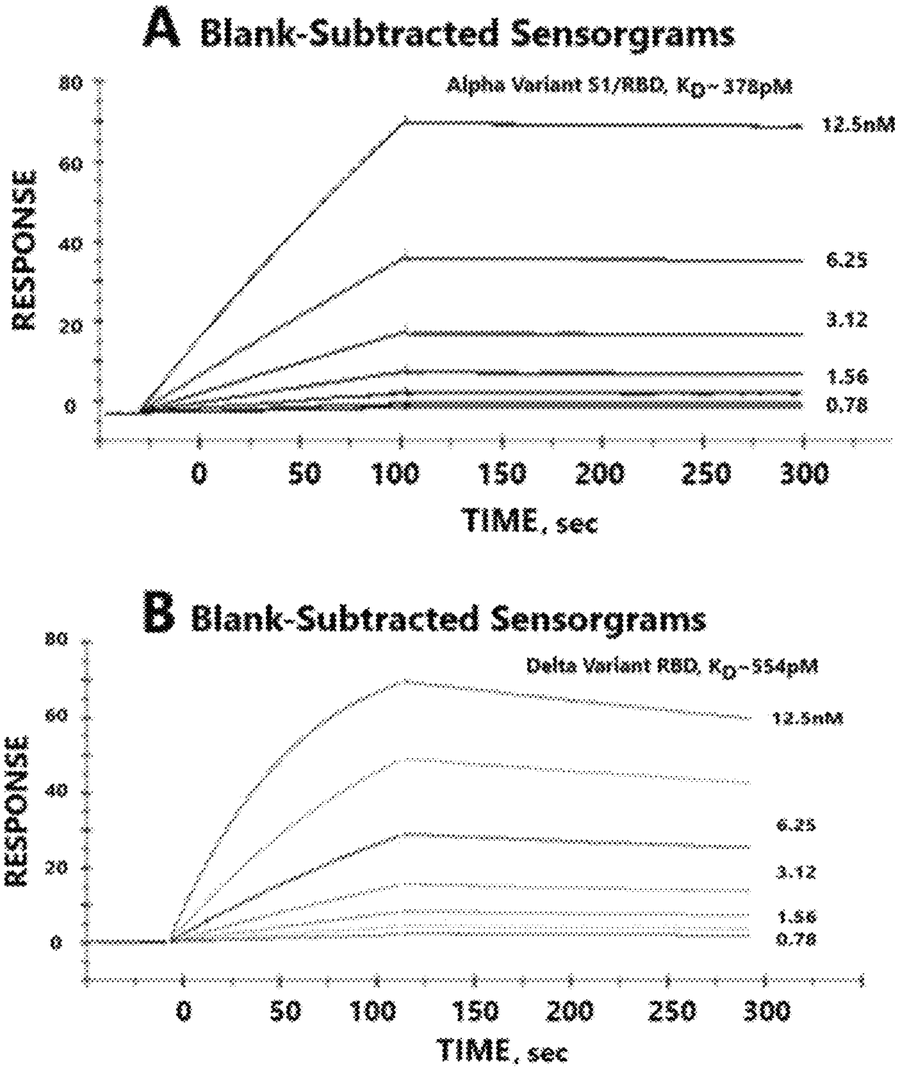
FIG. 1F shows, consistent with the predictions of FIG. 1E, Surface Plasmon Resonance (SPR) data indicating very high binding affinity of the ACE2 LVE to the RBD of the Delta B.1.617.2 variant (554 pM), as well as to the RBD of the Alpha B.1.1.7 variant (378 pM). BIACore SPR analysis was performed by ACRO Biosystems, as described in Example 4.
Figure 2:
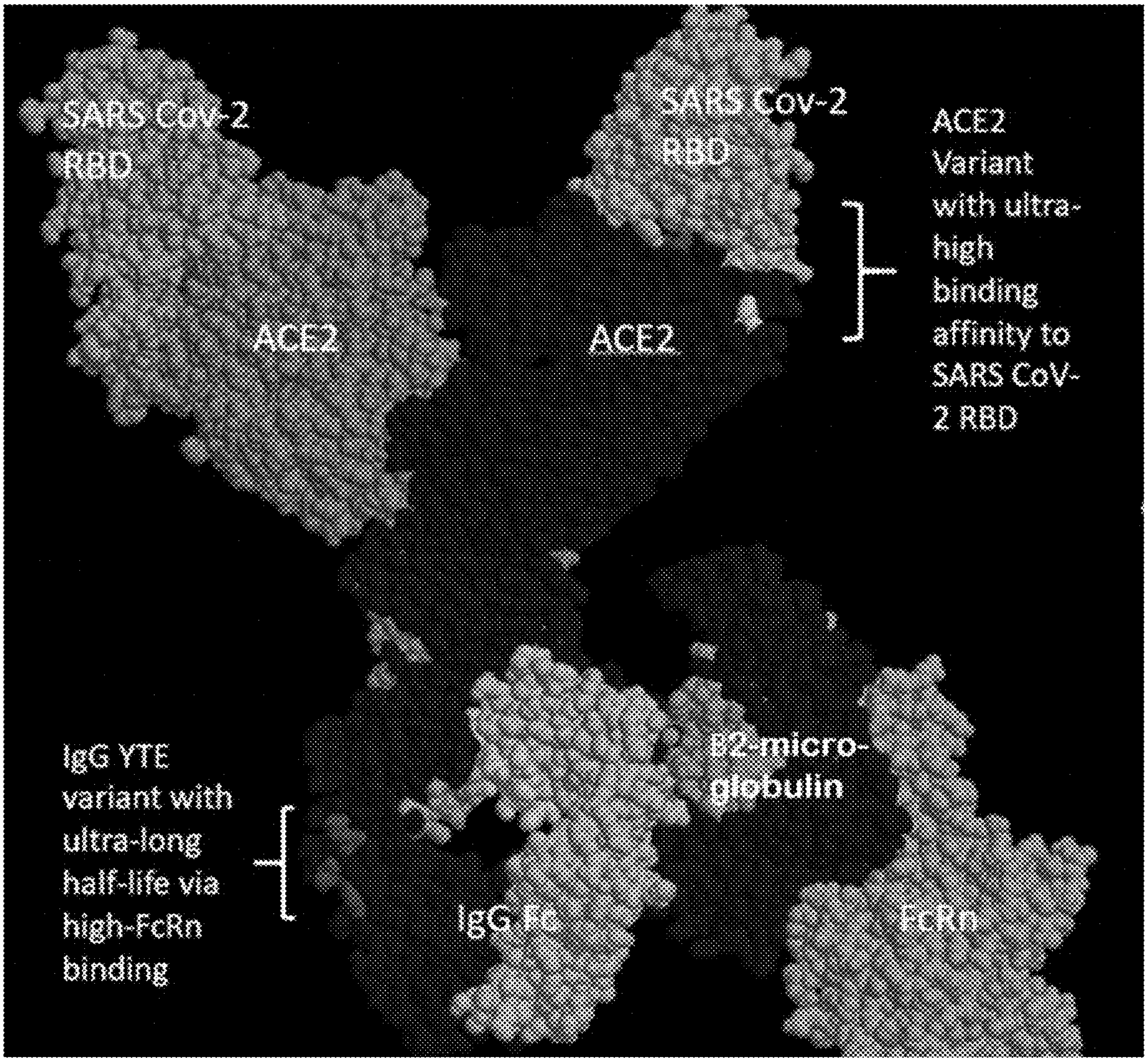
FIG. 2 shows a three-dimensional model of the chimeric antibody having the ACE2 variant LVE and IgG Fc variant YTE, as explained for FIG. 1A, bound to one FcRn (FCGRT UniProt Accession #P55899-1) and one β2-microglobulin (UniProt Accession #P61769-1). The STR mutations (IgG Fc 234S 235T 236R) are included in the model but not highlighted in the image. Modeling was done as described in Example 1.

The antibodies disclosed herein include antibodies having one or more of the following features:

1) Chimeric antibodies including ACE2 (ACE2 (Gln18-Ser740) UniProt Accession # Q9BYF1) variants ACE2 T27L or T27Y, H34V and N90E, as shown in FIGS. 1, 2, and 13. This includes ACE2 Gln18-Ser740, full-length ACE2 1-740, and variants thereof having mutations ACE2 T27L or T27Y, H34V and N90E.

2) Chimeric antibodies, e.g., having ACE2 T27L or T27Y, H34V and N90E, that include variants providing longer half-life due to enhanced binding to FcRn. This may include, for example and without limitation, YTE, LS, DF183, DF197, DF213, DF215 or DF228 IgG Fc mutations.

3) Chimeric antibodies, e.g., having ACE2 T27L or T27Y, H34V and N90E, and optionally including variants providing longer half-life due to enhanced binding to FcRn, that incorporate the IgG Fc 234S 235T 236R STR variant or other "Fc Silent" IgG antibody technology, including, for example, variations that eliminate or reduce binding to FcγRI, FcγRII, FcγRIII or C1q. As discussed above, such variants may negate the possibility of antibody-dependent enhancement and/or inflammatory disease process including ADE, including C'ADE, platelet coagulopathies, extended expression of SARS-CoV-2 spike protein in CD16+ (FcγRIII+) atypical monocytes and/or the hyper-inflammation associated with SARS-CoV-2 infections. The STR variant does not affect IgG Fc to IgG Fc hexamer formation or FcRn binding.

Example of chimeric antibodies that have a combination of Fc silencing technology and increased half-life include but are not limited to: ACE2 T27L/Y, H34V, N90E-STR-YTE, ACE2 27L/Y, 34V, 90E-STR-LS, ACE2 27L/Y, 34V, 90E -"TM" (L234F/L235E/P331S) and "YTE" (M252Y/S254T/T256E), ACE2 27L/Y, 34V, 90E-FQQ-YTE (L234F/L235Q/K322Q/M252Y/S254T/T256E), ACE2 27L/Y, 34V, 90E-LALA-YTE, ACE2 27L/Y, 34V, 90E-LALA-P329G/A-YTE, ACE2 27L/Y, 34V, 90E-TM-LS, ACE2 27L/Y, 34V, 90E-FQQ-LS, ACE2 27L/Y, 34V, 90E-STR-LS variants or any ACE2 T27L/Y H34V N90E Fc silent/extended half-life IgG antibodies.

As described in Example 11, FIG. 13 shows modeling of the LVE (ACE2 T27L H34V N90E) variant bound to the Omicron variant (PDB 7WBP). Unexpectedly, the N90E mutation forms a H bond with ACE2 26K (a Lys26-Glu90 H bond), which further stabilizes T27L (or ACE2 T27Y) and the interaction between ACE2 T27L (or ACE2 T27Y) and Omicron RBD residues Y473 and F456. The structural rearrangement of Omicron RBD 417 allows for a closer interaction between ACE2 H34V and Omicron RBD L455. These changes contribute to the strong (high) binding affinity of the ACE2 LVE chimeric antibodies for the Omicron SARS-CoV-2 variant spike protein trimer.

Interestingly, the ACE2 LVE IgG Fc STR YTE ("LiVE Longer") antibody had higher actual binding affinity (73.4 pM) for the spike protein trimer of the Omicron B.1.1.529 variant than the ACE2 LVE IgG Fc STR ("LiVE") antibody (144 pM). See FIG. 9A vs. FIG. 3E and FIG. 7. The BIACore SPR binding affinities for the "LiVE Longer" variant (with YTE) were thus ~50% higher than the binding affinities for the "LiVE" variant (without YTE). This was surprising since they are identical in the ACE2 LVE variant protein (provided in place of a normal IgG Fab) that binds the SARS-CoV-2 spike protein trimer RBD. The YTE antibody may be forming IgG hexamers more readily than the non-YTE antibody, which could account for the improved performance in the sVNT assay and the BIACore experiments. This property has not been reported for any other IgG antibody having the YTE variant and appears to be unique to the ACE2 LVE IgG Fc STR chimeric antibody having the YTE variant (i.e. "LiVE Longer").

Compositions and Articles of Manufacture

The present disclosure provides compositions and articles of manufacture that can be used in methods for treating diseases and conditions caused by respiratory virus infection, e.g. by SARS-CoV-2, including but not limited to COVID-19 and/or ERD and antibody-dependent conditions such as C'ADE and ADI and conditions that arise from abnormal Fc-mediated antibody/antigen complex formation. The polypeptides/immunoglobulins, compounds, and compositions provided herein can be administered to a subject (e.g., a human, a non-human primate, or another mammal) having or suspected of having, or at risk of having, a respiratory viral infection, to treat and/or prevent one or more diseases or conditions resulting or potentially resulting from infection by the virus. Compositions generally contain one or more antibodies described herein.

In preferred embodiments, the polypeptides/immunoglobulins, compound, or composition is administered in an amount sufficient to treat or prevent infection and/or a consequential condition without triggering antibody-dependent conditions such as ADI and/or C'ADE and conditions that arise from abnormal Fc-mediated antibody/antigen complex formation. The compositions and methods can, for example, modulate Fc-mediated antibody/antigen complex formation and inhibit antibody/antigen complexed IgG Fc binding to mC1q, sC1q, and/or FcγRs. The polypeptides/immunoglobulins and methods described herein can be used to minimize infection or immunoreactivity in a subject at risk for conditions arising from infection by the respiratory virus, including subjects at risk of abnormal or over-production of cytokines, due for example to ADE and/or thrombosis.

Methods for formulating and subsequently administering therapeutic compositions are well known to those skilled in the art. Dosing is generally dependent on the severity and responsiveness of the disease state to be treated, with the course of treatment lasting from several days to several months, or several years until a cure is affected or a prevention or diminution of the disease state is achieved. Persons of ordinary skill in the art routinely determine optimum dosages, dosing methodologies and repetition rates. Optimum dosages can vary depending on the relative potency of individual polypeptides/immunoglobulins and can generally be estimated based on EC50 found to be effective in in vitro and in vivo animal models. Typically, dosage is from 0.01 ug to 100 g per kg of body weight, and can be given once or more daily, biweekly, weekly, monthly, yearly or even less often.

Following successful treatment, it may be desirable to have the patient undergo maintenance therapy to prevent the recurrence of the disease state. Immunocompromised and other at-risk individuals will require chronic (possible lifetime) prophylaxis from SARS-CoV-2 depending on the chronicity of their immunosuppression. Severely immunocompromised individuals, such as multiple myeloma patients or solid organ transplant recipients may require extended prophylaxis against SARS-CoV-2.

The present disclosure provides pharmaceutical compositions and formulations that comprise the polypeptides/immunoglobins described herein. Polypeptides can be admixed, encapsulated, conjugated or otherwise associated with other molecules, molecular structures, or mixtures of compounds such as, for example, liposomes, polyethylene glycol, receptor targeted molecules, or oral, intranasal, rectal, topical or other formulations, for assisting in uptake, distribution and/or absorption.

Pharmaceutical compositions can be administered by several methods, depending upon whether local or systemic treatment is desired and upon the area to be treated. Administration can be, for example, topical (e.g., transdermal, sublingual, ophthalmic, or intranasal); pulmonary (e.g., by inhalation, nebulization or insufflation of powders or aerosols); oral; or parenteral (e.g., by subcutaneous, intrathecal, intraventricular/intravenous, intramuscular, or intraperitoneal injection, or by intravenous drip). Administration can be rapid (e.g., by injection) or can occur over a period of time (e.g., by slow infusion or administration of slow-release formulations). Administration can be recurring, for example, an injection every 1-2, 2-3, 3-6, or 6-12 months, or every 1-2, 3-4, 4-5, or 5-10 years. For treating tissues in the central nervous system, polypeptides/immunoglobulins can be administered by injection or infusion into the cerebrospinal fluid, preferably with one or more agents capable of promoting penetration of the polypeptides/immunoglobulins across the blood-brain barrier or by intra-nasal delivery.

In preferred embodiments, polypeptides/immunoglobulins are administered nasally, e.g., in the form of a nasal spray or swab, or for inhalation, e.g. by nebulization, and a formulation comprises polypeptides/immunoglobulins as disclosed herein in a form suitable for delivery to nasal and/or pulmonary surfaces. The compositions can by delivered with an intranasal delivery device such as a spray container, dropper, or nebulizer.

Formulations for topical administration of polypeptides/immunoglobulins include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays are particularly useful, and can be administered by, for example, a nebulizer or another nasal spray device. Administration by an inhaler also is particularly useful. Conventional pharmaceutical carriers, aqueous, powder or oily bases, thickeners and the like may be necessary or desirable.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration (e.g. injection) can include sterile aqueous solutions, which also can contain buffers, diluents and other suitable additives (e.g., penetration enhancers, carrier compounds and other pharmaceutically acceptable carriers).

Pharmaceutical compositions include, without limitation, solutions, emulsions, aqueous suspensions, hypochlorous acid and self-assembling functionalized or non-functionalized hydrogels or liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including LIPOFECTIN® (a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in membrane-filtered water; Invitrogen/Life Technologies, Carlsbad, Calif.) and EFFECTENE™ (a non-liposomal lipid formulation in conjunction with a DNA-condensing enhancer; Qiagen, Valencia, Calif.).

Polypeptides/immunoglobulins can further encompass any pharmaceutically acceptable salts, esters, or salts of such esters, or any other compound which, upon administration to an animal including a human, is capable of providing (directly or indirectly) the biologically active metabolite or residue thereof. Accordingly, for example, the present disclosure provides pharmaceutically acceptable salts of polypeptides, prodrugs and pharmaceutically acceptable salts of such prodrugs, and other bioequivalents. The term "prodrug" indicates a therapeutic agent that is prepared in an inactive form and is converted to an active form (e.g., drug) within the body or cells thereof by the action of endogenous enzymes or other chemicals and/or conditions. The term "pharmaceutically acceptable salts" refers to physiologically and pharmaceutically acceptable salts of the polypeptides provided herein (e.g., salts that retain the desired biological activity of the parent polypeptide without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hypochlorous acid, hydrochloric acid, hydrobromic acid, sulfuric acid, phosphoric acid, or nitric acid); and salts formed with organic acids (e.g., acetic acid, citric acid, oxalic acid, palmitic acid, or fumaric acid).

Pharmaceutical compositions containing the polypeptides/immunoglobulins provided herein also can incorporate penetration enhancers that promote the efficient delivery of polypeptides, e.g., when applied to a nasal surface. Penetration enhancers can enhance the diffusion of both lipophilic and non-lipophilic drugs across cell membranes. Penetration enhancers can be classified as belonging to one of five broad categories, e.g., surfactants (e.g., sodium lauryl sulfate, polyoxyethylene-9-lauryl ether and polyoxyethylene-20-cetyl ether); fatty acids (e.g., oleic acid, lauric acid, myristic acid, palmitic acid, and stearic acid); bile salts (e.g., cholic acid, dehydrocholic acid, and deoxycholic acid); chelating agents (e.g., disodium ethylenediaminetetraacetate, citric acid, and salicylates); and non-chelating non-surfactants (e.g., unsaturated cyclic ureas). Alternatively, inhibitory polypeptides can be delivered via iontophoresis, which involves a transdermal patch with an electrical charge to "drive" the polypeptide through the dermis.

Some embodiments provided herein include pharmaceutical compositions containing (a) one or more polypeptides/immunoglobulins and (b) one or more other agents that function by a different mechanism. For example, anti-inflammatory drugs, including but not limited to nonsteroidal anti-inflammatory drugs and corticosteroids, and antiviral drugs, including but not limited to ribivirin, vidarabine, acyclovir and ganciclovir, can be included in compositions.

Other non-polypeptide agents (e.g., chemotherapeutic agents) also are within the scope of the present disclosure. Such combined compounds can be used together or sequentially.

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

The pharmaceutical formulations, which can be presented conveniently in unit dosage form, can be prepared according to conventional techniques well-known in the pharmaceutical industry. Such techniques include the step of bringing into association the active ingredients with the desired pharmaceutical carrier(s) or excipient(s). Typically, the formulations can be prepared by uniformly bringing the active ingredients into intimate association with liquid carriers or finely divided solid carriers or both, and then, if necessary, shaping the product. Formulations can be sterilized if desired, provided that the method of sterilization does not interfere with the effectiveness of the polypeptide contained in the formulation.

The compositions described herein can be formulated into any of many possible dosage forms such as, but not limited to, tablets, capsules, liquid syrups, soft gels, suppositories, and enemas. The compositions also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers. Polypeptides/immunoglobulins can be combined with packaging material and sold as kits. Components and methods for producing articles of manufacture are well known. The articles of manufacture can combine one or more of the polypeptides and compounds set out in the above sections.

Non-limiting embodiments of the invention are enumerated as follows:

Embodiment [0001]: Embodiments of the present invention encompass a chimeric ACE2-Immunoglobulin antibody, comprising: an immunoglobulin region having an Fc domain; two Fab arms, wherein at least one of the Fab arms comprises an ACE2 domain, the ACE2 domain comprising at least 90% identity with the amino acid sequences 19-45 and 80-100 of SEQ ID NO: 1 and having substitutions T27L or T27Y, H34V, and N90E (LVE or YVE).

Embodiment [0002]: In some embodiments of the present invention, such as, but not limited to, those described in embodiment [0001], the chimeric ACE2-Immunoglobulin antibody has substitutions T27L, H34V, and N90E (LVE).

Embodiment [0003]: In some embodiments of the present invention, such as, but not limited to, those described in embodiments [0001] and [0002], the Fc domain comprises at least 90% identity with the amino acid sequences 221-251 of SEQ ID NO: 6 and has substitutions L234S, L235T, and G236R (STR).

Embodiment [0004]: In some embodiments of the present invention, such as, but not limited to, those described in embodiments [0001] to [0003], the Fc domain comprises at least 90% identity with the amino acid sequences 237-267 of SEQ ID NO: 6 and has substitutions M252Y, S254T, and T256E (YTE).

Embodiment [0005]: In some embodiments of the present invention, such as, but not limited to, those described in embodiments [0001] to [0004], the Fc domain has greater than 50% sequence identity to SEQ ID NO: 6.

Embodiment [0006]: In some embodiments of the present invention, such as, but not limited to, those described in embodiments [0001] to [0005], the ACE2 domain has greater than 50% sequence identity to SEQ ID NO: 1.

Embodiment [0007]: In some embodiments of the present invention, such as, but not limited to, those described in embodiments [0001] to [0005], the ACE2 domain has greater than 50% sequence identity to SEQ ID NO: 9.

Embodiment [0008]: In some embodiments of the present invention, such as, but not limited to, those described in embodiments [0001] to [0007], the ACE2 domain comprises SEQ ID NO: 11 or SEQ ID NO: 12.

Embodiment [0009]: In some embodiments of the present invention, such as, but not limited to, those described in embodiments [0001] to [0008], the Fc domain comprises SEQ ID NO: 7.

Embodiment [0010]: In some embodiments of the present invention, such as, but not limited to, those described in embodiments [0001] to [0008], the Fc domain comprises SEQ ID NO: 8.

Embodiment [0011]: In some embodiments of the present invention, such as, but not limited to, those described in embodiments [0001] to [0010], the ACE2 domain is connected to the immunoglobin region through a linker.

Embodiment [0012]: In some embodiments of the present invention, such as, but not limited to, those described in embodiment [0011], the linker is SEQ ID NO: 10.

Embodiment [0013]: In some embodiments of the present invention, such as, but not limited to, those described in embodiment [0001], the chimeric ACE2-Immunoglobulin antibody has greater than 50% sequence identity to SEQ ID NO: 2 or SEQ ID NO: 3.

Embodiment [0014]: In some embodiments of the present invention, such as, but not limited to, those described in embodiment [0001], the chimeric ACE2-Immunoglobulin antibody of claim 1 has greater than 50% sequence identity to SEQ ID NO: 4 or SEQ ID NO: 5.

Embodiment [0015]: In some embodiments of the present invention, such as, but not limited to, those described in embodiments [0001] to [0014], the ACE2 domain binds to each of two or more SARS CoV-2 variants with a binding affinity indicated by $K_D$ less than 10 nM.

Embodiment [0016]: In some embodiments of the present invention, such as, but not limited to, those described in embodiments [0001] to [0014], the ACE2 domain binds to each of two or more SARS CoV-2 variants with a binding affinity indicated by $K_D$ less than 1 nM.

Embodiment [0017]: In some embodiments of the present invention, such as, but not limited to, those described in embodiments [0001] to [0014], the ACE2 domain binds to each of two or more SARS CoV-2 variants with a binding affinity indicated by $K_D$ less than 0.750 nM.

Embodiment [0018]: In some embodiments of the present invention, such as, but not limited to, those described in embodiments [0001] to [0014], the ACE2 domain binds to each of two or more SARS CoV-2 variants with a binding affinity indicated by $K_D$ less than 0.6 nM (600 pM).

Embodiment [0019]: In some embodiments of the present invention, such as, but not limited to, those described in embodiments [0015] to [0018], binding to a SARS-CoV-2 variant comprises binding to one of an Si subunit, a spike protein trimer, and an RBD.

Embodiment [0020]: In some embodiments of the present invention, such as, but not limited to, those described in embodiments [0015] to [0019], the two or more SARS CoV-2 variants are variants from two or more of the following categories of variants: Alpha, Delta, and Omicron.

Embodiment [0021]: In some embodiments of the present invention, such as, but not limited to, those described in embodiment [0020], one of the two or more SARS CoV-2 variants is an Omicron variant.

Embodiment [0022]: In some embodiments of the present invention, such as, but not limited to, those described in embodiment [0021], the Omicron variant is BA.4.6, XBB.1, XBB.1.5, BA.1, BA.5, BQ.1.1, BA.2.75 or BA.2.

Embodiment [0023]: In some embodiments of the present invention, such as, but not limited to, those described in embodiments [0021] and [0022], the ACE2 domain binds to the spike protein trimer of the Omicron variant with a binding affinity indicated by $K_D$ less than 0.9 nM (900 pM).

Embodiment [0024]: In some embodiments of the present invention, such as, but not limited to, those described in embodiments [0021] and [0022], the ACE2 domain binds to the spike protein trimer of the Omicron variant with a binding affinity indicated by $K_D$ less than 0.250 nM (250 pM).

Embodiment [0025]: In some embodiments of the present invention, such as, but not limited to, those described in embodiments [0021] and [0022], the ACE2 domain binds to the spike protein trimer of the Omicron variant with a binding affinity indicated by $K_D$ less than 0.001 nM (1 pM or 1,000 fM).

Embodiment [0026]: In some embodiments of the present invention, such as, but not limited to, those described in embodiments [0021] and [0022], the Omicron variant is BA.2 or BA.2.75 and the ACE2 domain binds to the spike protein trimer of the Omicron variant with a binding affinity indicated by $K_D$ less than 0.5 pM (500 fM).

Embodiment [0027]: In some embodiments of the present invention, such as, but not limited to, those described in embodiments [0001] to [0026], the antibody is capable of neutralizing the binding of SARS CoV-2 to human ACE2.

Embodiment [0028]: In some embodiments of the present invention, such as, but not limited to, those described in embodiments [0001] to [0027], the antibody has a binding affinity for FcRn indicated by $K_D$ less than 500 nM.

Embodiment [0029]: In some embodiments of the present invention, such as, but not limited to, those described in embodiments [0001] to [0027], the antibody has a binding affinity for FcRn indicated by $K_D$ less than 100 nM.

Embodiment [0030]: In some embodiments of the present invention, such as, but not limited to, those described in embodiments [0001] to [0003], [0005] to [0009], and [0011] to [0013], the half-life of the antibody is more than 3 times the half-life of a chimeric ACE2-Immunoglobulin comprising SEQ ID NO: 2 or SEQ ID NO: 3.

Embodiment [0031]: In some embodiments of the present invention, such as, but not limited to, those described in embodiments [0001] to [0003], [0005] to [0009], and [0011] to [0013], the half-life of the antibody is more than 4 times the half-life of a chimeric ACE2-Immunoglobulin comprising SEQ ID NO: 2 or SEQ ID NO: 3.

Embodiment [0032]: In some embodiments of the present invention, such as, but not limited to, those described in embodiments [0001] to [0031], the chimeric ACE2-Immunoglobulin antibody is capable of binding with decreased Fc effector functions including decreased binding to FcγRs and/or C1q.

Embodiment [0033]: Embodiments of the present invention encompass a pharmaceutical composition comprising a chimeric ACE2-Immunoglobulin antibody as described in embodiments [0001] to [0032].

Embodiment [0034]: In some embodiments of the present invention, such as, but not limited to, those described in embodiment [0033], the composition is formulated for intranasal delivery or respiratory nebulization.

Embodiment [0035]: In some embodiments of the present invention, such as, but not limited to, those described in embodiment [0033], the composition is formulated as an injection.

Embodiment [0036]: In some embodiments of the present invention, such as, but not limited to, those described in embodiments [0033] to [0035], the composition is a prophylactic.

Embodiment [0037]: Embodiments of the present invention encompass methods for administering to a subject in need thereof, an effective amount of the chimeric ACE2-Immunoglobulin antibody described in embodiments [0001] to [0032].

Embodiment [0038]: Embodiments of the present invention encompass methods for administering to a subject in need thereof, an effective amount of a pharmaceutical composition as described in embodiments [0033] to [0036].

Embodiment [0039]: In some embodiments of the present invention, such as, but not limited to, those described in embodiments [0037] and [0038], the treatment is prophylactic.

Embodiment [0040]: In some embodiments of the present invention, such as, but not limited to, those described in embodiments [0037] and [0038], the treatment is therapeutic.

Embodiment [0041]: In some embodiments of the present invention, such as, but not limited to, those described in embodiments [0037] to [0040], the administering comprises intranasal delivery, respiratory nebulization, or injection.

Embodiment [0042]: In some embodiments of the present invention, such as, but not limited to, those described in embodiments [0037] to [0040], the administering comprises injection every 1-2, 2-3, 3-6, or 6-12 months, or every 1-2, 3-4, 4-5, or 5-10 years.

Embodiment [0043]: In some embodiments of the present invention, such as, but not limited to, those described in embodiments [0037] to [0042], the effective amount is sufficient to treat a respiratory viral infection.

Embodiment [0044]: In some embodiments of the present invention, such as, but not limited to, those described in embodiment [0042], the respiratory viral infection is a SARS-CoV-2 infection.

Embodiment [0045]: In some embodiments of the present invention, such as, but not limited to, those described in embodiments [0037] to [0044], the method is effective to treat antibody-dependent enhancement.

Embodiment [0046]: In some embodiments of the present invention, such as, but not limited to, those described in embodiments [0037] to [0038] and [0040] to [0045], the method is effective to decrease or eliminate post-acute sequelae of COVID-19 (PASC).

EXAMPLES

Example 1

Molecular models were developed based on publicly available ACE2 and SARS-CoV-2 sequence databases with Protean 3D Version 17.3 (DNASTAR. Madison, WI) software, which uses a knowledge-based potential to solve protein folding and protein structure prediction problems.

The full-length ACE2-IgG molecule was extensively modeled using the DNASTAR Lasergene Protean 3-D version 17.3 molecular modeling software (DNASTAR, Inc. 3801 Regent St, Madison, WI 53705) which uses the I-TASSER engine to optimize ACE2 variant binding to multiple SARS-CoV-2 variants. Based on the parent software I-TASSER, the method can differentiate well between Leucine and Isoleucine, an ability important for the potential analysis of leucines in viral and/or receptor variants.

Comparisons of atomic-level structures and interactions for SARS-CoV-2/ACE2 were achieved with the knowledge-based atomic potential algorithm DFIRE, which generates a numerical protein-protein interaction score that becomes more negative with more stabilizing molecular interactions. Mutations in the receptor (ACE2) protein yielding the highest affinity binding to the widest variety of viral (SARS-CoV-2) variants were sought. To find these, dozens of in silico experiments were performed.

Exemplary images of the three-dimensional model of the "LiVE Longer" chimeric antibody (ACE2 LVE, IgG Fc STR YTE) are shown in FIGS. 1A and 2, as described above. The ACE2 was similarly linked to an IgG Fc-silent version that did not include the YTE variants. FIG. lA shows the chimeric antibody bound to two SARS-CoV-2 RBDs. FIG. 2 shows the chimeric antibody bound to one FcRn (FCGRT UniProt Accession #P55899-1) and one β2-microglobulin (UniProt Accession #P61769-1).

To identify receptor protein variants having increased binding affinity to the viral protein, variations in the region of the receptor binding to the most highly conserved amino acids in the viral protein were explored. Specifically, variations in the amino acids in the ACE2 regions binding to the most highly conserved SARSCoV2 RBD anchor amino acid residues (L455, F456 and Y473) were explored and evaluated based on images from the three-dimensional modeling and DFIRE scores.

FIGS. 1B to 1E, 3E, and 13, as described above, show three-dimensional models of the ACE2/SARS-CoV-2 interface and illustrate three ACE2 mutations found to impart high binding affinity to the widest range of SARS-CoV-2 variants, namely, T27L, H34V and N90E (LVE).

As shown in FIG. 1B (wild type), FIG. 1E (wild type), FIG. 3E (Delta), and FIG. 13 (Omicron), ACE2 amino acid L27 interacts with RBD amino acids Y473 and F456, while ACE2 amino acid V34 may interact with RBD amino acids L455 and Y453. There is a structural rearrangement in the Omicron variant of RBD 417, which allows for a closer interaction between ACE2 V34 and Omicron RBD L455 than in other variants. Also, as shown in FIG. 3E, the aliphatic side chain of the Omicron Q493R mutation (purple) makes contact ACE2 V34.

The DFIRE modeling using DNASTAR Lasergene Protean 3-D version 17.3 suggested that N90E was favorable in ACE2/SARS-CoV-2 RBD binding, even though there is no clear consensus from published references. As shown in FIGS. 1C, the ACE2 substitution N90E eliminates a site for N-linked glycosylation and thereby permits higher affinity binding. This is presumably due to loss of steric hindrance otherwise caused by the glycan, based on the DNASTAR modeling program. As shown in FIG. 13, the N90E mutation also and unexpectedly causes a hydrogen bond to form between ACE2 26K and 90E (a Lys26-Glu90 H bond), which further stabilizes ACE2 27L and the interaction between ACE2 27L and Omicron RBD residues Y473 and F456.

Extensive modeling of the ACE2 LVE (ACE2 T27L H34V N90E) variant and ACE2 YVE (ACE2 T27Y H34V N90E) variant bound to multiple major SARS-CoV-2 VOC, including Alpha, Delta, and the Omicron variant (PDB 7WBP) were completed. Three dimensional models were used to compare the binding affinity of the ACE2 LVE variant for wild type RBD with the binding affinity of a known ACE2 variant (having YTY at positions 27, 79 and 330, respectively) for wild type RBD. As reported in FIG. 1D, the models indicated stronger binding of the ACE2 LVE (DFIRE score −6.67) than of the ACE2 YTY variant (DFIRE score −4.53) to wild type RBD.

Thus, three dimensional modeling indicates that the LVE variant has stronger affinity binding to wild-type RBD than a known variant, and also binds more strongly to currently circulating Omicron variants than to previously circulating wild-type and Delta variants.

Example 2

Viral and protein constructs: Viral Receptor Binding Domain (RBD), Si protein subunit and S1 subunit trimers were synthesized by ACRO Biosystems, Newark, Delaware as recombinant proteins designed on the basis of publicly available sequence data. Recombinant human ACE2 constructs were synthesized by Absolute Antibody (Cleveland, United Kingdom) designed on the basis of sequence data obtained from NCBI protein sequence data and modified as described herein. The ACE2/mAb chimeras were synthesized by Absolute Antibody (Boston, MA).

Example 3

The C-Pass surrogate Viral Neutralization Test ("C-Pass sVNT Test" or "sVNT Test"), provided by GenScript USA Inc. (860 Centennial Ave. Piscataway, NJ 08854) and described in "C-Pass SARS-CoV-2 Neutralization Antibody Detection Kit update 2022.02.17" (GS-SOP-CPTS001G-05_L00847-C, incorporated herein by reference in its entirety), was used to characterize the antibodies disclosed herein. The manufacturer's instructions were followed without modification except where specifically noted below.

The C-Pass sVNT Test can detect circulating neutralizing antibodies against SARS-CoV-2 that block the interaction between the receptor binding domain (RBD) of the viral spike glycoprotein with the ACE2 cell surface receptor. The assay detects any antibodies in serum and plasma that neutralize the RBD-ACE2 interaction. The test is both species and isotype independent.

As would be know to a person of skill in the art, the SARS-CoV-2 sVNT Kit is a blocking ELISA detection tool that mimics the virus neutralization process. The kit contains two key components: the Horseradish peroxidase (HRP) conjugated recombinant SARS-CoV-2 RBD fragment (HRP-RBD) and the human ACE2 receptor protein (hACE2). The protein-protein interaction between HRP-RBD and hACE2 can be blocked by neutralizing antibodies against SARS-CoV-2 RBD.

First, the samples and controls are pre-incubated with the HRP-RBD to allow the binding of the circulating neutralization antibodies to HRP-RBD. The mixture is then added to the capture plate which is pre-coated with the hACE2 protein. The unbound HRP-RBD as well as any HRP-RBD bound to non-neutralizing antibody will be captured on the plate, while the circulating neutralization antibodies-RBD complexes remain in the supernatant and get removed during washing. After washing steps, TMB solution is added, making a blue color. By adding Stop Solution, the reaction is quenched, and the color turns yellow. This final solution can be read at 450 nm in a microtiter plate reader. The absorbance of the sample is inversely dependent on the titer of the anti-SARS-CoV-2 neutralizing antibodies.

The C-Pass sVNT Test protocol as followed herein was as follows:

Reagent Preparation

1. All reagents must be taken out from refrigeration and allowed to return to room temperature before use (20° to 25° C.). Save all reagents in refrigerator promptly after use.
2. All samples and controls should be vortexed before use.
3. HRP-RBD Preparation: Dilute HRP conjugated RBD with HRP Dilution Buffer with a volume ratio of 1:1000. For example, for one 96 well plate testing, dilute 10 µL of HRP conjugated RBD with 10 mL of HRP Dilution Buffer to make a HRP-RBD working solution.
4. 1× Wash Solution Preparation: Dilute the 20× Wash Solution with deionized or distilled water with a volume ratio of 1:19. For example, dilute 40 mL of 20× Wash Solution with 760 mL of deionized or distilled water to make 800 mL of 1× Wash Solution. Store the solution at 2° C. to 8° C. when not in use.

Sample and Control Dilution

Dilute test samples, Positive, and Negative Controls with Sample Dilution Buffer with a volume ratio of 1:9. For example, dilute 10 µL of sample with 90 µL of Sample Dilution Buffer.

1. It is recommended that all Positive Control and Negative Control should be prepared in duplicate.
2. Count the strips according to the number of test samples and install the strips. Make sure the strips are tightly snapped into the plate frame.
3. Leave the unused strips in the foil pouch and store at 2° C. to 8° C. The strips must be stored in the closed foil pouch to prevent moisture from damaging the Capture Plate.

Test Procedure/Neutralization Reaction

1. In separate tubes, mix the diluted Positive Control, diluted Negative Control, and the samples with the diluted HRP-RBD solution with a volume ratio of 1:1. For example, mix 60 µL Positive Control with 60 µL HRP-RBD solution. Incubate the mixtures at 37° C. for 30 minutes.
2. Add 100 µL each of the positive control mixture, the negative control mixture, and the sample mixture to the corresponding wells.
3. Cover the plate with Plate Sealer and incubate at 37° C. for 15 minutes.
4. Remove the Plate Sealer and wash the plate with 260 µL of 1× Wash Solution for four times.
5. Pat the plate on paper towel to remove residual liquid in the wells after washing steps.
6. Add 100 µL of TMB Solution to each well and incubate the plate in the dark at 20-25° C. for 15 minutes (start timing after the addition of TMB Solution to the first well).
7. Add 50 µL of Stop Solution to each well to quench the reaction.
8. Read the absorbance in the microtiter plate reader at 450 nm immediately.

The C-Pass sVNT was developed to report neutralizing titers, which can be expressed as dilution ratios or in mg/ml or ng/ml (concentration). The original concentration of all ACE2 Fc fusion proteins supplied by Absolute Antibody was 1 mg/ml, the first dilution was 1:20 or 0.05 mg/ml, then 1:2 serial dilutions were done for a final concentration of 2.4 ng/ml. The cut off for the C-Pass sVNT is O.D.=0.3; i.e. an Optical Density (O.D.)<0.3 is neutralizing. The titer data are expressed herein as dilution and/or concentration.

FIGS. 3A and 3B show the Optical Density (O.D.) as measured for the C-Pass sVNT Test of the ACE2 "LiVE" variant (ACE2 T27L, H34V, N90E IgG Fc STR) against WT and Delta variant RBD over the indicated dilutions. Results for the original Wuhan "Wild type" (WT) SARS-CoV-2 RBD (ACRO Biosystems Cat No.: SPD-052H1 SARS-CoV-2 (COVID-19) S protein RBD, His Tag)/HRP conjugate (HRP Conjugation kit-Lighting Link-Abcam Cat. No. ab102890) are shown in blue. Results for the Delta variant SARS-CoV-2 RBD (ACRO Biosystems Cat No.:SPD-05226 SARS-CoV-2 Spike RBD (K417N, L452R, T478K), His Tag/HRP conjugate (HRP Conjugation kit-Lighting Link-Abcam Cat. No. ab102890) are shown in red. Over all dilutions, the ACE2 "LiVE" chimeric antibody neutralizes the WT approximately the same as it neutralizes the Delta variant. Both the WT and the Delta variant RBD have sVNT titers of ~1:20,480 and ~4.9 ng/ml. This shows that the "LiVE" variant chimeric antibody is variant resistant (i.e. variant agnostic).

FIG. 3C shows the Optical Density (O.D.) as measured using the C-Pass sVNT Test of the ACE2 "LiVE" variant (ACE 2 T27L H34V N90E IgG Fc STR) for Beta and wild type variants. The "LiVE" chimera neutralizes the RBD of the SARS-CoV-2 Beta variant B.1.351 with greater potency (red front bars, ~2.4 ng/ml) than for the w.t. RBD (blue back bars, ~4.9 ng/ml).

FIG. 3D shows the Optical Density (O.D.) as measured using the C-Pass sVNT Test of the ACE2 "LiVE" variant (ACE 2 T27L H34V N90E IgG Fc STR) compared to the Genscript chimera for the Alpha variant. The "LiVE" chimera neutralizes the RBD of the SARS-CoV-2 Alpha variant B1.1.7 significantly better (dark blue front bars, ~4.9 ng/ml) than did the Genscript Fc-IgG/ACE2 chimera Z03516 (light blue back bars, ~6.3 ug/ml).

FIG. 4 shows the Optical Density (O.D.) as measured using the C-Pass sVNT Test of the ACE2 "LiVE" variant (ACE 2 T27L H34V N90E IgG Fc STR) against Omicron and Alpha variant spike protein timer. Results for the Omicron variant spike protein trimer (ACRO Biosystems Cat. No. SPN-052Hz SARS-CoV-2 Spike Trimer, His Tag B.1.1.529/Omicron)/HRP conjugate/HRP Conjugation kit- Lighting Link, Abcam Cat. No. ab102890) are shown in green. Results for the SARS-CoV-2 Alpha variant S1/HRP conjugate (ACRO Biosystems SPN-052H6 SARS-CoV-2 S protein (HV69-70del, Y144del, N501Y, A570D, D614G, P681H, T7161, S982A, D1118H), His Tag HRP Conjugation kit-Lighting Link-Abcam Cat. No. ab102890) are shown in blue. Over all dilutions, the ACE2 "LiVE" chimeric antibody neutralizes the Omicron variant approximately as well as it neutralized the Alpha variant. making the "LiVE" ACE2 chimeric antibody ARS CoV-2 variant resistant to both the SARS-CoV-2 VOC Omicron and SARS-CoV-2 VOC Alpha.

FIG. 5 shows the Optical Density (O.D.) as measured using the C-Pass sVNT Test of the ACE2 "LiVE" variant (ACE 2 T27L H34V N90E IgG Fc STR) (shown in blue) and the "LiVE Longer" variant (ACE2 T27L H34V N90E IgG Fc STR YTE) (shown in green) against the Omicron variant RBD (ACRO Biosystems Cat. No.: SPD-052H3 SARS-CoV-2 (COVID-19) S protein RBD, His Tag B.1.1.529/ Omicron)/HRP conjugate/HRP Conjugation kit-Lighting Link, Abcam Cat. No. ab102890). The "LiVE" variant neutralized Omicron RBD approximately as well as the "LiVE Longer" variant chimeric antibody neutralizes Omicron RBD, showing that the addition of the IgG Fc YTE mutations in the "LiVE Longer" chimeric antibody does not affect ACE2 to Omicron RBD neutralization. Note that the "LiVE Longer" chimeric antibody (shown in green) slightly outperformed the "LiVE" chimeric antibody (shown in blue), even though the sVNT titers for both the "LiVE" and the "LiVE Longer" chimeric antibodies are both ~1:20,480.

FIG. 6 shows the Optical Density (O.D.) as measured using the C-Pass surrogate Viral Neutralization Test of the ACE2 "LiVE" variant (ACE 2 T27L H34V N90E IgG Fc STR) (shown in blue) and the "LiVE Longer" variant (ACE2 T27L H34V N90E IgG Fc STR YTE) (shown in green) against the Omicron variant spike protein trimer (ACRO Biosystems Cat. No.: SPN-052Hz SARS-CoV-2 Spike Trimer, His Tag B.1.1.529/Omicron)/HRP conjugate (HRP Conjugation kit-Lighting Link, Abcam Cat. No. ab102890). The LiVE variant neutralized Omicron spike protein trimer approximately as well as the "LiVE Longer" chimeric antibody neutralized Omicron spike protein timer, showing that the addition of the IgG Fc YTE mutations in the "LiVE Longer" chimeric antibody does not significantly affect ACE2 to Omicron spike protein trimer neutralization. Note that the "LiVE Longer" chimeric antibody (shown in green) slightly outperformed the "LiVE" chimeric antibody (shown in blue), even though the sVNT titers for both the "LiVE" and the "LiVE Longer" chimeric antibodies are both ~1:20,480.

Example 4

The binding affinities of ACE2/IgG Chimeras to SARS-CoV-2 Variant Constructs were determined by Surface Plasmon Resonance (SPR) assays of protein-protein interactions performed by Acro Biosystems (Beijing Economic Development Zone, Beijing China), on a Biacore T200 Instrument fitted with Series SCM5 Sensor Chip, except for analyses of BA.4.6, BQ.1.1/ XBB .1 and ACRO's wt ACE2 Fc fusion protein, which were done on a Biacore 8K Instrument. Prior to SPR assay, samples were desalted on Zeba Spin 7K MWCO columns. Binding affinities were determined in HBS-N buffer, 10× (0.1 M HEPES, 1.5MNaCl) containing EDTA and Tween 20, at a flow rate of 30 μL/minute, run for 120 seconds association and 180 seconds dissociation. The reference subtracted SPR binding curves were blank subtracted, and curve fitting was performed with a 1:1 model to obtain kinetic parameters using the Biacore T200 Evaluation software. Binding data are reported as estimated dissociation constant (KD).

FIG. 7 shows the actual binding affinity of the "LiVE" variant (ACE 2 T27L H34V N90E IgG Fc STR) against the Omicron spike protein trimer. BIACore SPR analysis was performed by ACRO Biosystems. The binding affinity of ACE2 LVE IgG Fc STR for Omicron spike protein trimer is 144 pM (0.144 nM).

FIG. 8 shows the actual binding affinity of the "LiVE Longer" variant (ACE2 T27L H34V N90E IgG Fc STR YTE) against the Alpha spike protein timer (ACRO Biosystems Cat. No. SPN-052H6). BIACore SPR analysis was performed by ACRO Biosystems. The binding affinity of ACE2 LVE IgG Fc STR YTE for Alpha spike protein timer is 92.8 pM (0.0928 nM).

FIG. 9A shows the actual binding affinity of the "LiVE Longer" variant (ACE2 T27L H34V N90E IgG Fc STR YTE) against the Omicron BA.1 VOC spike protein trimer (ACRO Biosystems SPN-052Hz). BIACore SPR analysis was performed by ACRO Biosystems. The binding affinity is 73.4 pM (0.0734 nM).

FIG. 9B shows the actual binding affinity of "LiVE Longer" variant (ACE2 T27L H34V N90E IgG Fc STR YTE) against the new Omicron BA.2 sub-VOC spike protein trimer. This variant is fueling the next world-wide wave of SARS-CoV-2. The binding affinity is 78.2 fM (femtomolar).

The $K_D$ for the "LiVE Longer" variant against the Omicron BA.2 sub-VOC is thus ~1,000 times better than the $K_D$ for the "LiVE Longer" variant against the "original" Omicron BA.1 VOC (73.4 pM, FIG. 9A).

Example 5

Binding data for additional variants were determined as for Example 4 and are summarized in Table 1. Specifically, Table 1 provides the measured binding affinities, determined by SPR assay, of LiVE and LiVE-longer chimeric antibodies to purified recombinant RBD subunits, S1 subunits containing the RBD, or S1 subunit trimers designed to mimic the Alpha, Delta or Omicron variants of SARS-CoV-2 (as indicated). For comparison, the data are displayed alongside binding data for wild-type ACE2/Fc fusion proteins from ACRO Biosystems, which have binding affinities of 27 nM, 16 nM and ~3 nM, respectively, to the Omicron BA4.6 spike protein trimer and Wuhan strain S1 subunits, respectively.

As shown in Table 1, the LiVE and LiVE-longer chimeric antibodies had low-to-mid picomolar binding affinities to the Alpha, Delta or Omicron variant constructs, all orders of magnitude higher affinity than the commercial wild-type hACE2 constructs. Of special note, the highest affinity bindings were observed for the YTE variant "LiVE Longer" chimera to the Omicron subvariant BA.2 spike trimer (78fM), to the Omicron subvariant BA2.75 spike trimer (133fM), to the Omicron subvariant spike trimers BA.1 (73 pM), BQ.1.1 (1.81 pM), and to the Alpha B.1.1.7 variant (93 pM), and to the Omicron XBB.1 spike protein trimer (215 pM).

On Dec. 31, 2022, the CDC reported that a new Omicron subvariant, XBB.1.5, made up 40.1% of U.S. COVID cases. As explained in Yue et al., "Enhanced transmissibility of XBB.1.5 is contributed by both strong ACE2 binding and antibody evasion," (doi.org/10.1101/2023.01.03.522427 Jan. 5, 2021), this Omicron subvariant has substitution S:F486P, which restores the hydrophobics pocket around RBD F486, and much higher binding affinity for ACE2 than BQ.1.1 and XBB/XBB .1 sublineages. Since Omicron subvariant XBB.1.5 has increased binding affinity to ACE2, it is expected that Omicron subvariant XBB.1.5 will also have higher binding affinity for the ACE2 Fc fusion proteins disclosed in this invention.

TABLE 1

| ACE2/IgG Chimera | SARS-CoV-2 Construct | $K_D$ by SPR* |
|---|---|---|
| LiVE chimera | Alpha variant B.1.1.7, S1 subunit | 378 pM |
| LiVE-Longer chimera | Alpha variant B.1.1.7, S1 subunit | 93 pM |
| LiVE chimera | Delta variant B.1.617.2, RBD only† | 554 pM |
| LiVE-Longer chimera | Delta variant B.1.617.2, RBD only† | 507 pM |
| LiVE chimera | Omicron BA.1 spike protein trimer | 144 pM |
| LiVE-Longer chimera | Omicron BA.1 spike protein trimer | 73 pM |
| LiVE-Longer chimera | Omicron BA.2 spike protein trimer | 78 fM |
| LiVE-Longer chimera | Omicron BA.2.75 spike protein trimer | 133 fM |
| LiVE-Longer chimera | Omicron BA.5 spike protein trimer | 5.43 pM |
| LiVE chimera | Omicron** RBD only† | 308 pM |
| LiVE-Longer chimera | Omicron** RBD only† | 402 pM |
| LiVE-Longer chimera | Omicron BA4.6 spike protein trimer | 845 pM |
| hACE2, Fc tag (ACRO)*** | Omicron BA4.6 spike protein trimer | 27.1 nM |
| LiVE-Longer chimera | Omicron BQ.1.1 spike protein trimer | 1.81 pM |
| hACE2, Fc tag (ACRO)*** | Omicron BQ.1.1 spike protein trimer | 12.6 nM |
| LiVE Longer chimera | Omicron XBB.1 spike protein trimer | 215 pM |
| hACE2, Fc tag (ACRO)*** | Omicron XBB.1 spike protein trimer | 22.4 nM |
| hACE2, Fc tag (ACRO)*** | Wuhan variant, S1 subunit | 16.0 nM |

*Surface Plasmon Resonance assay (Acro Biosystems)

**Omicron VOC B.1.1.529

***Human ACE2, Fc Tag (Cat. No. AC2-H5257, ACRO Biosystems)

†Note:

The RBD has less avidity than whole SARS-CoV-2 spike protein trimer and therefore the binding affinities are much higher (less strong) for the RBD than for the whole SARS-CoV-2 spike protein trimer. Intact SARS-CoV-2 virions display the whole SARS-CoV-2 spike protein trimer, so the binding affinities for the whole SARS-CoV-2 spike protein trimer more accurately reflect the actual binding affinities of the ACE2 chimeric mAbs for the whole SARS-CoV-2 spike protein trimer.

Surprisingly, the LiVE Longer (ACE2 LVE IgG Fc STR YTE) chimeric antibody had higher binding affinities for the Alpha variant B.1.1.7 51 spike protein, Delta variant B.1.617.2 RBD, and Omicron BA.1 spike protein trimer than the LiVE (ACE2 LVE IgG Fc STR) chimeric antibody, even though the ACE2 mutations (ACE2 T27L, H34V, N90E) are identical for the two antibodies. Since the only difference between the LiVE Longer and LiVE antibodies is the IgG Fc YTE mutations, this is a novel finding for an IgG Fc YTE mAb. Without being bound by theory it is believed that the increase in ACE2/SARS-CoV-2 binding affinity for inclusion of Fc YTE variations may result from the fact that the LiVE Longer antibody may be able to form IgG hexamers (see example 9) easier than the LiVE antibody as the YTE mutations are located in the same area of the IgG Fc CH2/CH3 cleft that forms IgG hexamers.

The high binding affinity of both the LiVE (ACE2 LVE IgG Fc STR) mAb and LiVE Longer (ACE2 LVE IgG Fc STR YTE) mAb for the Omicron trimer likely results from the increased affinity of the Omicron spike protein trimer for ACE2 and cooperative binding of the ACE2 LVE dimers binding to the full-length SARS-CoV-2 spike protein trimer.

Example 6

FIG. 10A shows the actual binding affinity of the ACE2 "LiVE" variant (ACE 2 LVE IgG Fc STR) for FcRn. BIACore SPR analysis was performed by ACRO Biosystems. The binding affinity is 517 nM at pH 6.0.

FIG. 10B shows the actual binding affinity of the ACE2 "LiVE Longer" variant (ACE2 LVE IgG Fc STR YTE) for FcRn. BIACore SPR analysis was performed by ACRO Biosystems. The binding affinity is 26.7 nM at pH 6.0. This binding affinity is sufficiently strong that the LiVE Longer variant can bind to FcRn that is extensively expressed in the upper and lower respiratory tract. FcRn (FCGRT) protein expression includes the CNS/brain/olfactory bulb/respiratory epithelia, heart, gastrointestinal tract, and lymphoid tissue/macrophages.

FIG. 10B also shows that the incorporation of the IgG Fc YTE mutation in the ACE2 "LiVE Longer" variant results in a 19-fold increase in binding affinity for FcRn at pH 6.0 as compared to the ACE2 LiVE variant. This is surprisingly higher than the increase reported for other IgG Fc YTE antibodies. An analogous mutation of M252Y/S254T/T256E within the Fc region of motavizumab ("mota-YTE") led to a 10-fold increase relative to non-YTE variants in in vitro FcRn binding at pH 6.0 for both humans and monkey, and a 4-fold increase in in vivo serum half-life in monkeys, as described in Robble et al., Antimicrob Agents Chemother 57(12): 6147-6153 (2013).

Binding affinity to FcRn is a strong indicator of IgG in vivo half-life. Accordingly, without being bound by theory, it is believed that any mutations that increase binding affinity for FcRn will increase binding efficiencies in a non-liner manner, as well as increasing half-lives. It is expected that the ACE "Live Longer" variant will have correspondingly greater half-life in humans and non-human primates.

Such an increase in binding affinity to FcRn has not been demonstrated for an ACE2 Fc fusion protein. The much larger (about 2-fold) increase in binding affinity of the antibodies described herein with incorporation of the YTE mutation is substantial and significant. The magnitude of the increase has the potential to extend in vivo half-life sufficiently to overcome muco-ciliary clearance. It is also surprising, particularly because the Fc STR mutations described herein do not change the binding of IgG Fc to FcRn. No published reference notes increased Fab epitope affinity for a wild-type IgG where the Fab arms also interact with FcRn and contribute to increasing the half-life independent of the direct IgG Fc CH2-CH3 region that directly binds to FcRn (see FIG. 2). The increased binding affinity, avidity, and increased neutralization of live SARS-CoV-2 Omicron BA.1 shows that the inclusion of the YTE mutations have an unanticipated novel and inventive improvement in the binding affinity, avidity and neutralization function of the ACE2 chimeric antibodies disclosed herein.

The YTE variant also decreases antibody-dependent cellular cytotoxicity (ADCC), desirable in a prophylactic, as described by Front, Immunol. 10:1296 (2019).

Example 7

Omicron BA.2 spike protein trimer is defined as follows: SARS-CoV-2 Spike Trimer, His Tag (BA.2/Omicron) (SPN-05223), which is the ectodomain of SARS-CoV-2 spike protein and contains AA Val 16-Pro 1213 (Accession #

QHD43416.1 (T191, LPP24-26de1, A27S, G142D, V213G, G339D, S371F, S373P, S375F, T376A, D405N, R4085, K417N, N440K, S477N, T478K, E484A, Q493R, Q498R, N501Y, Y505H, D614G, H655Y, N679K, P681H, N764K, D796Y, Q954H, N969K, R683A, R685A, F817P, A892P, A899P, A942P, K986P, V987P)). The spike mutations are identified on the SARS-CoV-2 Omicron variant (Pango lineage: BA.2; GISAID clade: GRA; Nextstrain clade: 21L).

Soon after the emergence and global spread of a SARS-CoV-2, an Omicron variant now designated Omicron lineage BA.1 developed, and another Omicron lineage, BA.2, was then developed and has been outcompeting BA.1. Statistical analysis shows that the effective reproduction number of BA.2 is 1.4-fold higher than that of BA.1. Neutralization experiments show that the vaccine-induced humoral immunity fails to function against BA.2 like it does for BA.1, and the antigenicity of BA.2 is different from BA.1. Cell culture experiments show that BA.2 is more replicative in human nasal epithelial cells and more fusogenic than BA.1. Infection experiments using hamsters show that BA.2 is more pathogenic than BA.1.

The antibodies disclosed herein are effective in neutralizing a variety of known SARS-CoV-2 variants, including possibly the more infectious and more pathogenic SARS-CoV-2 Omicron BA.2 sub-variant.

FIG. 14 shows the binding affinity of the "LiVE Longer" variant (ACE2 LVE IgG Fc STR YTE) against the SARS-CoV-2 Alpha spike protein 51 (ACRO Biosystems Cat. No. SPN-052H6). BIACore SPR analysis was performed by ACRO Biosystems.

FIG. 15 shows the binding affinity of the "LiVE Longer" variant (ACE2 LVE IgG Fc STR YTE) against the Omicron spike protein trimer (ACRO Biosystems Cat. No. SPN-052Hz). BIACore SPR analysis was performed by ACRO Biosystems.

FIG. 16 shows the binding affinity of the "LiVE Longer" variant (ACE2 LVE IgG Fc STR YTE) against the Omicron BA.2 spike protein trimer (ACRO Biosystems Cat. No. SPN-05223). BIACore SPR analysis was performed by ACRO Biosystems.

Example 8

FIG. 11 provides now publicly available data from mAbsolve (available at mabsolve.com/science/#linkone) that was included in and developed with the antibodies described herein. As shown in FIG. 11, the "STR" "Fc silent" technology has less binding to C1q and all classes of activating and inhibiting FcγRs (FcγRI, FcγRIIA/b and FcγRIII) as compared to wild type, LALA, LALA-P329G A, aglycosylated IgG and N297A mutations.

Fc Silent technology can abolish FcγRIIa or FcγRIIa mediated ADE, coagulopathies, or cytokine storms by IgG antibodies. Abolishing binding to C lq eliminates complement ADE or C'ADE. In SARS-CoV-2/COVID-19 infections, elevated TNF-α and IL-6 contribute to the "cytokine storm" associated with severe or fatal COVID-19 infections and have been implicated in PASC. By utilizing antibodies devoid of activating FcγRs or complement C1q, the mAbs disclosed herein cannot exacerbate the "cytokine storm" associated with severe or fatal COVID-19.

Example 9

Complement C1q only binds to IgG hexamers and not monomeric IgG. The MicroVue CIC-C1q EIA, Quidel Corp. ELISA assay was utilized, wherein the ELISA microtiter plates are coated with purified human C1q, to demonstrate the presence of ultra-potent ACE2 variant chimeric IgG hexamers. The manufacturer's protocol, as provided in its PIA001004EN00_09_21_MicroVue_CIC-C1q_EIA_Pkg_Insert.pdf, available at www.quidel.com/sites/default/files/product/documents/PIA001004EN00_09_21_MicroVue_CIC-C1q_EIA_Pkg_Insert.pdf, were followed.

The formation of IgG ACE2 hexamers was verified using IgG ACE2 variant chimeric antibody LVE STR IgG and SARS-CoV-2 Beta variant RBD antigen (K417N E484K & N501Y, ACRO Biosystems Cat. No. SPD-052Hp) by measuring antibody/antigen complexes binding to human C1q coated plates (MicroVue CIC-C1q EIA Kit, Catalog No. A001, Quidel Corp., 9975 Summers Ridge Road, San Diego, CA 92121). A result of O.D. 1.06 405 nM demonstrated the presence of ACE2 LVE IgG Fc STR mAb/SARS-CoV-2 Beta variant RBD antigen immune complexes, which bound to the purified C1q coated microtiter ELISA plates and showed that the ACE2 LVE STR IgG Fc STR mAb can form IgG hexamers.

Example 10

Complement Antibody Dependent Enhancement of Vero Cells (Complement Receptor (CR) positive (+), Fcγ R negative (−)) was demonstrated using wild type ACE2 IgG chimeric mAb (Human ACE2/Angiotensin-Converting Enzyme 2 Protein 1-740 (hACE2 full length IgG Fc Tag chimeric mAb) Sino Biological Catalog Number 10108-H02H) and live SARS-CoV-2 in a BSL3 lab (IIT Research Institute Life Sciences Group 10 West 35th Street Chicago, Illinois 60616) using the protocol discussed below.

African green monkey (Vero E6) cells were cultured in 96 well plates one day prior to the day of the assay. Vero E6 cells were greater than 90% confluency at the start of the study. Cells were pretreated with wild type ACE2 IgG chimeric mAb (Human ACE2 Protein 1-740 (hACE2 full length IgG Fc Tag chimeric mAb) Sino Biological Catalog Number 10108-H02H) for a minimum of 60 minutes before inoculation with virus. Cells were inoculated at a MOI of 0.01 TCID50/ of live SARS-CoV-2 (USA-WA1 2020 SARS-CoV-2), virus at a multiplicity of infection (MOI) of 0.01) and incubated for one hour in the presence of diluted wild-type ACE2 chimeric mAb Sino Biological Catalog Number 10108-H02H with eight dilutions of the ACE2-IgG chimeric antibody at 100 μg/ml, 10 μg/ml, 1 μ/ml, 0.1 μ/ml, 0.01 μ/ml, 0.001 μ/ml, 0.0001 μ/ml and 0.00001 μ/ml). Following 1 hour adsorption, cells were washed; and wells overlayed with 0.2 mL DMEM2 (DMEM with 2% FCS) containing test material and incubated in a humidified chamber at 37° C.±2° C. in 5±2% $CO_2$. At 72 hours post inoculation, 120 μl of the supernatant from each inoculated well was collected and stored at ≤−65° C. for subsequent analysis by qRT-PCR. Wells were evaluated in triplicate for cytotoxicity/cytoprotection by neutral red assay.

Complement Antibody Dependent Enhancement (C'ADE) was demonstrated by the eight dilutions of the ACE2-IgG chimeric antibody (wild type ACE2 IgG chimeric mAb (Human ACE2 /Angiotensin-Converting Enzyme 2 Protein 1-740 (hACE2 full length IgG Fc Tag chimeric mAb) Sino Biological Catalog Number 10108-H02H) at 100 μg/ml, 10 μg/ml, 1 μg/ml, 0.1 μg/ml, 0.01 m/ml, 0.001 μg/ml, 0.0001 μg/ml and 0.00001 m/ml ) since C'ADE only occurs with diluted IgG antibody. The results are shown in FIG. 12.

As the ACE2 IgG Fc chimeric mAb (Human ACE2 /Angiotensin-Converting Enzyme 2 Protein 1-740 (hACE2 full length IgG Fc Tag chimeric mAb) Sino Biological Catalog Number 10108-H02H) was diluted (log ACE2, mg/ml), there was a slight dose-dependent increase in viral CPE, consistent with C'ADE. It is noted that C'ADE due to complement C1q has been demonstrated with Ebola. Since Vero E6 cells lack Fcγ Rs, but express complement receptors (CR), the antibody enhancement observed must be due to C'ADE, highlighting the importance of using IgG Fc silent mAbs for prophylaxis of SARS-CoV-2.

Activation of complement C1q/classical complement cascade is clinically relevant in COVID-19. SARS-CoV-2 is recognized by C1q, likely as a result of immune complexes or C'ADE involving IgG1 and IgG3 (as can be seen in anti-acetylcholine receptor antibody-mediated Myasthenia Gravis and various other complement-activating autoimmune diseases which may share common HLA haplotype mutations) to initiate the overwhelming, disproportionate, and often lethal complement-mediated immune response, which directs the complement Membrane Attack Complex (MAC) against the virus and injures the lungs and other end organs such as the kidney and nervous system in the process. It additionally contributes to proinflammatory cytokine activation via C5a activation while promoting a prothrombotic state leading to DVT, PE, AMI, or stroke.

Antibodies disclosed herein do not trigger C1q activation and therefore may prevent C'ADE and other complement mediated immunopathogenesis associated with COVID-19.

Example 11

The results provided above show an excellent correlation between the DFIRE modeling score and the actual measured binding affinity.

Of note, the mutations at ACE2 T27 and ACE2 H34 were chosen because Deep Mutational Scanning of the ancestral RBD suggested that alternative RBD mutations (as compared to the wild-type RBD) in the ACE2 T27 and ACE2 H34 binding anchor amino acid residues of the SARS-CoV-2 RBD (SARS-CoV-2 RBD Y473, SARS-CoV-2 RBD F456 and SARS-CoV-2 RBD L455) are deleterious to SARS-CoV-2/ACE2 binding, making an ACE2 T27L or ACE2 T27Y and ACE2 H34V variant extremely resistant to current and future SARS-CoV-2 VOCs.

Example 12

Vero E6 cells (ATCC CRL-1586) were maintained in Dulbecco's Modified Eagle Medium (DMEM) medium supplemented with 10% fetal bovine serum (FBS) and 100 U/ml of penicillin—streptomycin. The assay was performed in duplicate using 24-well tissue culture plates (TPP Techno Plastic Products AG, Trasadingen, Switzerland) in a biosafety level 3 facility. Serial dilutions of each serum sample were incubated with 30-40 plaque-forming units of virus for 1 h at 37° C. The virus-serum mixtures were added onto pre-formed Vero E6 cell monolayers and incubated for 1 h at 37° C. in 5% CO2 incubator. The cell monolayer was then overlaid with 1% agarose in cell culture medium and incubated for 3 days, at which time the plates were fixed and stained. Antibody titers were defined as the highest serum dilution that resulted in >90% (PRNT90) reduction or >50% (PRNT50) in the number of virus plaques. This method has been extensively validated on SARS-CoV-2 infected and control sera previously .

Live wild type SARS-CoV-2 PRNT assays were performed at Colorado State University School of Veterinary Medicine BSL3 diagnostic laboratory (Colorado State University. 200 West Lake Street/2025 Campus Delivery, Infectious Disease Research Center Fort Collins, CO, US, 80521).

Each antibody ("LiVE" and "LiVE Longer" variants) were/are added to heat inactivated serum (Sigma Aldrich H3667-100ML HEAT INACTIVATED HUMAN SERUM FROM MALE AB PLASMA) in a 1:1 ratio (60 uL Ab to 60 uL serum). CSU BSL3 laboratory used their standard dilution scheme, which starts with an initial dilution of 1:5 (40 uL Ab in 160 uL media), and then serial dilutions of 1:2 (100 uL sample in 100 uL media). CSU BSL3 laboratory then add an equal volume of virus to each dilution, so that the final initial dilution is 1:10, and increases 2-fold from there (1:20, 1:40, etc.). Since the Abs were diluted 1:2 before diluting 1:5, the initial starting dilution (after adding virus) is 1:20 and CSU BSL3 laboratory tested 12 total dilutions for all samples so the range is 1:20 through 1:40,960.

CSU BSL3 laboratory tested the serum by itself, and CSU BSL3 laboratory had plaques in all wells with no neutralization, as expected.

The "LiVE" ACE2 LVE IgG Fc STR has a PRNT90 titer of 1:5120, and a PRNT50 of 1:10,240.

Example 13

Neurological complications are common in COVID-19. Although SARS-CoV-2 has been detected in patients' brain tissues, its entry routes and resulting consequences are not well understood. There is, however, upregulation of interferon signaling pathways of the neurovascular unit in fatal COVID-19. SARS-CoV-2 has been detected in the basolateral compartment in transwell assays after apical infection, suggesting active replication and transcellular transport of virus across the blood-brain barrier (BBB) in vitro. Because FcRn is widely expressed in the vasculature of the nasal blood vessels and the blood-brain barrier, the antibodies disclosed herein may help protect against SARS-CoV-2 neuro-invasion of the CNS.

There are several likely synergistic mechanisms by which SARS-CoV-2 infection may result in COVID-19-associated coagulopathy including cytokine release that activates leukocytes, endothelium, and platelets; direct activation of various cells by viral infection; and high levels of intravascular neutrophil extracellular traps (NETs). The latter are inflammatory cell remnants that amplify thrombosis. COVID-19-associated coagulopathy may manifest with thrombosis in venous, arterial, and microvascular circuits. The incidence of venous thromboembolism is particularly notable in severe COVID-19 (10% to 35%) with autopsy series suggesting that as many as 60% of those who succumb to COVID-19 are impacted. Recently, there have been a number of descriptions of what appears to be de novo autoantibody formation in individuals with severe COVID-19. One example replicated by multiple groups is the detection of antibodies reminiscent of the antiphospholipid antibodies (aPL) that mediate antiphospholipid syndrome (APS) in the general population. In APS, patients form durable autoantibodies to phospholipids and phospholipid-binding proteins such as prothrombin and beta-2-glycoprotein I (β32GPI). These autoantibodies then engage cell surfaces, where they activate endothelial cells, platelets, and neutrophils and thereby tip the blood: vessel wall interface toward thrombosis. While viral infections have long been known to trigger transient aPL, mechanisms by which these potentially short-lived antibodies may be pathogenic have not been deeply characterized. IgG fractions from patients with COVID-19 were enriched for aPL and potentiated thrombosis when injected into mice. Intriguingly, the circulating B cell compartment in COVID-19 appears similar to the autoimmune disease lupus, whereby naïve B cells rapidly take an extrafollicular route to becoming antibody-producing cells, and in doing so bypass the normal tolerance checkpoints against autoimmunity provided by the germinal center.

Since the vasculature and the endothelium express high levels of FcRn, the antibodies disclosed herein may help protect against the formation of pathological anti-endothelial autoantibodies and COVID-19 associated thrombosis.

The results show (see FIG. 17), consistent with the sVNT and BIACore data, that the "LiVE Longer" (ACE2 LVE STR YTE) antibody clearly out-performs the "LiVE" (ACE2 LVE STR) mAb. The "LiVE Longer" (ACE2 LVE STR YTE) antibody has more than twice the percentage of neutralization of live SARS-CoV-2 in human lung organoids as the "LiVE" (ACE2 LVE STR) antibody. Because the only difference between the two antibodies is the IgG Fc YTE variant, unexpectedly these results, in addition to the sVNT and BIACore results, suggest that the "LiVE Longer" (ACE2 LVE STR YTE) antibody may form IgG hexamers easier than the "LiVE" (ACE2 LVE STR) antibody. The results also show that as the SARS-CoV-2 VOC have become more infectious, the ACE2 chimeric mAbs, particularly the "LiVE Longer" ACE2 LVE STR YTE mAb, is not only variant resistant but more efficacious.

Example 14

The Neosinus device is an intranasal delivery system that can accurately target the neuroepithelium sustentacular cells of the olfactory bulb/sensory organ for the sense of smell.

The neuroepithelium sustentacular cells express extremely high levels of ACE2 and TMPRSS2. SARS-CoV-2 receptors ACE2 and TMPRSS2 are expressed in olfactory neuroepithelia, and ACE2 and TMPRSS2 are coexpressed in supporting sustentacular cells. Sustentacular cells thus represent a potential entry door for SARS-CoV-2 in a neuronal sensory system that is in direct connection with the brain.

SEQ ID NO: 1

(UniProt Accession #Q9BYF1, an exemplary ACE2):

```
MSSSSWLLLS LVAVTAAQST IEEQAKTFLD KFNHEAEDLF YQSSLASWNY
NTNITEENVQ NMNNAGDKWS AFLKEQSTLA QMYPLQEIQN LTVKLQLQAL
QQNGSSVLSE DKSKRLNTIL NTMSTIYSTG KVCNPDNPQE CLLLEPGLNE
IMANSLDYNE RLWAWESWRS EVGKQLRPLY EEYVVLKNEM ARANHYEDYG
DYWRGDYEVN GVDGYDYSRG QLIEDVEHTF EEIKPLYEHL HAYVRAKLMN
AYPSYISPIG CLPAHLLGDM WGRFWTNLYS LTVPFGQKPN IDVTDAMVDQ
AWDAQRIFKE AEKFFVSVGL PNMTQGFWEN SMLTDPGNVQ KAVCHPTAWD
LGKGDFRILM CTKVTMDDFL TAHHEMGHIQ YDMAYAAQPF LLRNGANEGF
HEAVGEIMSL SAATPKHLKS IGLLSPDFQE DNETEINFLL KQALTIVGTL
PFTYMLEKWR WMVFKGEIPK DQWMKKWWEM KREIVGVVEP VPHDETYCDP
ASLFHVSNDY SFIRYYTRTL YQFQFQEALC QAAKHEGPLH KCDISNSTEA
GQKLFNMLRL GKSEPWTLAL ENVVGAKNMN VRPLLNYFEP LFTWLKDQNK
NSFVGWSTDW SPYADQSIKV RISLKSALGD KAYEWNDNEM YLFRSSVAYA
MRQYFLKVKN QMILFGEEDV RVANLKPRIS FNFFVTAPKN VSDIIPRTEV
EKAIRMSRSR INDAFRLNDN SLEFLGIQPT LGPPNQPPVS IWLIVFGVVM
GVIVVGIVIL IFTGIRDRKK KNKARSGENP YASIDISKGE NNPGFQNTDD
VQTSF
```

SEQ ID NO: 2

(An exemplary "ACE2 LVE STR chimeric antibody," "ACE2 LVE IgG Fc STR" or "LiVE"):

```
QSTIEEQAKLFLDKFNVEAEDLFYQSSLASWNYNTNITEENVQNMNNAGDKWS
AFLKEQSTLAQMYPLQEIQELTVKLQLQALQQNGSSVLSEDKSKRLNTILNTM
STIYSTGKVCNPDNPQECLLLEPGLNEIMANSLDYNERLWAWESWRSEVGKQL
RPLYEEYVVLKNEMARANHYEDYGDYWRGDYEVNGVDGYDYSRGQLIEDVEHT
FEEIKPLYEHLHAYVRAKLMNAYPSYISPIGCLPAHLLGDMWGRFWTNLYSLT
VPFGQKPNIDVTDAMVDQAWDAQRIFKEAEKFFVSVGLPNMTQGFWENSMLTD
PGNVQKAVCHPTAWDLGKGDFRILMCTKVTMDDFLTAHHEMGHIQYDMAYAAQ
```

-continued

PFLLRNGANEGFHEAVGEIMSLSAATPKHLKSIGLLSPDFQEDNETEINFLLK

QALTIVGTLPFTYMLEKWRWMVFKGEIPKDQWMKKWWEMKREIVGVVEPVPHD

ETYCDPASLFHVSNDYSFIRYYTRTLYQFQFQEALCQAAKHEGPLHKCDISNS

TEAGQKLFNMLRLGKSEPWTLALENVVGAKNMNVRPLLNYFEPLFTWLKDQNK

NSFVGWSTDWSPYADQSIKVRISLKSALGDKAYEWNDNEMYLFRSSVAYAMRQ

YFLKVKNQMILFGEEDVRVANLKPRISFNFFVTAPKNVSDIIPRTEVEKAIRM

SRSRINDAFRLNDNSLEFLGIQPTLGPPNQPPVSGGGGSGGGGSDKTHTCPPC

PAPESTRGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSL

SLSPGK

SEQ ID NO: 3

(An exemplary "ACE2 YVE STR chimeric antibody"):

QSTIEEQAKYFLDKFNVEAEDLFYQSSLASWNYNTNITEENVQNMNNAGDKWS

AFLKEQSTLAQMYPLQEIQELTVKLQLQALQQNGSSVLSEDKSKRLNTILNTM

STIYSTGKVCNPDNPQECLLLEPGLNEIMANSLDYNERLWAWESWRSEVGKQL

RPLYEEYVVLKNEMARANHYEDYGDYWRGDYEVNGVDGYDYSRGQLIEDVEHT

FEEIKPLYEHLHAYVRAKLMNAYPSYISPIGCLPAHLLGDMWGRFWTNLYSLT

VPFGQKPNIDVTDAMVDQAWDAQRIFKEAEKFFVSVGLPNMTQGFWENSMLTD

PGNVQKAVCHPTAWDLGKGDFRILMCTKVTMDDFLTAHHEMGHIQYDMAYAAQ

PFLLRNGANEGFHEAVGEIMSLSAATPKHLKSIGLLSPDFQEDNETEINFLLK

QALTIVGTLPFTYMLEKWRWMVFKGEIPKDQWMKKWWEMKREIVGVVEPVPHD

ETYCDPASLFHVSNDYSFIRYYTRTLYQFQFQEALCQAAKHEGPLHKCDISNS

TEAGQKLFNMLRLGKSEPWTLALENVVGAKNMNVRPLLNYFEPLFTWLKDQNK

NSFVGWSTDWSPYADQSIKVRISLKSALGDKAYEWNDNEMYLFRSSVAYAMRQ

YFLKVKNQMILFGEEDVRVANLKPRISFNFFVTAPKNVSDIIPRTEVEKAIRM

SRSRINDAFRLNDNSLEFLGIQPTLGPPNQPPVSGGGGSGGGGSDKTHTCPPC

PAPESTRGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSL

SLSPGK

SEQ ID NO: 4

(An exemplary "ACE2 LVE IgG Fc STR YTE" or "LiVE Longer"):

QSTIEEQAKLFLDKFNVEAEDLFYQSSLASWNYNTNITEENVQNMNNAGDKWS

AFLKEQSTLAQMYPLQEIQELTVKLQLQALQQNGSSVLSEDKSKRLNTILNTM

STIYSTGKVCNPDNPQECLLLEPGLNEIMANSLDYNERLWAWESWRSEVGKQL

ERPLYEEYVVLKNMARANHYEDYGDYWRGDYEVNGVDGYDYSRGQLIEDVEHT

FEEIKPLYEHLHAYVRAKLMNAYPSYISPIGCLPAHLLGDMWGRFWTNLYSLT

VPFGQKPNIDVTDAMVDQAWDAQRIFKEAEKFFVSVGLPNMTQGFWENSMLTD

PGNVQKAVCHPTAWDLGKGDFRILMCTKVTMDDFLTAHHEMGHIQYDMAYAAQ

-continued

PFLLRNGANEGFHEAVGEIMSLSAATPKHLKSIGLLSPDFQEDNETEINFLLK

QALTIVGTLPFTYMLEKWRWMVFKGEIPKDQWMKKWWEMKREIVGVVEPVPHD

ETYCDPASLFHVSNDYSFIRYYTRTLYQFQFQEALCQAAKHEGPLHKCDISNS

TEAGQKLFNMLRLGKSEPWTLALENVVGAKNMNVRPLLNYFEPLFTWLKDQNK

NSFVGWSTDWSPYADQSIKVRISLKSALGDKAYEWNDNEMYLFRSSVAYAMRQ

YFLKVKNQMILFGEEDVRVANLKPRISFNFFVTAPKNVSDIIPRTEVEKAIRM

SRSRINDAFRLNDNSLEFLGIQPTLGPPNQPPVSGGGGSGGGGSDKTHTCPPC

PAPESTRGPSVFLFPPKPKDTLYITREPEVTCVVVDVSHEDPEVKFNWYVDGV

EVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSL

SLSPGK

SEQ ID NO: 5

(An exemplary "ACE2 YVE IgG Fc STR YTE," or "ACE2 YVE [ACE2 T27Y, H34V N90E] IgG Fc STR YTE," or "ACE2 STR YVE chimeric monoclonal antibody"):

QSTIEEQAKYFLDKFNVEAEDLFYQSSLASWNYNTNITEENVQNMNNAGDKWS

AFLKEQSTLAQMYPLQEIQELTVKLQLQALQQNGSSVLSEDKSKRLNTILNTM

STIYSTGKVCNPDNPQECLLLEPGLNEIMANSLDYNERLWAWESWRSEVGKQL

RPLYEEYVVLKNEMARANHYEDYGDYWRGDYEVNGVDGYDYSRGQLIEDVEHT

FEEIKPLYEHLHAYVRAKLMNAYPSYISPIGCLPAHLLGDMWGRFWTNLYSLT

VPFGQKPNIDVTDAMVDQAWDAQRIFKEAEKFFVSVGLPNMTQGFWENSMLTD

PGNVQKAVCHPTAWDLGKGDFRILMCTKVTMDDFLTAHHEMGHIQYDMAYAAQ

PFLLRNGANEGFHEAVGEIMSLSAATPKHLKSIGLLSPDFQEDNETEINFLLK

QALTIVGTLPFTYMLEKWRWMVFKGEIPKDQWMKKWWEMKREIVGVVEPVPHD

ETYCDPASLFHVSNDYSFIRYYTRTLYQFQFQEALCQAAKHEGPLHKCDISNS

TEAGQKLFNMLRLGKSEPWTLALENVVGAKNMNVRPLLNYFEPLFTWLKDQNK

NSFVGWSTDWSPYADQSIKVRISLKSALGDKAYEWNDNEMYLFRSSVAYAMRQ

YFLKVKNQMILFGEEDVRVANLKPRISFNFFVTAPKNVSDIIPRTEVEKAIRM

SRSRINDAFRLNDNSLEFLGIQPTLGPPNQPPVSGGGGSGGGGSDKTHTCPPC

PAPESTRGPSVFLFPPKPKDTLYITREPEVTCVVVDVSHEDPEVKFNWYVDGV

EVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSL

SLSPGK

SEQ ID NO: 6

(UniProt Accession #__, an exemplary IgG Fc):

QVQLKQSGAD LVRPGASVKL SCKASGYTFT DYYINWVKQR PGQGLEWIAR

IYPGSGNTYY NEKFKGKATL TAEKSSSTAY MQLSSLTSED SAVYFCARGI

GGGFGMDYWG QGTSVTVSSA STKGPSVFPL APSSKSTSGG TAALGCLVKD

YFPEPVTVSW NSGALTSGVH TFPAVLQSSG LYSLSSVVTV PSSSLGTQTY

ICNVNHKPSN TKVDKKVEPK SCDKTHTCPP CPAPELLGGP SVFLFPPKPK

DTLMISRTPE VTCVVVDVSH EDPEVKFNWY VDGVEVHNAK TKPREEQYNS

TYRVVSVLTV LHQDWLNGKE YKCKVSNKAL PAPIEKTISK AKGQPREPQV

-continued

YTLPPSRDEL TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK

SEQ ID NO: 7
(an exemplary "IgG FGc STR"):
DKTHTCPPCPAPESTRGPSVFLFPPKPKDTLMISRTPEVTCVVVDVSHEDPEV

KFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEAL

HNHYTQKSLSLSPGK

SEQ ID NO: 8
(an exemplary "IgG FGc STR YTE"):
DKTHTCPPCPAPESTRGPSVFLFPPKPKDTLYITREPEVTCVVVDVSHEDPEV

KFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEAL

HNHYTQKSLSLSPGK

SEQ ID NO: 9
(ACE2 (Gln18-Ser740) UniProt Accession #Q9BYF1):
QST IEEQAKTFLD KFNHEAEDLF YQSSLASWNY NTNITEENVQ

NMNNAGDKWS AFLKEQSTLA QMYPLQEIQN LTVKLQLQAL QQNGSSVLSE

DKSKRLNTIL NTMSTIYSTG KVCNPDNPQE CLLLEPGLNE IMANSLDYNE

RLWAWESWRS EVGKQLRPLY EEYVVLKNEM ARANHYEDYG DYWRGDYEVN

GVDGYDYSRG QLIEDVEHTF EEIKPLYEHL HAYVRAKLMN AYPSYISPIG

CLPAHLLGDM WGRFWTNLYS LTVPFGQKPN IDVTDAMVDQ AWDAQRIFKE

AEKFFVSVGL PNMTQGFWEN SMLTDPGNVQ KAVCHPTAWD LGKGDFRILM

CTKVTMDDFL TAHHEMGHIQ YDMAYAAQPF LLRNGANEGF HEAVGEIMSL

SAATPKHLKS IGLLSPDFQE DNETEINFLL KQALTIVGTL PFTYMLEKWR

WMVFKGEIPK DQWMKKWWEM KREIVGVVEP VPHDETYCDP ASLFHVSNDY

SFIRYYTRTL YQFQFQEALC QAAKHEGPLH KCDISNSTEA GQKLFNMLRL

GKSEPWTLAL ENVVGAKNMN VRPLLNYFEP LFTWLKDQNK NSFVGWSTDW

SPYADQSIKV RISLKSALGD KAYEWNDNEM YLFRSSVAYA MRQYFLKVKN

QMILFGEEDV RVANLKPRIS FNFFVTAPKN VSDIIPRTEV EKAIRMSRSR

INDAFRLNDN SLEFLGIQPT LGPPNQPPVS

SEQ ID NO: 10
(linker):
GGGGSGGGGS

SEQ ID NO: 11
(an exemplary "ACE2 LVE"):
QST IEEQAKLFLD KFNVEAEDLF YQSSLASWNY NTNITEENVQ
NMNNAGDKWS AFLKEQSTLA QMYPLQEIQE LTVKLQLQAL QQNGSSVLSE

DKSKRLNTIL NTMSTIYSTG KVCNPDNPQE CLLLEPGLNE IMANSLDYNE

RLWAWESWRS EVGKQLRPLY EEYVVLKNEM ARANHYEDYG DYWRGDYEVN

GVDGYDYSRG QLIEDVEHTF EEIKPLYEHL HAYVRAKLMN AYPSYISPIG

CLPAHLLGDM WGRFWTNLYS LTVPFGQKPN IDVTDAMVDQ AWDAQRIFKE

AEKFFVSVGL PNMTQGFWEN SMLTDPGNVQ KAVCHPTAWD LGKGDFRILM

CTKVTMDDFL TAHHEMGHIQ YDMAYAAQPF LLRNGANEGF HEAVGEIMSL

-continued

```
SAATPKHLKS IGLLSPDFQE DNETEINFLL KQALTIVGTL PFTYMLEKWR

WMVFKGEIPK DQWMKKWWEM KREIVGVVEP VPHDETYCDP ASLFHVSNDY

SFIRYYTRTL YQFQFQEALC QAAKHEGPLH KCDISNSTEA GQKLFNMLRL

GKSEPWTLAL ENVVGAKNMN VRPLLNYFEP LFTWLKDQNK NSFVGWSTDW

QMILFGEEDV RVANLKPRIS FNFFVTAPKN VSDIIPRTEV EKAIRMSRSR

INDAFRLNDN SLEFLGIQPT LGPPNQPPVS

                                              SEQ ID NO: 12
(an exemplary "ACE2 YVE"):
QST IEEQAKYFLD KFNVEAEDLF YQSSLASWNY NTNITEENVQ

NMNNAGDKWS AFLKEQSTLA QMYPLQEIQE LTVKLQLQAL QQNGSSVLSE

DKSKRLNTIL NTMSTIYSTG KVCNPDNPQE CLLLEPGLNE IMANSLDYNE

RLWAWESWRS EVGKQLRPLY EEYVVLKNEM ARANHYEDYG DYWRGDYEVN

GVDGYDYSRG QLIEDVEHTF EEIKPLYEHL HAYVRAKLMN AYPSYISPIG

CLPAHLLGDM WGRFWTNLYS LTVPFGQKPN IDVTDAMVDQ AWDAQRIFKE

AEKFFVSVGL PNMTQGFWEN SMLTDPGNVQ KAVCHPTAWD LGKGDFRILM

CTKVTMDDFL TAHHEMGHIQ YDMAYAAQPF LLRNGANEGF HEAVGEIMSL

SAATPKHLKS IGLLSPDFQE DNETEINFLL KQALTIVGTL PFTYMLEKWR

WMVFKGEIPK DQWMKKWWEM KREIVGVVEP VPHDETYCDP ASLFHVSNDY

SFIRYYTRTL YQFQFQEALC QAAKHEGPLH KCDISNSTEA GQKLFNMLRL

GKSEPWTLAL ENVVGAKNMN VRPLLNYFEP LFTWLKDQNK NSFVGWSTDW

SPYADQSIKV RISLKSALGD KAYEWNDNEM YLFRSSVAYA MRQYFLKVKN

QMILFGEEDV RVANLKPRIS FNFFVTAPKN VSDIIPRTEV EKAIRMSRSR

INDAFRLNDN SLEFLGIQPT LGPPNQPPVS
```

Example 15

Sequence Appendix

Example 16

This example describes chimeric ACE2 antibodies designed to have four important characteristics: a) ultra-high affinity binding to viral targets; b) preservation of high affinity binding across variant subgroups; c) the option of strong silencing of Fc receptor function to minimize ADE of infection or C'ADE, and d) the option of binding to the FcRn receptor to increase biological half-life, particularly in upper respiratory passages. This class of chimeric molecules offers a viable new set of approaches to prophylaxis and treatment of SARS-CoV-2 and, in the future with alternate designs, other emerging viral threats yet to come. Herein, the design involves mutations to be engineered into the viral receptor portion of the chimera, which for SARS-CoV-2 is the human ACE2 protein.

Similar to Example 1, the surrogate Viral Neutralization Test was used in the form of a kit. The preparation of SARS-CoV-2 strains B.1.1.214 (GISAID accession number: EPI_ISL_2897162), BA.1 (GISAID accession number: EPI-_ISL_9638489), BA.2 (GISAID accession number: EPL_ISL_11900505), and BA.5 (GISAID accession number: EPI_ISL_14018094) was done by isolating a nasopharyngeal swab sample from a COVID-19 patient. The virus was plaque-purified and propagated in TMPRSS2/Vero cells (JCRB1818, JCRB Cell Bank). SARS-CoV-2 was stored at -80° C.

Per Example 13, airway organoids ("AO") were generated. Briefly, normal human bronchial epithelial cells (NHBE, Cat# CC-2540, Lonza) were used to generate AO. NHBE were suspended in 10 mg/ml cold Matrigel growth factor reduced basement membrane matrix. 50 μl of cell suspension was solidified on pre-warmed cell-culture treated multi-dishes at 37° C. for 10 minutes, and then 500 μl of expansion medium was added to each well. AO were cultured with AO expansion medium for 10 days. To mature the AO, expanded AO were cultured with AO differentiation medium for 5 days. In experiments evaluating the antibodies, AO were dissociated into single cells, and were then seeded into 96-well plates.

Human AO were then challenged at 24 hours of culture with the virus (MOI=0.1) in the presence or absence of fusion proteins applied at 0.0064, 0.032, 0.16, 0.8, 4, 20 and 100 μg/ml (n=3). Post 24 hours, the media was replaced with fusion proteins. Twenty-four hours thereafter, supernatants were harvested and prepared for determination of viral copy number.

The cell culture supernatant was mixed with an equal volume of 2×RNA lysis buffer (distilled water containing 0.4 U/uL SUPERase ITM RNase Inhibitor, 2% Triton X-100, 50 mM KCl, 100 mM Tris-HCl (pH 7.4), and 40% glycerol) and incubated at room temperature for 10 minutes. The mixture was diluted 10 times with distilled water. Viral RNA was quantified using a One Step TB Green PrimeScript PLUS RT -PCR Kit on a StepOnePlus real-time PCR system. The primers used in this experiment are as follows: (forward) AGCCTCTTCTCGTTCCTCATCAC and (reverse) CCGCCATTGCCAGCCATTC. Standard curves were prepared using SARS-CoV-2 RNA (105 copies/μL).

The enzyme activity of ACE2 within the chimeric fusion proteins was determined with a commercially available ACE2 assay kit (BPS Bioscience, San Diego, CA), wherein the enzyme activity was expressed as fluorescence units (FU) of fluorogenic substrate converted in 30 minutes by equal amounts of either purified recombinant human ACE2 (rhACE2) or fusion protein.

The LVE ACE2 variant was chosen based on the modeling results, as described for Example 1. The LVE ACE2 variant compared favorably to recently published crystal and cryo-EM structures of ACE2 bound to SARS-CoV-2 variants. As noted above, the substitution of E90 for the wild type N eliminates the N-linked glycan, and this relieves steric hindrance by the sugar and allows closer ACE2/RBD interactions with all other mutants tested (see FIG. 1C). The amino acid substitutions L27 and V34, which interact with SARS-CoV-2 RBD amino acids 473 and 456 versus 455 and 453, respectively (FIG. 1B), were found in modeling to produce the most stabilizing ACE2/RBD interactions (lowest D-FIRE score and $K_D$ by SPR) for the widest number of SARS-CoV-2 variants, especially when paired with the E90 substitution to eliminate the N-glycosylation (see FIGS. 1D-E and Table 1). Somewhat surprisingly, when the LVE mutant of ACE2 was paired with the YTE sequence in the IgG portion of the chimera, the measured binding affinities to several SARS-CoV-2 variants were even greater than those measured in the non-YTE construct (see Table 1). Moreover, the sVNT and infection assays reported in FIGS. 3B-D & 18-20 yielded viral neutralization data entirely consistent with the modeling and SPR binding data.

Of particular note in the context of the most recent SARS-CoV-2 Omicron variants, the SARS-CoV-2 RBD mutation N417 (w.t. is K417), along with other Omicron mutations viewed in 3D molecular modeling (see FIG. 3E, top panel), has caused this RBD amino acid to move further away from the ACE2 D30 amino acid and adopt a more vertical orientation (purple arrow next to V34), compared to the w.t. K417 which was more horizontal (not shown). Across multiple modeling simulations, the choice of valine at ACE2 position 34 offered the widest variety of favorable ACE2/RBD interactions, including with the recent the BA.1, BA.2 and BA.5 sublineages of Omicron which have lost the K417 mutation. Thus, the chimeric molecules described here may be termed "variant agnostic." Of note, substitution of a tyrosine for the leucine at position 27 (FIG. 20, far right "YVE") resulted in reduced inhibition of viral replication by Omicron subvariant BA.5, when compared to the otherwise identical LVE fusion protein, possibly due to the greater size of the tyrosine side chain relative to leucine.

Interestingly, a very recent report describing the relatively new VOC BA.4.6 showed that although BA.4.6 has mutations that allowed nearly complete escape from neutralizing antibodies such as Evusheld, the mutation R346 did not affect binding to ACE2. Thus, it was expected and demonstrated that BA.4.6 bound the fusion proteins with very high affinity (845 pM). See Table 1.

As suggested in FIG. 1F, measured binding affinities determined with S1 protein mimics (top panel) versus the RBD only (bottom panel) may have slower off-rate (longer plateau phase). This might possibly be due to the additional residues in the S1 subunit compared to the RBD alone, through some uncharacterized interaction(s) between those additional residues and either the ACE2 or IgG subdomains of the fusion proteins. In this particular case, the S subunit versus RBD of two different VOCs were analyzed (Alpha versus Delta variants in FIG. 1F, respectively), so it is unclear if the difference in off-rate was due to variant sequence or the size of the mimic analyzed.

The intentional inclusion of the YTE variant of the antibody domain of the chimera was designed to permit increased binding of the "LiVE-Longer" chimeras to the FcRn receptor, which is known to increase the biological half-life of other IgGs currently in use by 3 to 4 fold. The FcRn receptor binds primarily to the CH2/CH3 interdomain area on IgG Fc, but the Fab arms also contribute to FcRn binding. Thus, some fusion proteins such as TNFR-IgG Fc mAbs (etanercept, trade name Enbrel) have a substantially shorter half-life than normal IgG. Therefore, the incorporation of the YTE sequence in these chimeras is expected to not only saturate the FcRn widely expressed in the respiratory tract, but is predicted to substantially increase their biological half-life, e.g. in humans and/or in non-human primates. Motavizumab-YTE and Omalizumab-YTE have also been shown to have an extended half-life in healthy adult humans simply as a result of incorporating the YTE sequence, a property known to be imparted by binding of this sequence to the FcRn receptor.

Although biological half-life has not yet been tested for the fusion proteins described here, e.g. in humans or non-human primates, future pharmacokinetic and pharmacodynamic studies are expected to yield a similar half-life extension of 2-4-fold. This is a feature that no other ACE2-Fc fusion proteins to date have taken into account, and it is expected to allow lower doses, administered less frequently, to achieve therapeutic efficacy. By analogy to other mAbs containing the YTE sequence, it is expected that the chimeras described herein expressing YTE will exhibit 3-4-fold increased biological half-life, especially if administered nasally, due to high FcRn expression in the nasal and oral epithelia. The Surface Plasmon Resonance (SPR) data of FIG. 22 support this hypothesis, as the YTE construct exhibited nearly 20-fold higher binding affinity to purified FcRn (27 nM) compared to the non-YTE construct (517 nM). The lower pH of the nasal cavity (~5.5) is not expected to decrease ACE2 binding, as computational modeling of chimera-RBD binding at pH 7.4 vs 5.5 yielded DFIRE Scores of -8.54 vs. -8.01, respectively (data not shown).

In addition, processing of the LiVE Longer fusion protein through a commonly available home-use nebulizer had no significant effect on the ability of the chimera to neutralize Omicron variants in the sVNT assay (data not shown), supporting delivery of the chimeric antibodies described herein by inhalation and/or nasal application.

Also and somewhat surprisingly, the LiVE-Longer antibodies, when compared to their non-YTE counterparts, showed consistently higher binding affinities to the SARS-CoV-2 protein constructs corresponding to the Alpha variant B.1.1.7 and the Omicron variants B.1.1.529 and BA.1, when these were assayed as S1 subunits or S1 subunit trimers (see Table 1). Further, the highest affinity binding was found for the YTE chimera to the Omicron subvariant BA.2 (78 fM). This increased viral binding by the YTE variant may be related to the YTE variant increasing IgG hexamer formation. Another potential benefit of incorporating the YTE sequence arises from the expression of FcRn by endothelial cells throughout the vasculature. Recently, extracellular vimentin expressed and released by endothelial cells was shown to act as an adjuvant to ACE2, increasing ACE2-mediated entry of SARS-CoV-2 into the endothelium and thereby promoting infection. In light of these findings, high binding of the YTE chimeras to FcRn within the vasculature, together with the increased half-life that binding imparts, may act to further inhibit vimentin-mediated ACE2-dependent cell entry by the virus.

The new chimeric ACE2/Fc-silent fusion proteins described herein offer a promising new approach to prophylaxis and treatment of SARS-CoV-2 infection that rigorous pre-clinical testing has shown to be relatively variant-agnostic. On the basis of published data from preparations of monoclonal antibodies containing the YTE sequence, the biological half-life of these constructs in humans and/or non-human primates is expected to be increased 3-4-fold above that of non-YTE fusion proteins. This feature is expected to not only increase biological half-life but, due to the high expression of FcRn in nasal and oral mucosa, enable lower and less frequent dosing of compound delivered intranasally. Given the stability of these constructs at the acidic pH of the nasal mucosa, intranasal delivery or nebulization is a viable delivery route for this proposed prophylactic strategy against SARS-CoV-2 infection. By saturating the respiratory tract FcRn with the "LiVE Longer" antibody passive sterilizing immunity may be achieved. In addition, the design described here offers the possibility to exchange the ACE2 portion of the construct with other viral receptors, in future efforts to combat viral threats that are likely to emerge.

As shown in FIG. 19, the LiVE and LiVE Longer fusion proteins were highly effective at inhibiting viral replication of the B.1.1.214 (left) or BA.1 (right) SARS-CoV-2 variants when applied for 2 days to human airway organoid cultures exposed to virus. Half-maximal inhibition of viral replication was obtained by the "LiVE Longer" fusion protein at 202 ng/ml and 9.3 ng/ml for the B.1.1.214 and BA.1 variants, respectively.

FIG. 20, as described above, displays the antiviral effects of the LiVE and LiVE Longer chimeras and related constructs against the Omicron variants BA.2 and BA.5. Although all constructs potently inhibited viral replication, the most potent inhibition was observed for the LiVE and LiVE Longer chimeras against Omicron BA.5, with IC50s of 29.9 ng/ml and 26.9 ng/ml, respectively.

The data shown in FIG. 21 reveal that the chimeric fusion proteins retained very little to no enzymatic activity, when compared to equal amounts of recombinant human ACE2. Although the reasons for the lack of enzyme activity are not presently clear, they may include steric hindrance caused by the fusion of the ACE2 domain to the IgG domain, or physical conditions during fusion protein preparation that may be incompatible with preservation of enzyme activity.

Further, the substitution of a tyrosine for the leucine at position 27 (FIG. 20, far right "Y-V-E") resulted in reduced inhibition of viral replication by Omicron subvariant BA.5, when compared to the otherwise identical LVE fusion protein, possibly due to the greater size of the tyrosine side chain relative to leucine.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A chimeric ACE2-Immunoglobulin antibody, comprising:
   - an immunoglobulin region having an Fc domain;
   - two Fab arms, wherein at least one of the Fab arms is substituted with an ACE2 domain,
   - wherein the chimeric ACE2-Immunoglobulin antibody comprises the sequence set forth in SEQ ID NO: 2, SEQ ID NO: 3, SEQ ID NO: 4, or SEQ ID NO: 5.

2. The chimeric ACE2-Immunoglobulin antibody of claim 1, wherein the ACE2 domain binds to each of two or more SARS CoV-2 variants with a binding affinity indicated by $K_D$ less than 10 nM, wherein binding to a SARS-CoV-2 variant comprises binding to one of an S1 subunit, a spike protein trimer, or the receptor binding domain (RBD).

3. The chimeric ACE2-Immunoglobulin antibody of claim 2 wherein one of the two or more SARS CoV-2 variants is an Omicron variant.

4. The chimeric ACE2-Immunoglobulin antibody of claim 2, wherein the ACE2 domain binds to the spike protein trimer of the Omicron variant with a binding affinity indicated by $K_D$ less than 0.9 nM (900 pM).

5. The chimeric ACE2-Immunoglobulin antibody of claim 1, wherein
   - the antibody is capable of neutralizing the binding of SARS CoV-2 to human ACE2,
   - the antibody has a binding affinity for FcRn indicated by $K_D$ less than 500 nM,
   - the antibody is capable of binding with decreased Fc effector functions including decreased binding to FcγRs and/or C1q, or
   - a combination of any of the above.

6. A pharmaceutical composition comprising the chimeric ACE2-Immunoglobulin antibody of claim 1 and a pharmaceutical acceptable carrier.

7. The composition of claim 6, wherein the composition is formulated for intranasal delivery or respiratory nebulization.

8. A method of treating SARS-CoV-2 infection, comprising: administering to a subject in need thereof the chimeric ACE2-Immunoglobulin antibody of claim 1, wherein the administering comprises intranasal delivery, respiratory nebulization, or injection.

9. The method of treatment of claim 8, wherein the treatment is prophylactic.

10. The chimeric ACE2-Immunoglobulin antibody of claim 1, which comprises the sequence set forth in SEQ ID NO: 2.

11. The chimeric ACE2-Immunoglobulin antibody of claim 1, which comprises the sequence set forth in SEQ ID NO: 3.

12. The chimeric ACE2-Immunoglobulin antibody of claim 1, which comprises the sequence set forth in SEQ ID NO: 4.

13. The chimeric ACE2-Immunoglobulin antibody of claim 1, which comprises the sequence set forth in SEQ ID NO: 5.

* * * * *

SEQUENCE LISTING

```
Sequence total quantity: 14
SEQ ID NO: 1            moltype = AA  length = 805
FEATURE                 Location/Qualifiers
source                  1..805
                        mol_type = protein
                        organism = Homo sapiens
SEQUENCE: 1
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                      805

SEQ ID NO: 2            moltype = AA  length = 960
FEATURE                 Location/Qualifiers
source                  1..960
                        mol_type = protein
                        organism = synthetic construct
SEQUENCE: 2
QSTIEEQAKL FLDKFNVEAE DLFYQSSLAS WNYNTNITEE NVQNMNNAGD KWSAFLKEQS  60
TLAQMYPLQE IQELTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
```

-continued

```
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVSGGGGSGG GGSDKTHTCP PCPAPESTRG PSVFLFPPKP KDTLMISRTP EVTCVVVDVS  780
HEDPEVKFNW YVDGVEVHNA KTKPREEQYN STYRVVSVLT VLHQDWLNGK EYKCKVSNKA  840
LPAPIEKTIS KAKGQPREPQ VYTLPPSRDE LTKNQVSLTC LVKGFYPSDI AVEWESNGQP  900
ENNYKTTPPV LDSDGSFFLY SKLTVDKSRW QQGNVFSCSV MHEALHNHYT QKSLSLSPGK  960

SEQ ID NO: 3            moltype = AA  length = 960
FEATURE                 Location/Qualifiers
source                  1..960
                        mol_type = protein
                        organism = synthetic construct
SEQUENCE: 3
QSTIEEQAKY FLDKFNVEAE DLFYQSSLAS WNYNTNITEE NVQNMNNAGD KWSAFLKEQS  60
TLAQMYPLQE IQELTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVSGGGGSGG GGSDKTHTCP PCPAPESTRG PSVFLFPPKP KDTLMISRTP EVTCVVVDVS  780
HEDPEVKFNW YVDGVEVHNA KTKPREEQYN STYRVVSVLT VLHQDWLNGK EYKCKVSNKA  840
LPAPIEKTIS KAKGQPREPQ VYTLPPSRDE LTKNQVSLTC LVKGFYPSDI AVEWESNGQP  900
ENNYKTTPPV LDSDGSFFLY SKLTVDKSRW QQGNVFSCSV MHEALHNHYT QKSLSLSPGK  960

SEQ ID NO: 4            moltype = AA  length = 960
FEATURE                 Location/Qualifiers
source                  1..960
                        mol_type = protein
                        organism = synthetic construct
SEQUENCE: 4
QSTIEEQAKL FLDKFNVEAE DLFYQSSLAS WNYNTNITEE NVQNMNNAGD KWSAFLKEQS  60
TLAQMYPLQE IQELTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVSGGGGSGG GGSDKTHTCP PCPAPESTRG PSVFLFPPKP KDTLYITREP EVTCVVVDVS  780
HEDPEVKFNW YVDGVEVHNA KTKPREEQYN STYRVVSVLT VLHQDWLNGK EYKCKVSNKA  840
LPAPIEKTIS KAKGQPREPQ VYTLPPSRDE LTKNQVSLTC LVKGFYPSDI AVEWESNGQP  900
ENNYKTTPPV LDSDGSFFLY SKLTVDKSRW QQGNVFSCSV MHEALHNHYT QKSLSLSPGK  960

SEQ ID NO: 5            moltype = AA  length = 960
FEATURE                 Location/Qualifiers
source                  1..960
                        mol_type = protein
                        organism = synthetic construct
SEQUENCE: 5
QSTIEEQAKY FLDKFNVEAE DLFYQSSLAS WNYNTNITEE NVQNMNNAGD KWSAFLKEQS  60
TLAQMYPLQE IQELTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVSGGGGSGG GGSDKTHTCP PCPAPESTRG PSVFLFPPKP KDTLYITREP EVTCVVVDVS  780
HEDPEVKFNW YVDGVEVHNA KTKPREEQYN STYRVVSVLT VLHQDWLNGK EYKCKVSNKA  840
LPAPIEKTIS KAKGQPREPQ VYTLPPSRDE LTKNQVSLTC LVKGFYPSDI AVEWESNGQP  900
ENNYKTTPPV LDSDGSFFLY SKLTVDKSRW QQGNVFSCSV MHEALHNHYT QKSLSLSPGK  960

SEQ ID NO: 6            moltype = AA  length = 449
FEATURE                 Location/Qualifiers
```

```
source                1..449
                      mol_type = protein
                      organism = Homo sapiens
SEQUENCE: 6
QVQLKQSGAD LVRPGASVKL SCKASGYTFT DYYINWVKQR PGQGLEWIAR IYPGSGNTYY  60
NEKFKGKATL TAEKSSSTAY MQLSSLTSED SAVYFCARGI GGGFGMDYWG QGTSVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 7          moltype = AA  length = 227
FEATURE               Location/Qualifiers
source                1..227
                      mol_type = protein
                      organism = Homo sapiens
SEQUENCE: 7
DKTHTCPPCP APESTRGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 8          moltype = AA  length = 227
FEATURE               Location/Qualifiers
source                1..227
                      mol_type = protein
                      organism = Homo sapiens
SEQUENCE: 8
DKTHTCPPCP APESTRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 9          moltype = AA  length = 723
FEATURE               Location/Qualifiers
source                1..723
                      mol_type = protein
                      organism = Homo sapiens
SEQUENCE: 9
QSTIEEQAKT FLDKFNHEAE DLFYQSSLAS WNYNTNITEE NVQNMNNAGD KWSAFLKEQS  60
TLAQMYPLQE IQNLTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVS                                                               723

SEQ ID NO: 10         moltype = AA  length = 10
FEATURE               Location/Qualifiers
source                1..10
                      mol_type = protein
                      organism = synthetic construct
SEQUENCE: 10
GGGGSGGGGS                                                        10

SEQ ID NO: 11         moltype = AA  length = 723
FEATURE               Location/Qualifiers
source                1..723
                      mol_type = protein
                      organism = Homo sapiens
SEQUENCE: 11
QSTIEEQAKL FLDKFNVEAE DLFYQSSLAS WNYNTNITEE NVQNMNNAGD KWSAFLKEQS  60
TLAQMYPLQE IQELTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
```

-continued

```
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVS                                                               723

SEQ ID NO: 12          moltype = AA  length = 723
FEATURE                Location/Qualifiers
source                 1..723
                       mol_type = protein
                       organism = Homo sapiens
SEQUENCE: 12
QSTIEEQAKY FLDKFNVEAE DLFYQSSLAS WNYNTNITEE NVQNMNNAGD KWSAFLKEQS  60
TLAQMYPLQE IQELTVKLQL QALQQNGSSV LSEDKSKRLN TILNTMSTIY STGKVCNPDN  120
PQECLLLEPG LNEIMANSLD YNERLWAWES WRSEVGKQLR PLYEEYVVLK NEMARANHYE  180
DYGDYWRGDY EVNGVDGYDY SRGQLIEDVE HTFEEIKPLY EHLHAYVRAK LMNAYPSYIS  240
PIGCLPAHLL GDMWGRFWTN LYSLTVPFGQ KPNIDVTDAM VDQAWDAQRI FKEAEKFFVS  300
VGLPNMTQGF WENSMLTDPG NVQKAVCHPT AWDLGKGDFR ILMCTKVTMD DFLTAHHEMG  360
HIQYDMAYAA QPFLLRNGAN EGFHEAVGEI MSLSAATPKH LKSIGLLSPD FQEDNETEIN  420
FLLKQALTIV GTLPFTYMLE KWRWMVFKGE IPKDQWMKKW WEMKREIVGV VEPVPHDETY  480
CDPASLFHVS NDYSFIRYYT RTLYQFQFQE ALCQAAKHEG PLHKCDISNS TEAGQKLFNM  540
LRLGKSEPWT LALENVVGAK NMNVRPLLNY FEPLFTWLKD QNKNSFVGWS TDWSPYADQS  600
IKVRISLKSA LGDKAYEWND NEMYLFRSSV AYAMRQYFLK VKNQMILFGE EDVRVANLKP  660
RISFNFFVTA PKNVSDIIPR TEVEKAIRMS RSRINDAFRL NDNSLEFLGI QPTLGPPNQP  720
PVS                                                               723

SEQ ID NO: 13          moltype = DNA  length = 23
FEATURE                Location/Qualifiers
source                 1..23
                       mol_type = other DNA
                       organism = synthetic construct
SEQUENCE: 13
agcctcttct cgttcctcat cac                                         23

SEQ ID NO: 14          moltype = DNA  length = 19
FEATURE                Location/Qualifiers
source                 1..19
                       mol_type = other DNA
                       organism = synthetic construct
SEQUENCE: 14
ccgccattgc cagccattc                                              19
```